US012724759B2

(12) United States Patent
Alford

(10) Patent No.: US 12,724,759 B2
(45) Date of Patent: Sep. 1, 2026

(54) SYSTEM AND METHOD FOR CAPTURING, PRESERVING, AND REPRESENTING HUMAN EXPERIENCES AND PERSONALITY THROUGH A DIGITAL INTERFACE

(71) Applicant: Janak Babaji Alford, Ottawa (CA)

(72) Inventor: Janak Babaji Alford, Ottawa (CA)

(*) Notice: Subject to any disclaimer, the term of this patent is extended or adjusted under 35 U.S.C. 154(b) by 869 days.

(21) Appl. No.: 17/889,853

(22) Filed: Aug. 17, 2022

(65) Prior Publication Data

US 2023/0172510 A1 Jun. 8, 2023

Related U.S. Application Data

(62) Division of application No. 17/889,693, filed on Aug. 17, 2022.

(Continued)

(51) Int. Cl.

| | |
|---|---|
| ***G06F 16/28*** | (2019.01) |
| ***A61B 5/16*** | (2006.01) |
| ***G06F 16/22*** | (2019.01) |
| ***G06F 16/2458*** | (2019.01) |
| ***G06N 3/006*** | (2023.01) |
| ***G06N 3/045*** | (2023.01) |

(Continued)

(52) U.S. Cl.

CPC .......... *G06F 16/2219* (2019.01); *A61B 5/167* (2013.01); *G06F 16/287* (2019.01); *G06N 3/006* (2013.01); *G06N 3/045* (2023.01); *G06N 3/094* (2023.01); *G06T 13/40* (2013.01); *G06V 10/764* (2022.01); *G06V 40/174* (2022.01); *G06V 40/20* (2022.01); *G10L 25/63* (2013.01)

(58) Field of Classification Search

CPC ........ G06T 13/40; G06N 3/006; G06N 3/094; G06N 3/045; G06N 3/08; G06V 40/174; G06V 40/20; G06V 10/764; A61B 5/167; G10L 25/63; G06F 16/285; G06F 16/287; G06F 16/2219; G06F 16/2477

See application file for complete search history.

(56) References Cited

U.S. PATENT DOCUMENTS

| | | | |
|---|---|---|---|
| 11,645,288 B2 * | 5/2023 | Sahota | G06F 16/24575 707/738 |
| 12,608,610 B1 * | 4/2026 | Pareek | G06N 3/08 |

(Continued)

*Primary Examiner* — Etienne P Leroux

(74) *Attorney, Agent, or Firm* — Alessandro Colonnier; Andrews Robichaud

(57) ABSTRACT

A system and method to capture and interact with a comprehensive digital record of an individual's biographical history and produce a synthetic model of their personality. The captured biographical history is a detailed record of this individual's actions, interactions, and experiences over a period which may span decades of their lifetime. The biographical history is indexed by areas of data variability and neural network confidence variability to identify points of likely human interest. A synthetic personality model is generated as a representation of the individual's personality structure, biases, sentiments, and traits. The synthetic personality can be interacted with through a digital interface and demonstrates the interaction patterns, triggers, and habits of the original individual. The functioning and the performance of the system over an individual's lifespan are optimized through data synthesis and disposition.

30 Claims, 45 Drawing Sheets

Related U.S. Application Data

(60) Provisional application No. 63/233,998, filed on Aug. 17, 2021.

(51) Int. Cl.

| | |
|---|---|
| ***G06N 3/08*** | (2023.01) |
| ***G06N 3/094*** | (2023.01) |
| ***G06T 13/40*** | (2011.01) |
| ***G06V 10/764*** | (2022.01) |
| ***G06V 40/16*** | (2022.01) |
| ***G06V 40/20*** | (2022.01) |
| ***G10L 25/63*** | (2013.01) |

(56) References Cited

U.S. PATENT DOCUMENTS

| | | | | |
|---|---|---|---|---|
| 2022/0351716 | A1* | 11/2022 | Kim | G06N 3/0464 |
| 2023/0222314 | A1* | 7/2023 | Alford | G06V 40/20 706/11 |
| 2026/0037484 | A1* | 2/2026 | Ajzenman | G06F 16/211 |

* cited by examiner

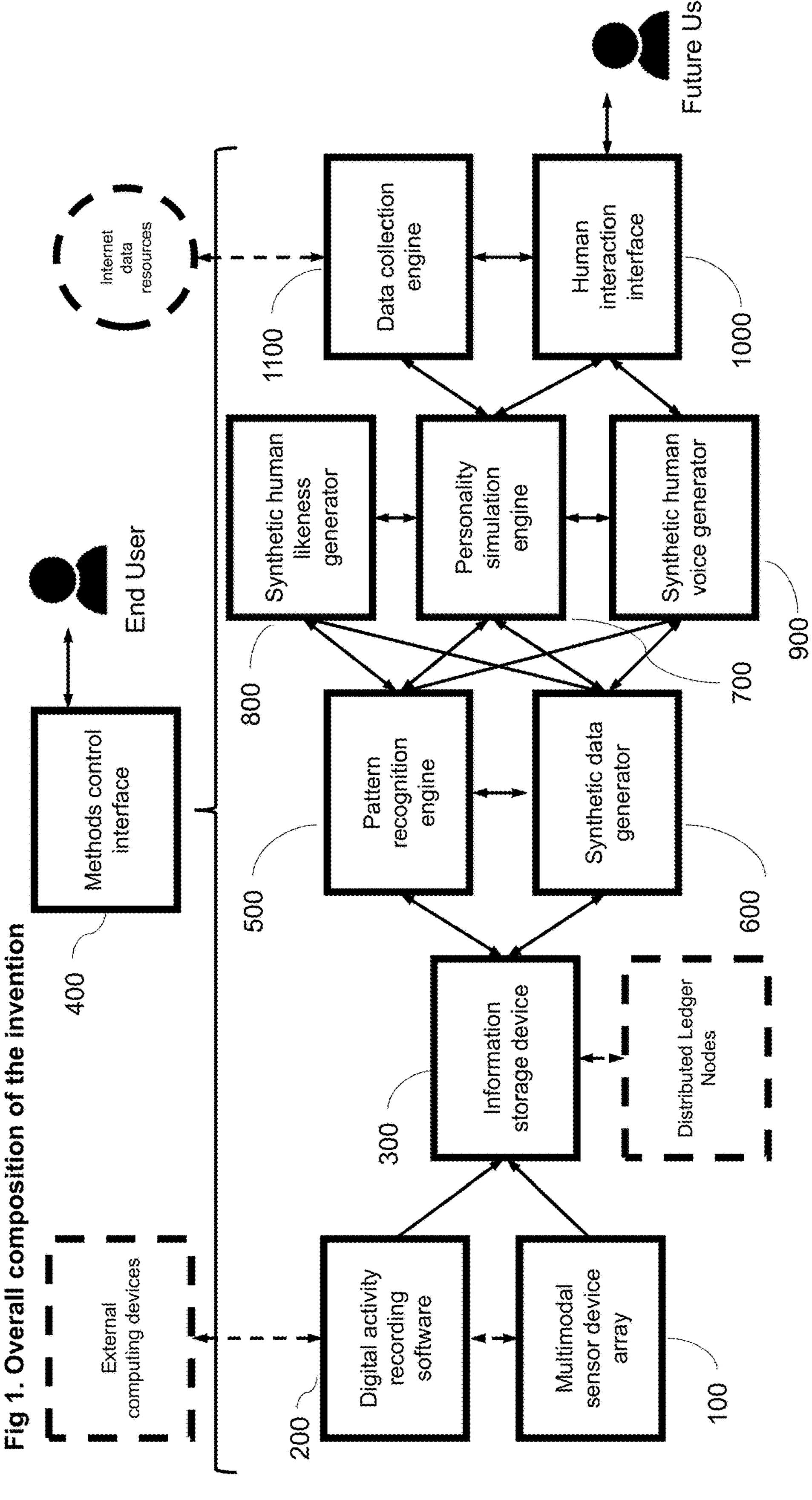
Fig 1. Overall composition of the invention

Figure 2:
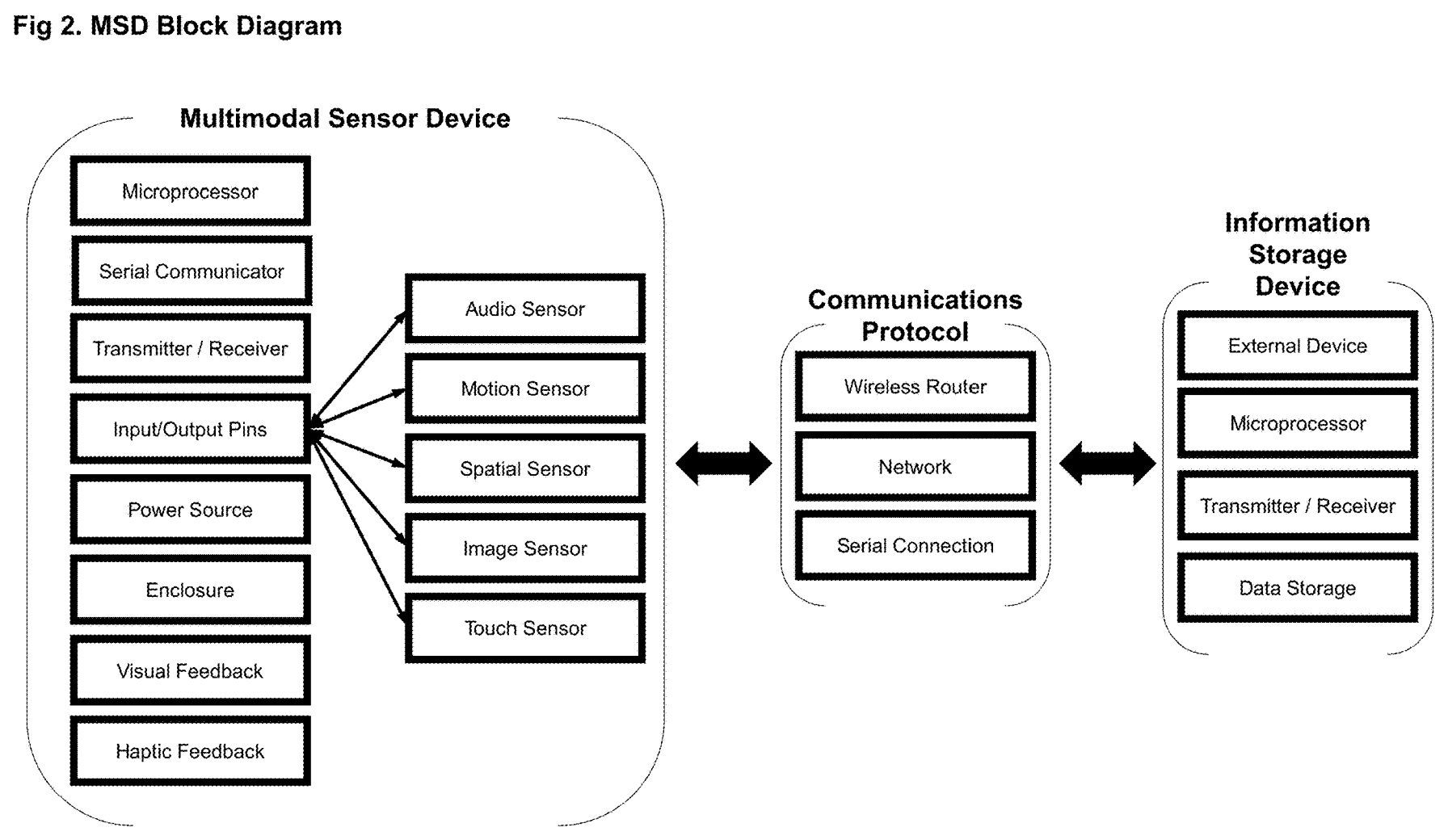

Fig 2. MSD Block Diagram

Multimodal Sensor Device

Microprocessor

Serial Communicator

Transmitter / Receiver

Input/Output Pins

Power Source

Enclosure

Visual Feedback

Haptic Feedback

Audio Sensor

Motion Sensor

Spatial Sensor

Image Sensor

Touch Sensor

Communications Protocol

Wireless Router

Network

Serial Connection

Information Storage Device

External Device

Microprocessor

Transmitter / Receiver

Data Storage

Figure 3:
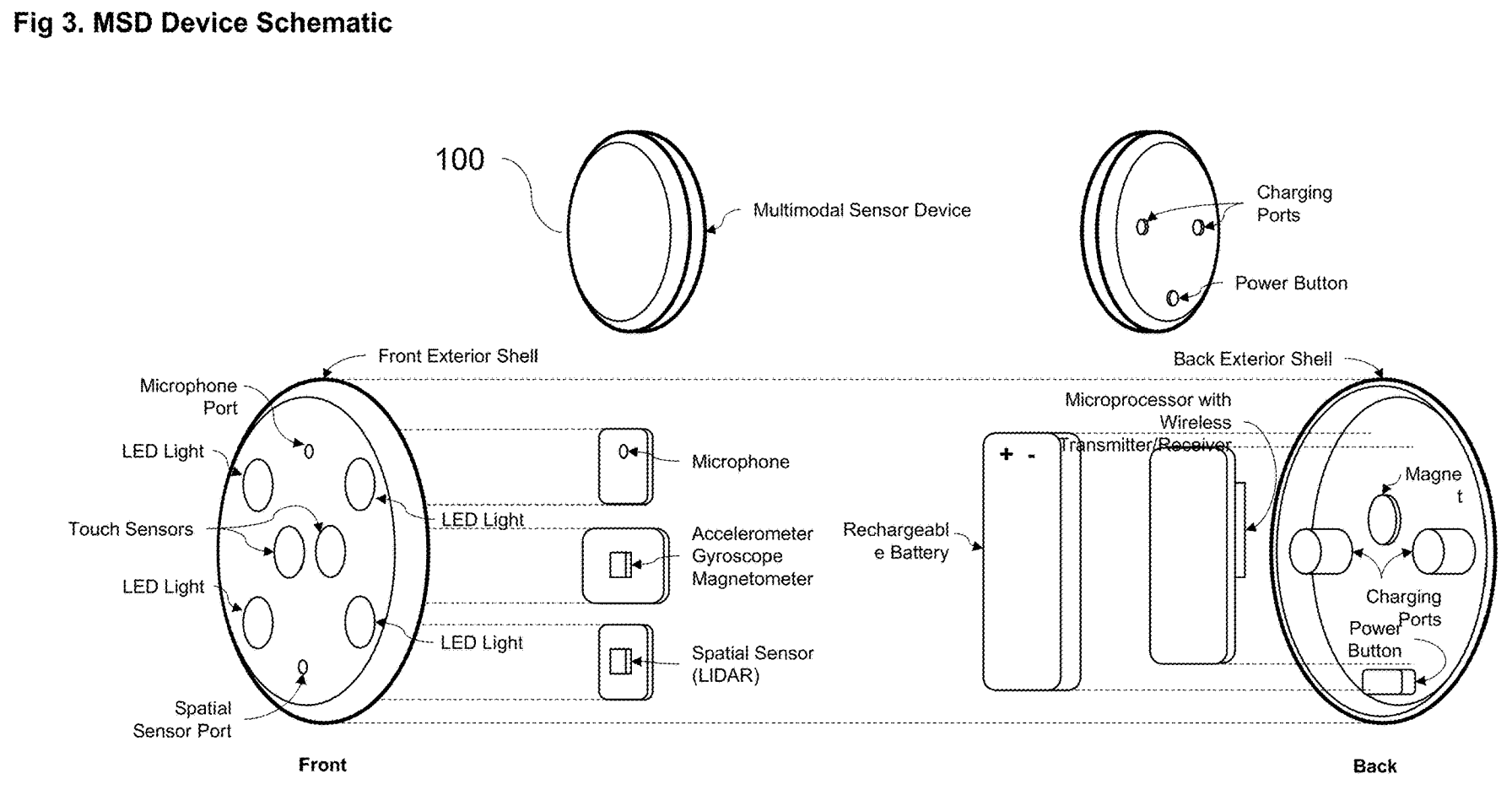

Fig 3. MSD Device Schematic

100

Multimodal Sensor Device

Charging Ports

Power Button

Front Exterior Shell

Microphone Port

LED Light

Touch Sensors

LED Light

Spatial Sensor Port

LED Light

LED Light

Front

Microphone

Accelerometer
Gyroscope
Magnetometer

Spatial Sensor
(LIDAR)

Rechargeabl
e Battery

+ -

Microprocessor with
Wireless
Transmitter/Receiver

Back Exterior Shell

Magne
t

Charging
Ports

Power
Button

Back

Fig 4. MSD Use Cases
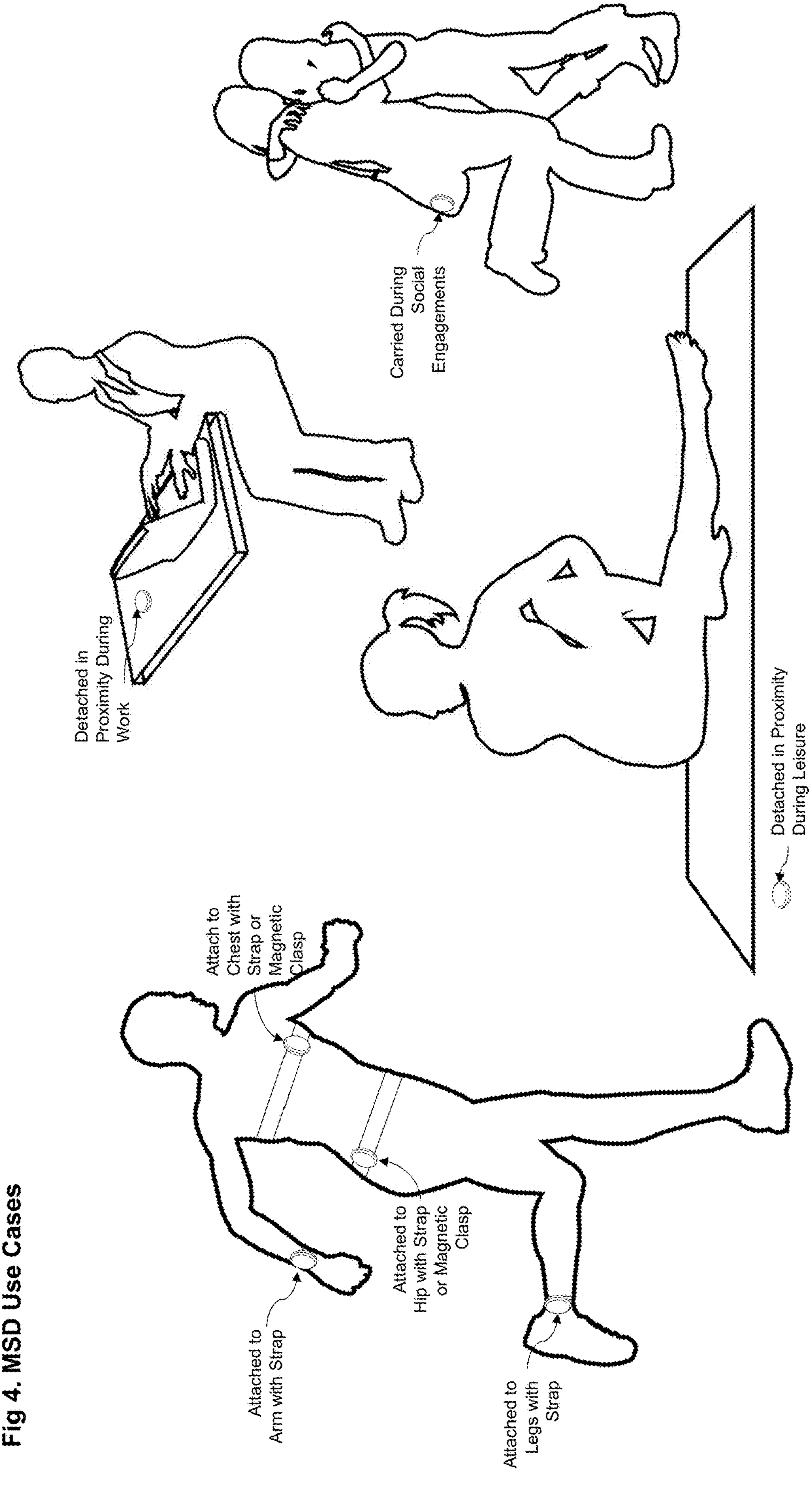

Fig 5. DAR API Connections to Hardware and Software
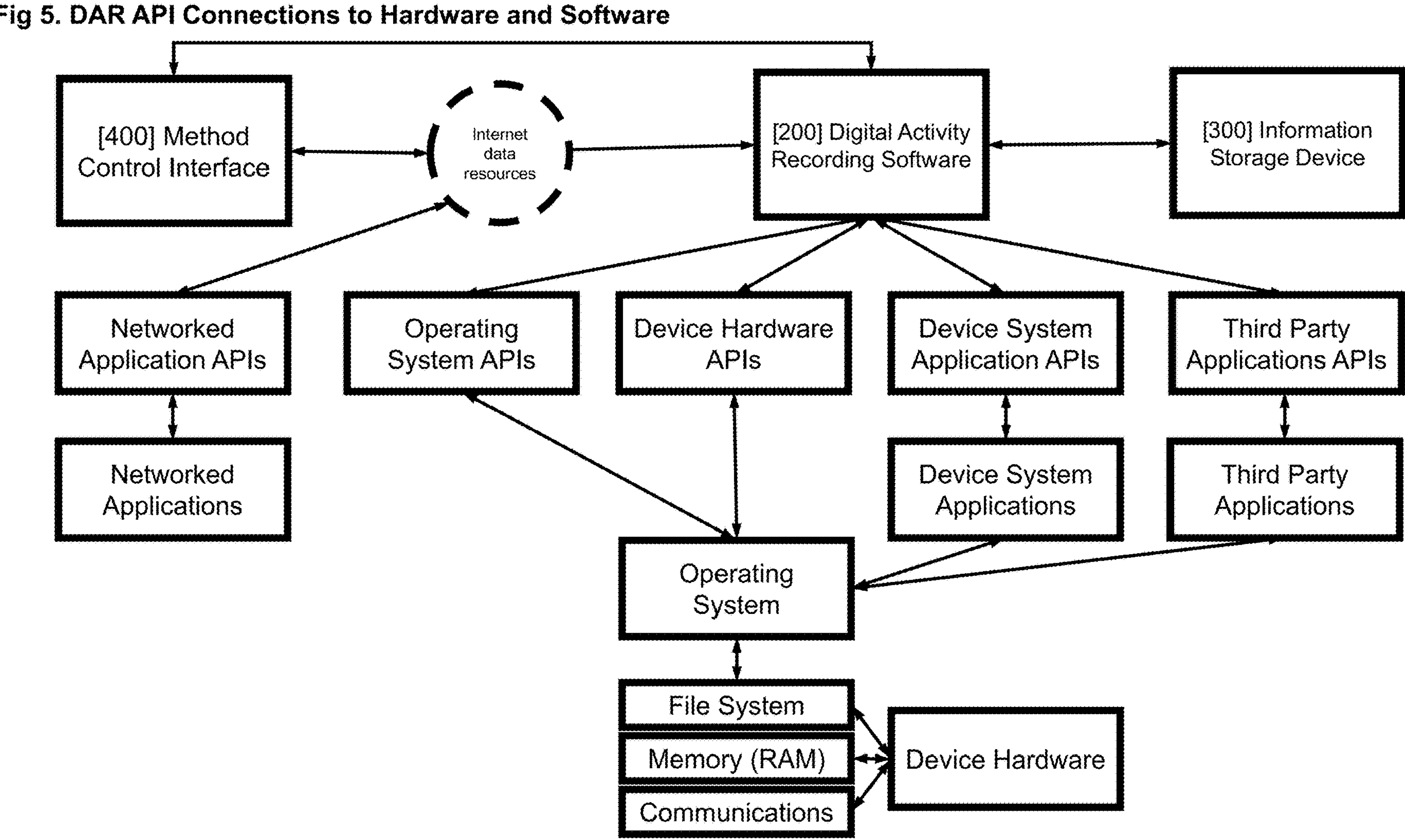

Figure 6:
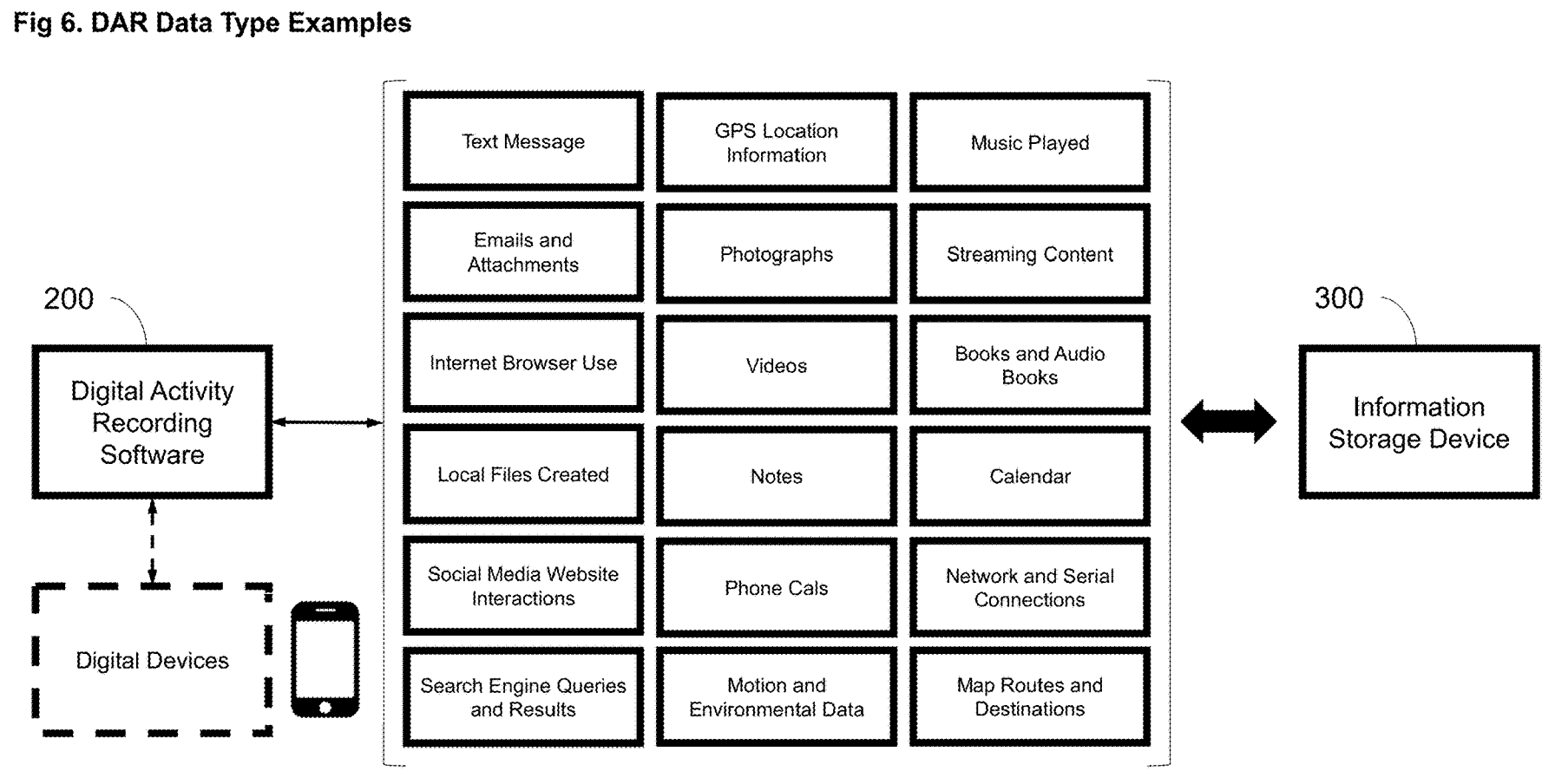

Fig 6. DAR Data Type Examples

200
Digital Activity Recording Software
Digital Devices
Text Message
GPS Location Information
Music Played
Emails and Attachments
Photographs
Streaming Content
Internet Browser Use
Videos
Books and Audio Books
Local Files Created
Notes
Calendar
Social Media Website Interactions
Phone Cals
Network and Serial Connections
Search Engine Queries and Results
Motion and Environmental Data
Map Routes and Destinations
300
Information Storage Device Fig 7. DAR Interface and Features
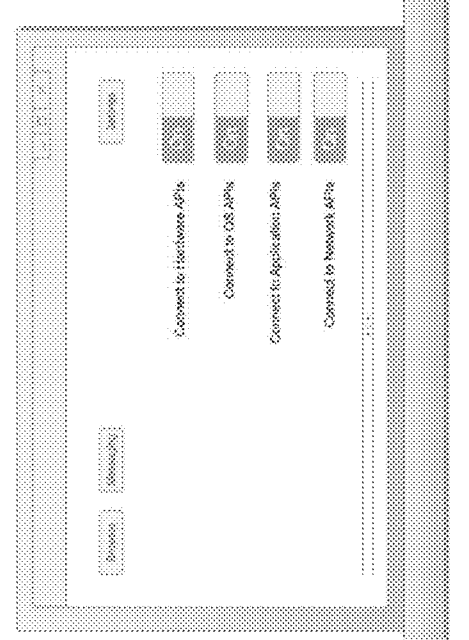
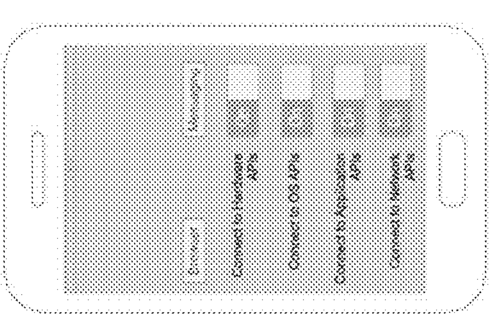
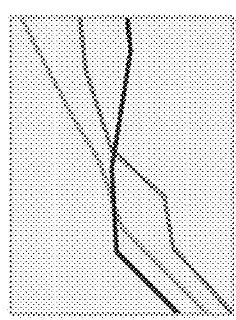
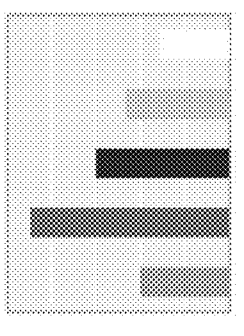
Configuration and Permissions
Authentication Fig 8. Data Transmission Types and Protocols Fig 9. ISD Block Diagram Information Storage Device Microprocessor
Cryptographic Hashing Method(s)
Application Programming Interface (API)
Data Disposition Control
Transmitter/Receiver
Cryptographic Signature Method(s)
Transactional Log Generation Method(s)
Data Augmentation Method(s)
Database(s)
Cryptographic Validation Method(s)
Performance Monitoring Interface
Distributed Instance Synchronization
File System
Data Encryption/Decryption Method(s)
Messaging Queue
Neural Network Model Storage and Retrieval
Cryptographic Key Generator
Digital Ledger Method(s)
Remote Backup Method(s)
Graphical Interface
Cryptographic Key Storage and Management
Authentication and Authorization Method(s)
Distributed Ledger Method(s)
APIs

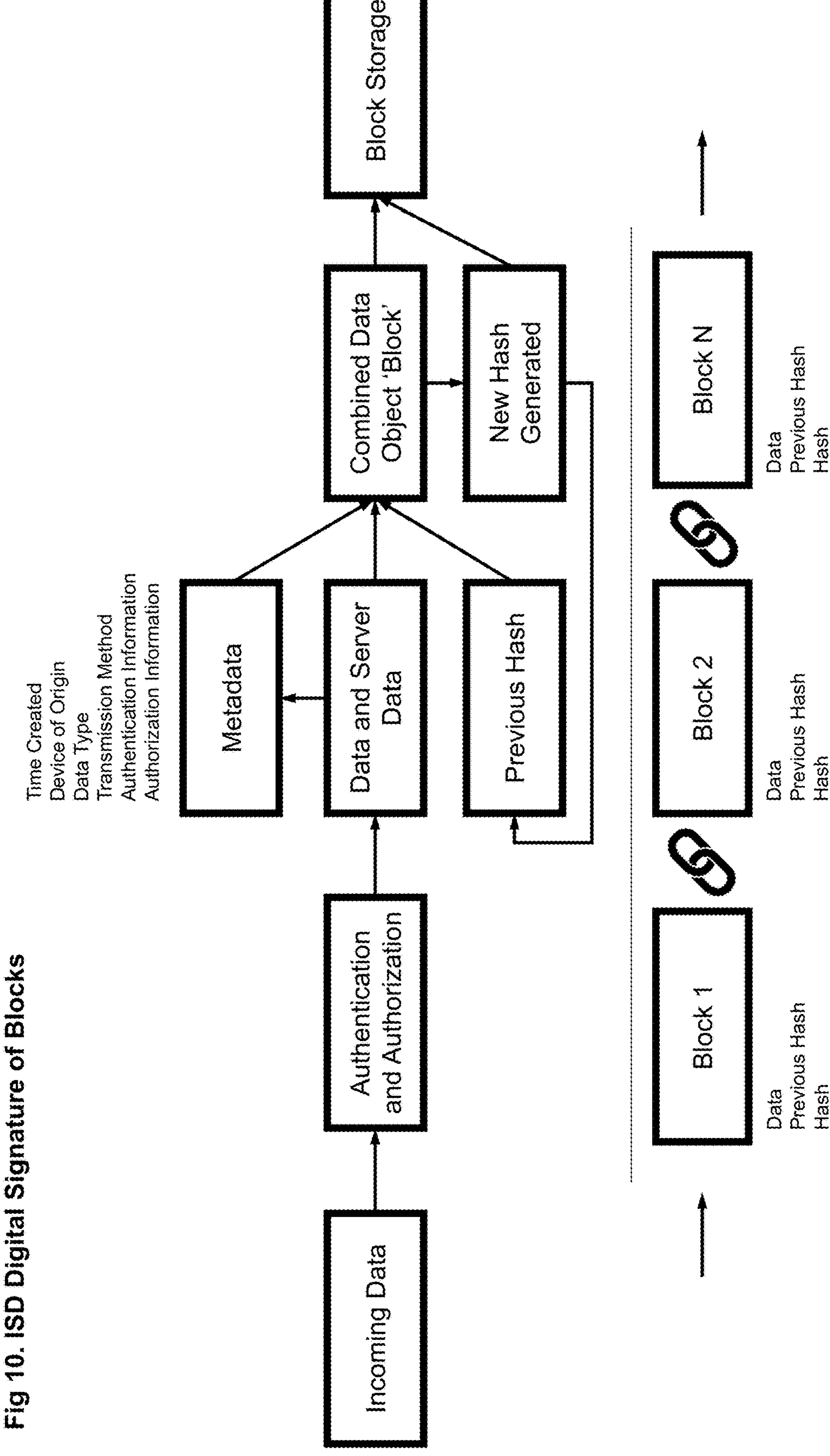
Fig 10. ISD Digital Signature of Blocks

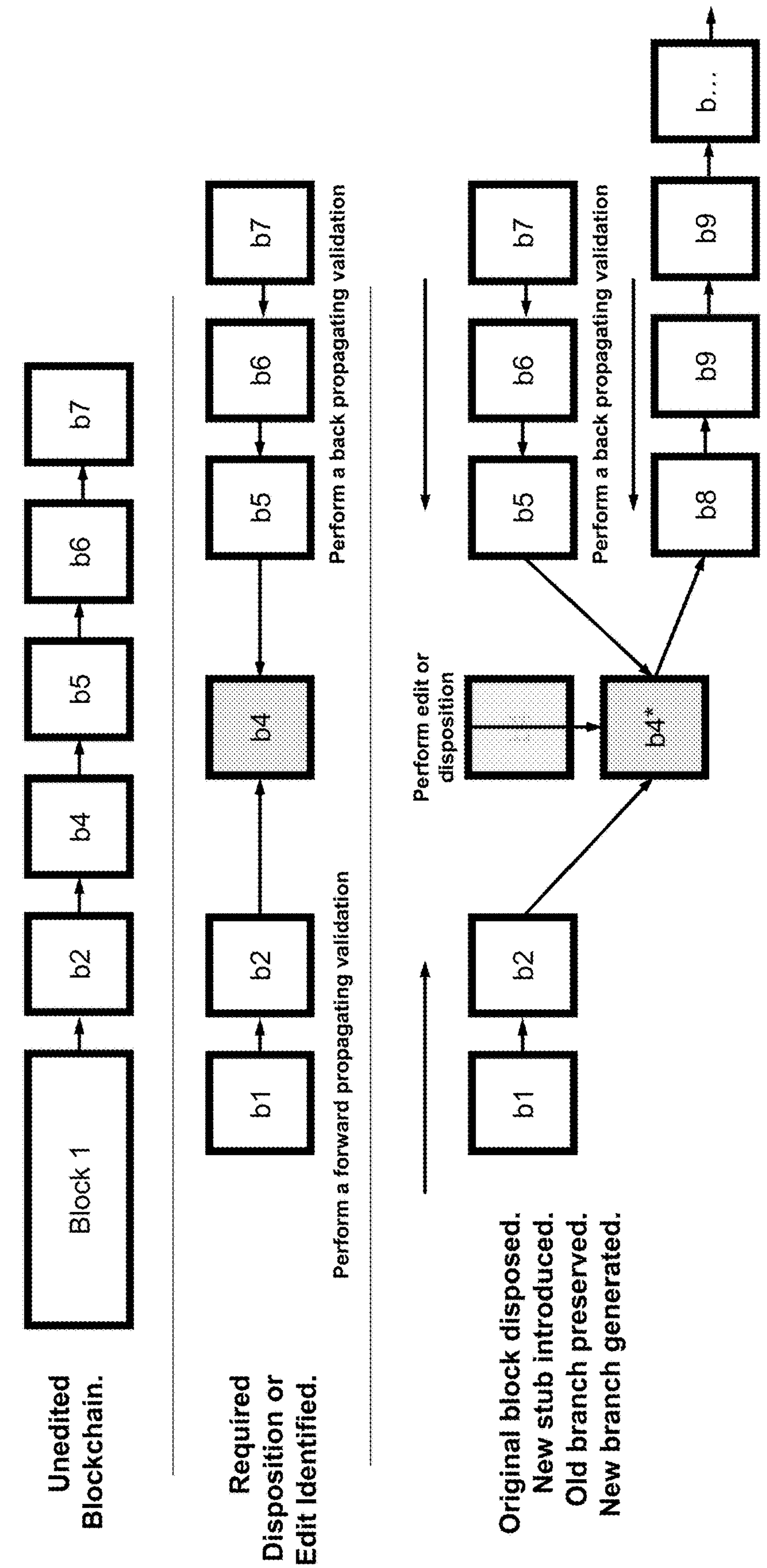
Fig 11. ISD Block Mutability

Fig 12. ISD Digital Ledgers Contributions

Primary Configuration Options

| Neural Network Model Data | Original Data |
| --- | --- |
| Recent Blocks Shared and Preserved | All Blocks Shared and Preserved |

Configurable based on capacity of each node within the network

Information Storage Device

Node

Node

Node

Node

Node

Fig 13. MCI Block Diagram
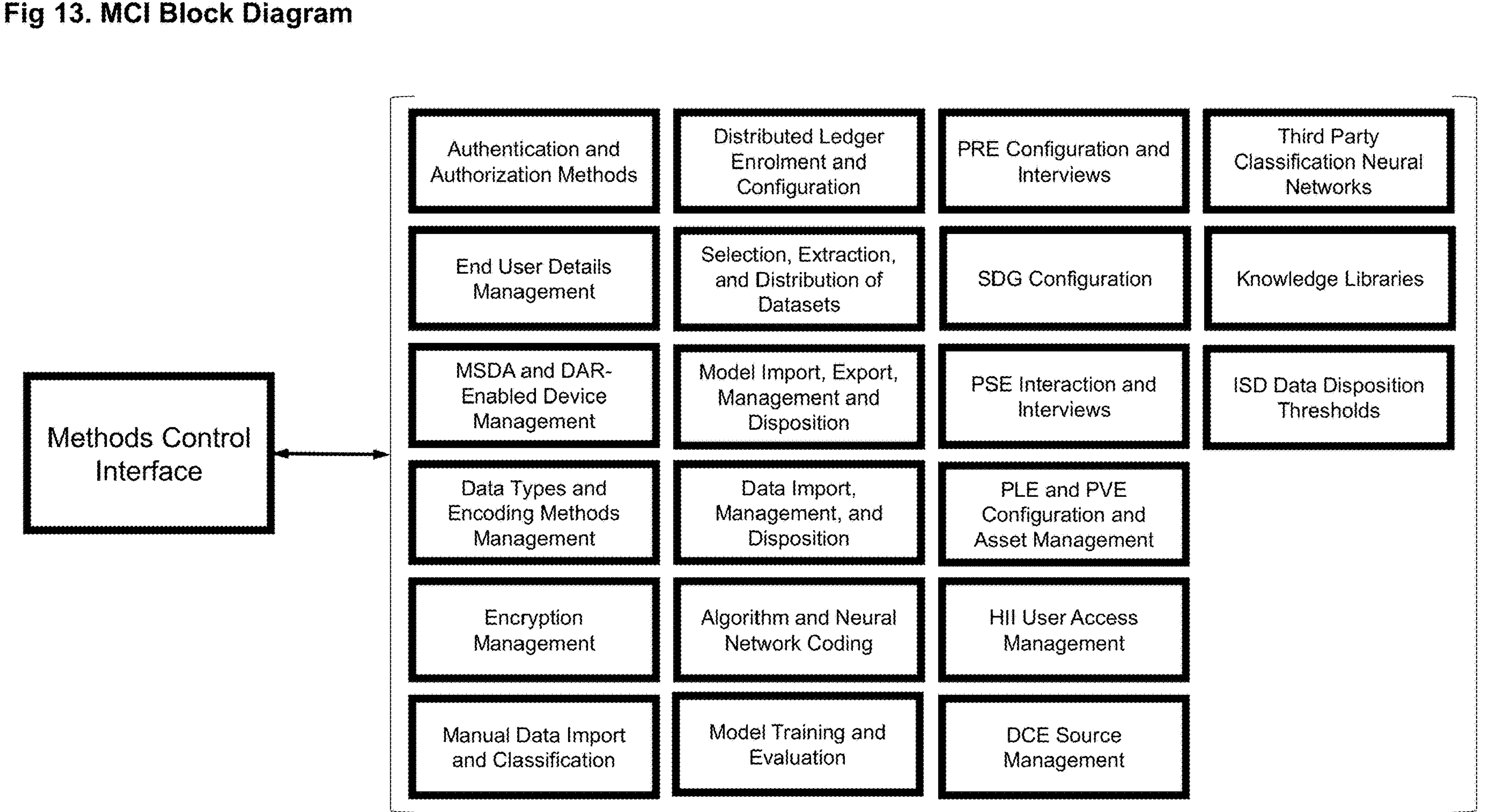

Figure 14:
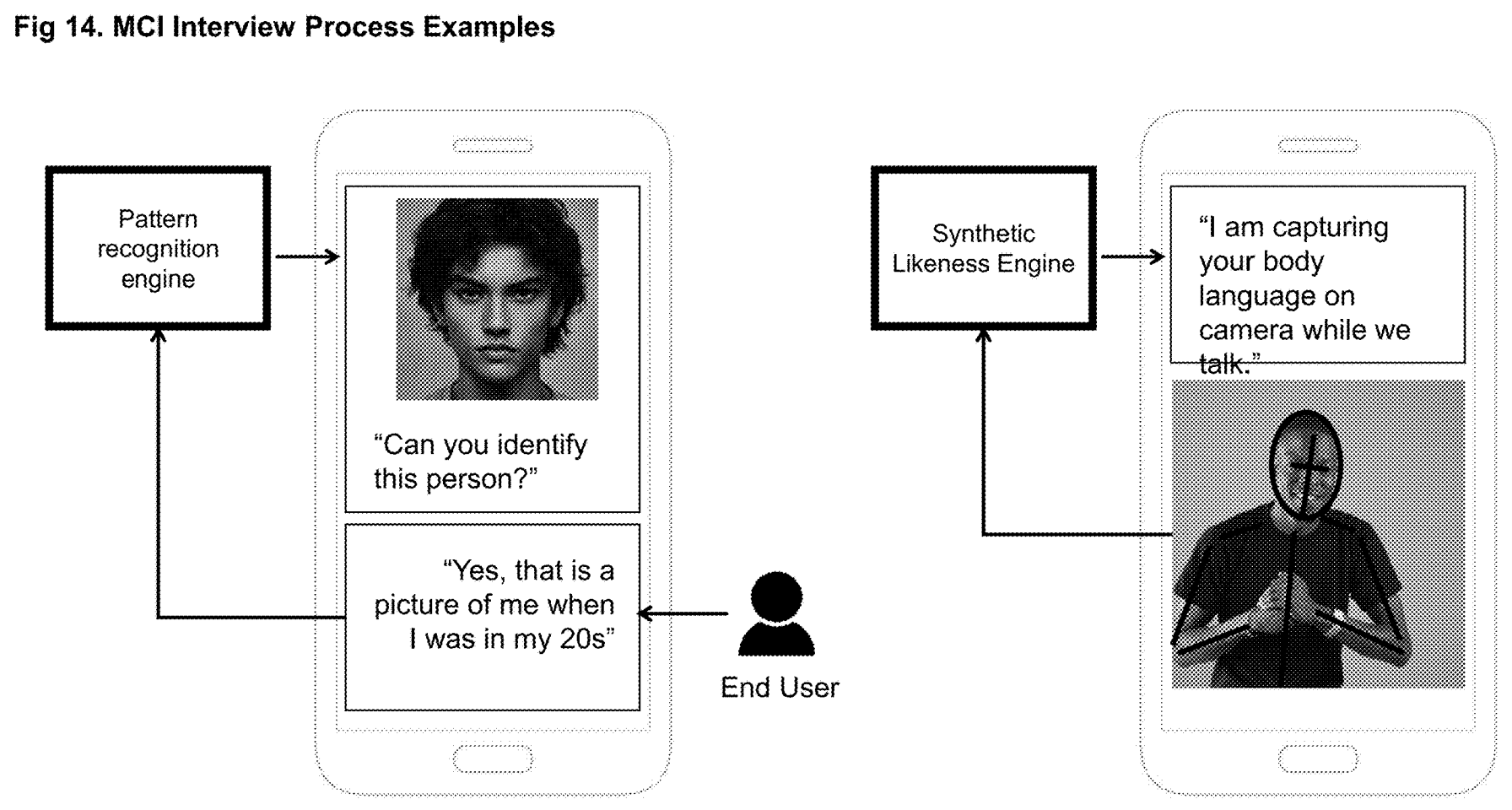

Fig 14. MCI Interview Process Examples

Pattern recognition engine

"Can you identify this person?"

"Yes, that is a picture of me when I was in my 20s"

End User

Synthetic Likeness Engine

"I am capturing your body language on camera while we talk."

Figure 15:
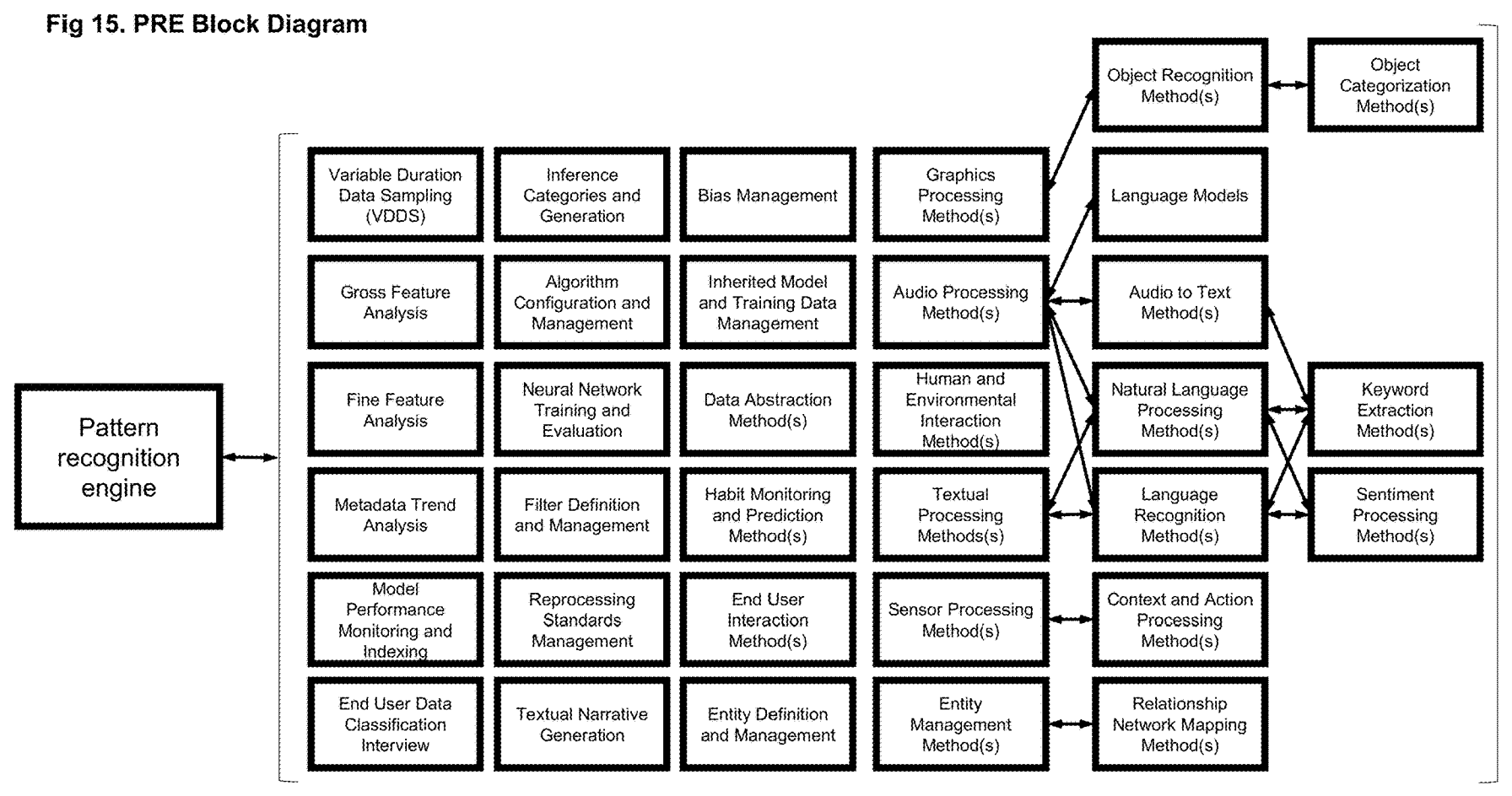

Fig 15. PRE Block Diagram

Pattern recognition engine

Variable Duration Data Sampling (VDDS)

Gross Feature Analysis

Fine Feature Analysis

Metadata Trend Analysis

Model Performance Monitoring and Indexing

End User Data Classification Interview

Inference Categories and Generation

Algorithm Configuration and Management

Neural Network Training and Evaluation

Filter Definition and Management

Reprocessing Standards Management

Textual Narrative Generation

Bias Management

Inherited Model and Training Data Management

Data Abstraction Method(s)

Habit Monitoring and Prediction Method(s)

End User Interaction Method(s)

Entity Definition and Management

Graphics Processing Method(s)

Audio Processing Method(s)

Human and Environmental Interaction Method(s)

Textual Processing Methods(s)

Sensor Processing Method(s)

Entity Management Method(s)

Object Recognition Method(s)

Language Models

Audio to Text Method(s)

Natural Language Processing Method(s)

Language Recognition Method(s)

Context and Action Processing Method(s)

Relationship Network Mapping Method(s)

Object Categorization Method(s)

Keyword Extraction Method(s)

Sentiment Processing Method(s)

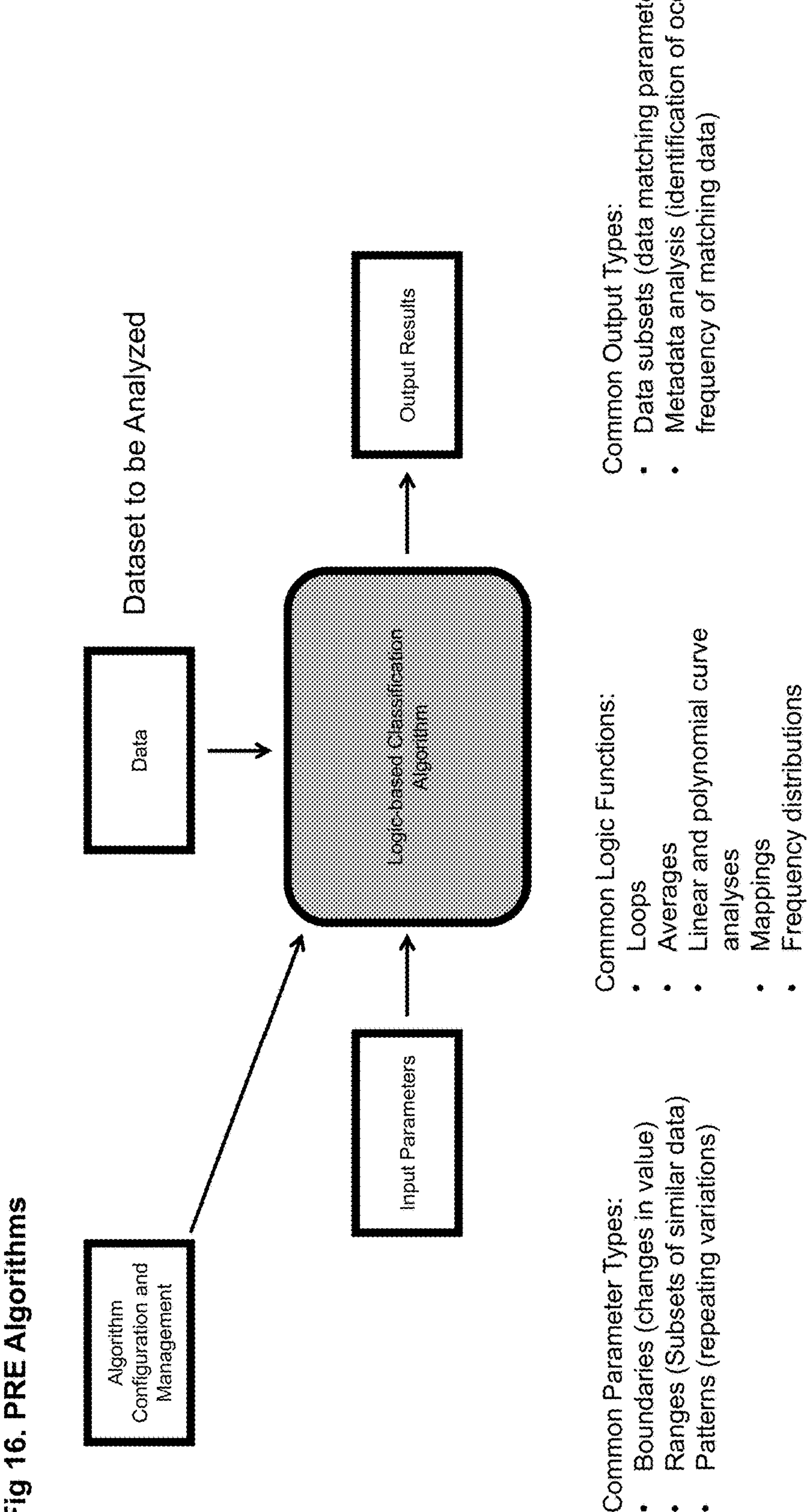
Fig 16. PRE Algorithms
Dataset to be Analyzed
Algorithm Configuration and Management
Data
Input Parameters
Logic-based Classification Algorithm
Output Results
Common Parameter Types:
• Boundaries (changes in value)
• Ranges (Subsets of similar data)
• Patterns (repeating variations)
Common Logic Functions:
• Loops
• Averages
• Linear and polynomial curve analyses
• Mappings
• Frequency distributions
Common Output Types:
• Data subsets (data matching parameters)
• Metadata analysis (identification of occurrence or frequency of matching data)

Fig 17. PRE Neural Networks

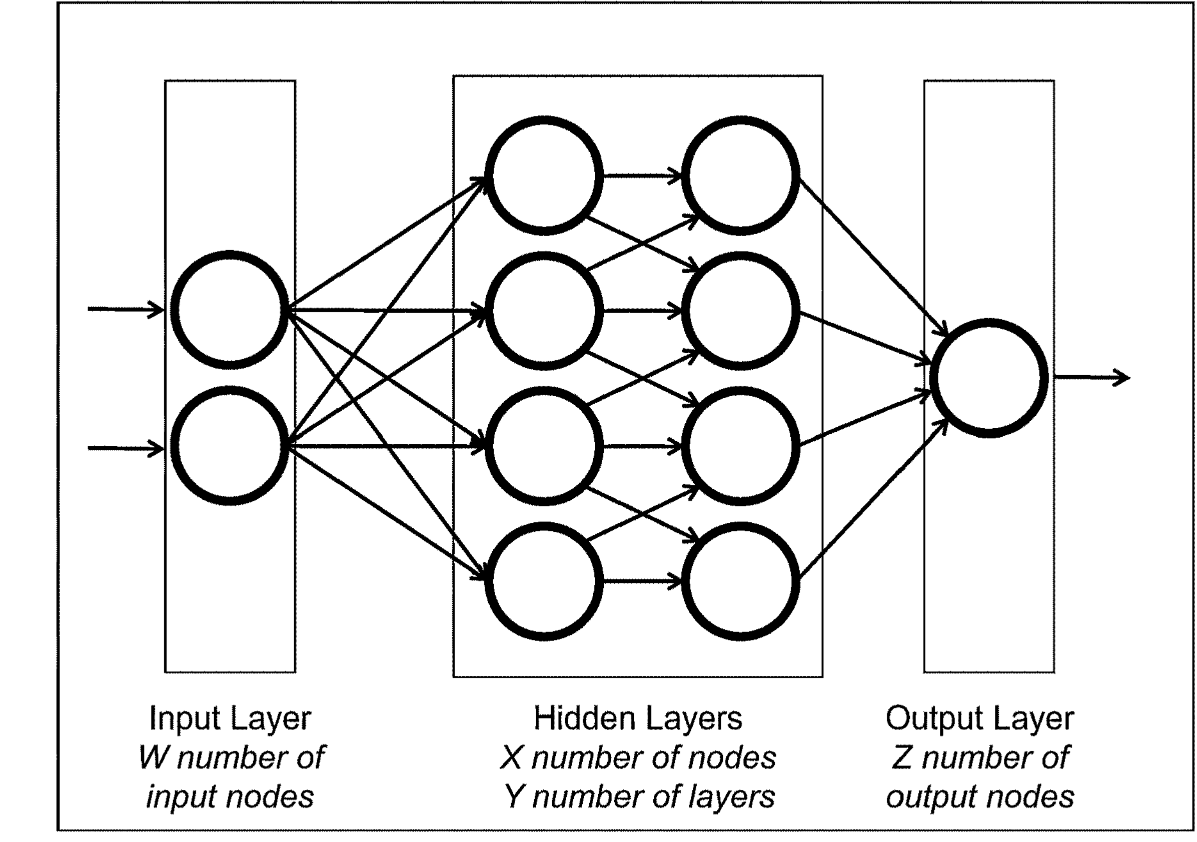

Simple Standard Neural Network Model

Reusable / Adjustable Neural Network Configuration

W, X, Y, and Z variables are all configurable. PRE implements an iterative model to configure multiple neural networks and evaluate the results of training.

Nodes utilize *weights* to modify their inputs. *Biases* are added to weights to adjust the sum of these inputs.

Figure 18:
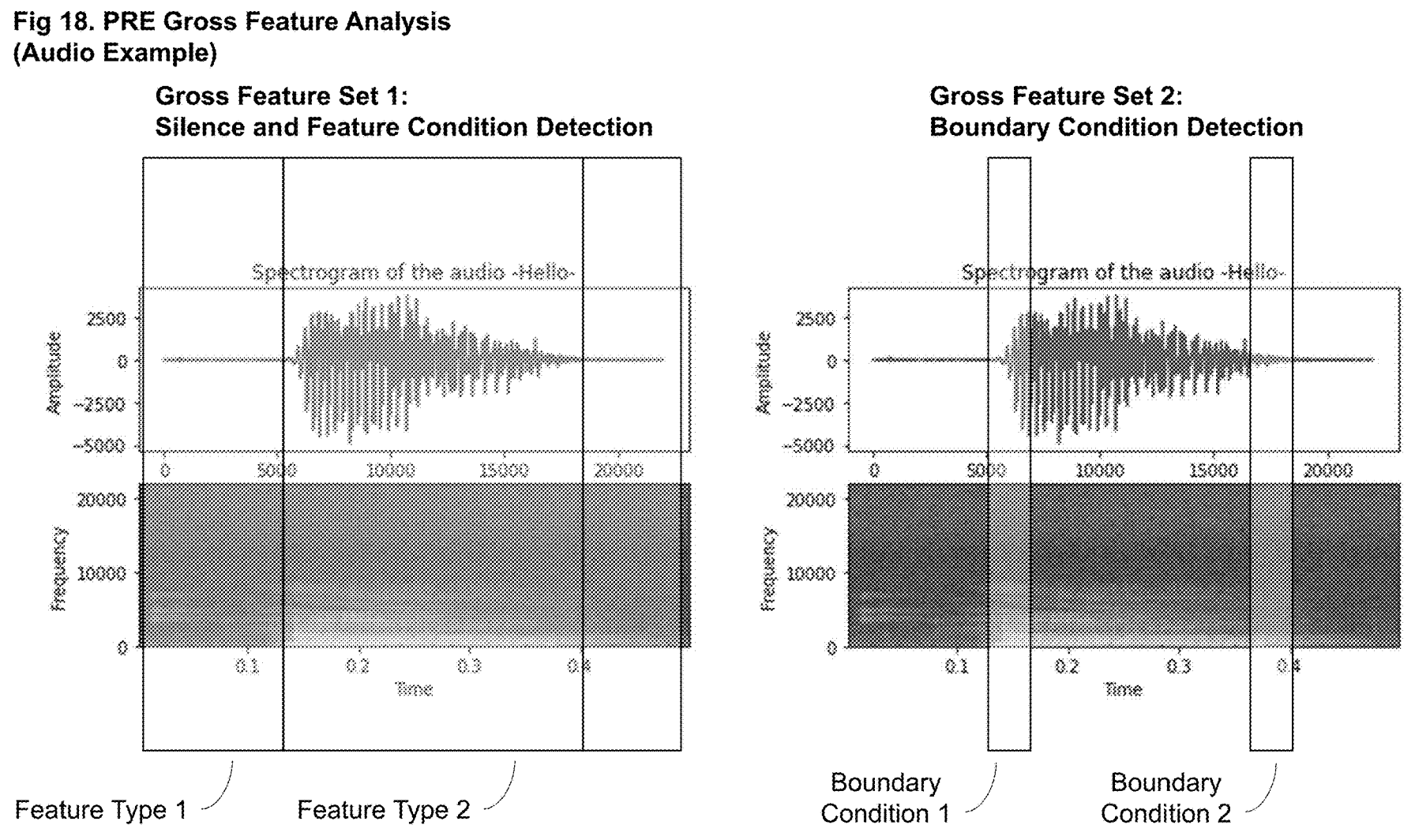

Fig 18. PRE Gross Feature Analysis (Audio Example)

Gross Feature Set 1:
Silence and Feature Condition Detection

Spectrogram of the audio -Hello-

Amplitude 2500
0
−2500
−5000

0
5000
10000
15000
20000

Frequency 20000
10000
0

0.1
0.2
0.3
0.4

Time

Feature Type 1

Feature Type 2

Gross Feature Set 2:
Boundary Condition Detection

Spectrogram of the audio -Hello-

Amplitude 2500
0
−2500
−5000

0
5000
10000
15000
20000

Frequency 20000
10000
0

0.1
0.2
0.3
0.4

Time

Boundary Condition 1

Boundary Condition 2

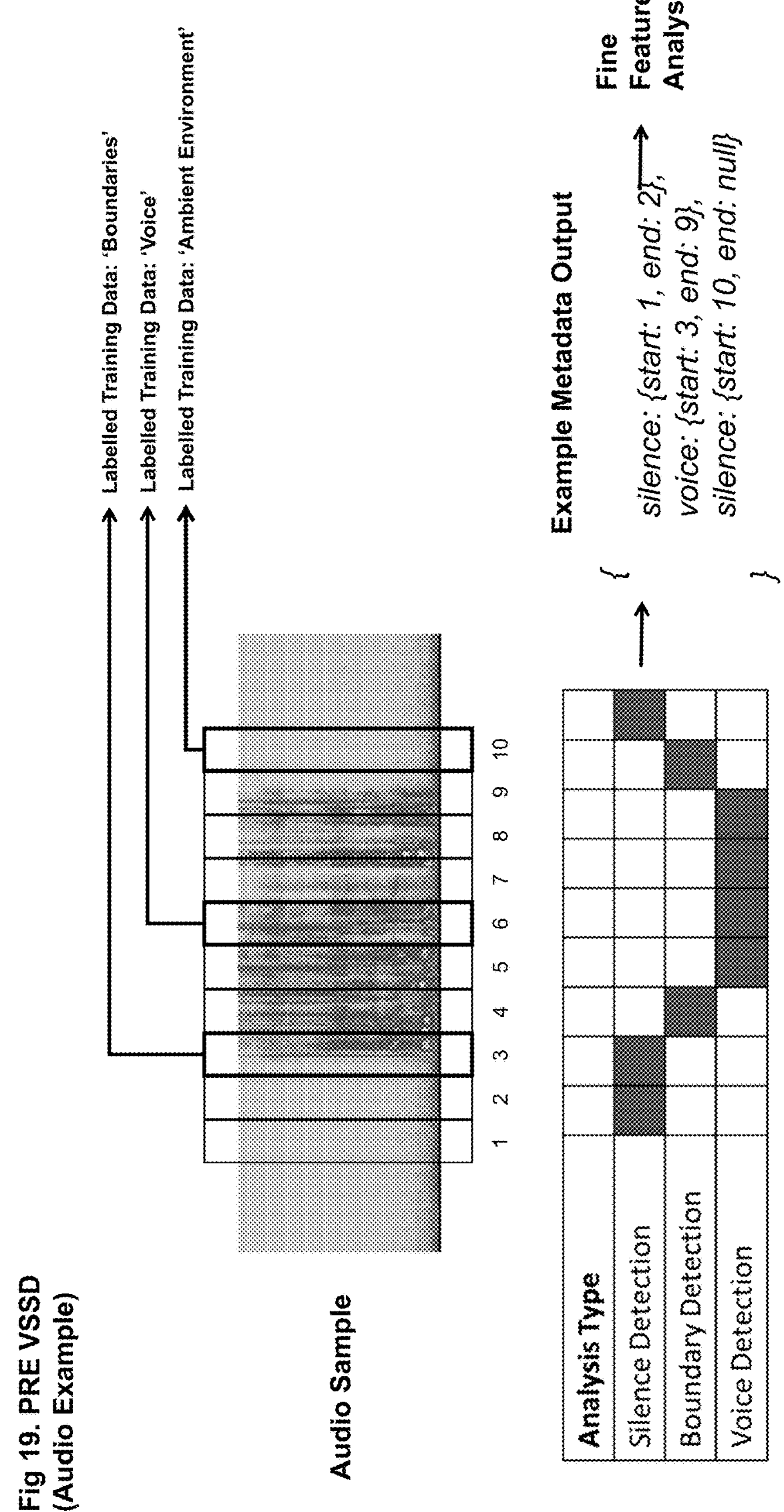
Fig 19. PRE VSSD
(Audio Example)
Audio Sample
Labelled Training Data: 'Boundaries'
Labelled Training Data: 'Voice'
Labelled Training Data: 'Ambient Environment'
1
2
3
4
5
6
7
8
9
10
Analysis Type
Silence Detection
Boundary Detection
Voice Detection
Example Metadata Output
{
silence: {start: 1, end: 2},
voice: {start: 3, end: 9},
silence: {start: 10, end: null}
}
Fine
Feature
Analysis Fig 20. PRE Fine Feature Analysis (Audio Example)

Audio Sample

Applied Analysis

| Fine Feature Analysis | Results Confidence Score |
|---|---|
| Speech to Text | 0.97 |
| Sentiment Analysis | 0.95 |
| Speaker Identification | 0.91 |
| Language Analysis | 0.99 |
| Sensor Proximity | 0.91 |
| Environment Analysis | 0.77 |
| … | … |

Example Metadata Output

```
{
  text: "Hello, people of
  Earth",
  Language:"en",
  sentiment: {
      positivity:0.6,
      happiness:0.1,
      anger: 0.0},
  speaker: {
      speakerId:1,
      adult: 0.92,
      male: 0.9,
      female: 0.12,
      estimatedAge: 35,
      proximity: 600},
  environment: {
      ambient noise: 12dB,
      echo: 0.17,
      roomId: "Living Room"
  },
}
```

Fig 21. PRE Fine Feature Analysis (Image Example)

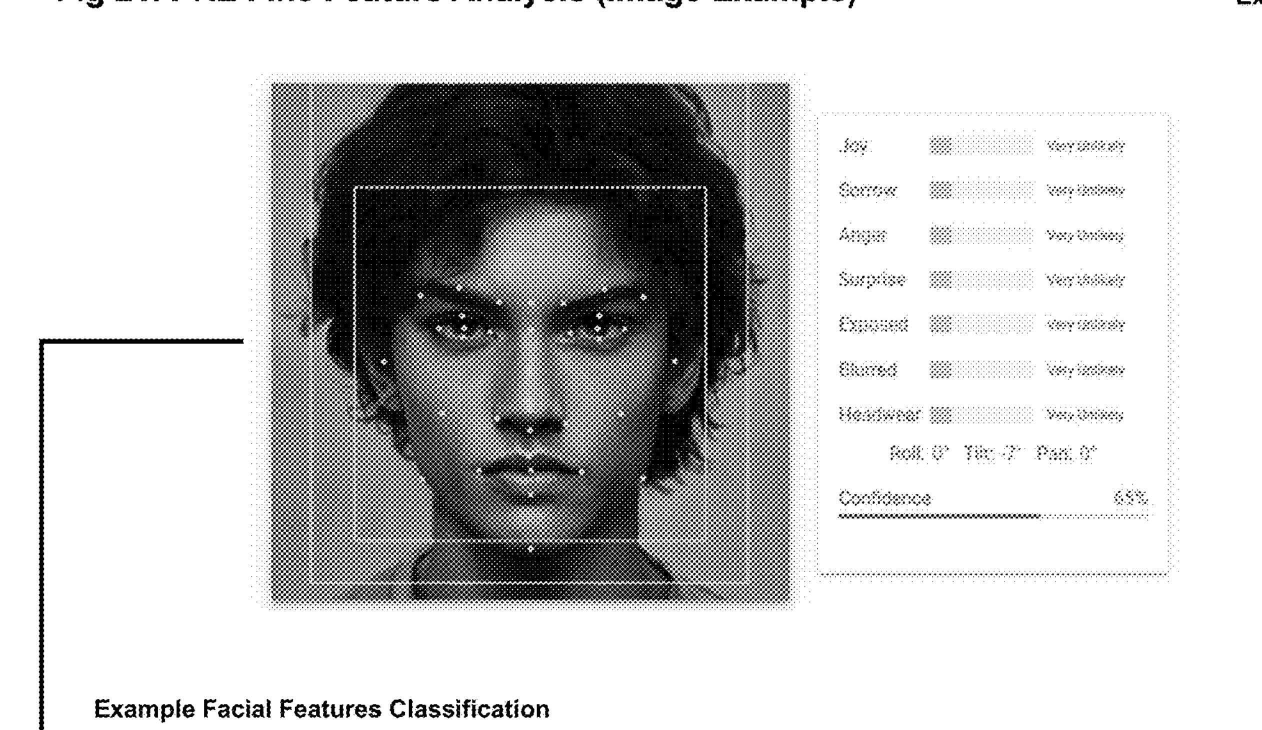

Example End User Characteristics

```
{
    "attributes": {
      "age": 28,
      "asian": 0.52738,
      "black": 0.40954,
      "gender": {
        "femaleConfidence": 0,
        "maleConfidence": 1,
        "type": "M"
      },
      "glasses": "None",
      "hispanic": 0.02168,
      "lips": "Together",
      "other": 0.0277,
      "white": 0.0137
    },
    "eyeDistance": 528,
    "face_id": 1,
    }
}
```

Example Facial Features Classification

5oclock shadow: yes (11%),
age: 22 (60%),
arched eyebrows: no (4%),
attractive: yes (27%),
bags under eyes: yes (18%),
bald: no,
beard: no (28%),
big lips: yes (13%),
big nose: yes (17%),
black hair: yes (65%),
blond hair: no,
blurry: no,
brown hair: no (67%),
bushy eyebrows: yes,
chubby: no (95%),
double chin: no,
expression: neutral,
gender: male (45%),
glasses: no,
goatee: no (61%),
gray hair: no,
heavy makeup: no (68%),
high cheekbones: no (84%),
mouth open: no (97%),
mustache: no (55%),
narrow eyes: no (47%),
oval face: no (2%),
pale skin: no (23%),
pitch: -10.19,
pointy nose: no (17%),
race: asian (91%),
receding hairline: no (84%),
rosy cheeks: no,
sideburns: no (62%),
straight hair: no (31%),
wavy hair: no (3%),
wearing earrings: no (46%),
wearing hat: no (39%),
wearing lipstick: no (60%),
wearing necklace: no (59%),
wearing necktie: no (57%),
yaw: 2.38,
young: yes,

Fig 22. PRE Multiple Character Extraction and Occurrence Measurement
Audio data may contain dozens of characteristics, each which through extraction can be used to trail a unique neural network.
Occurrence of these characteristics (frequency, volume, amplitude) within the metadata create patterns which can be mapped over time through metadata analysis.
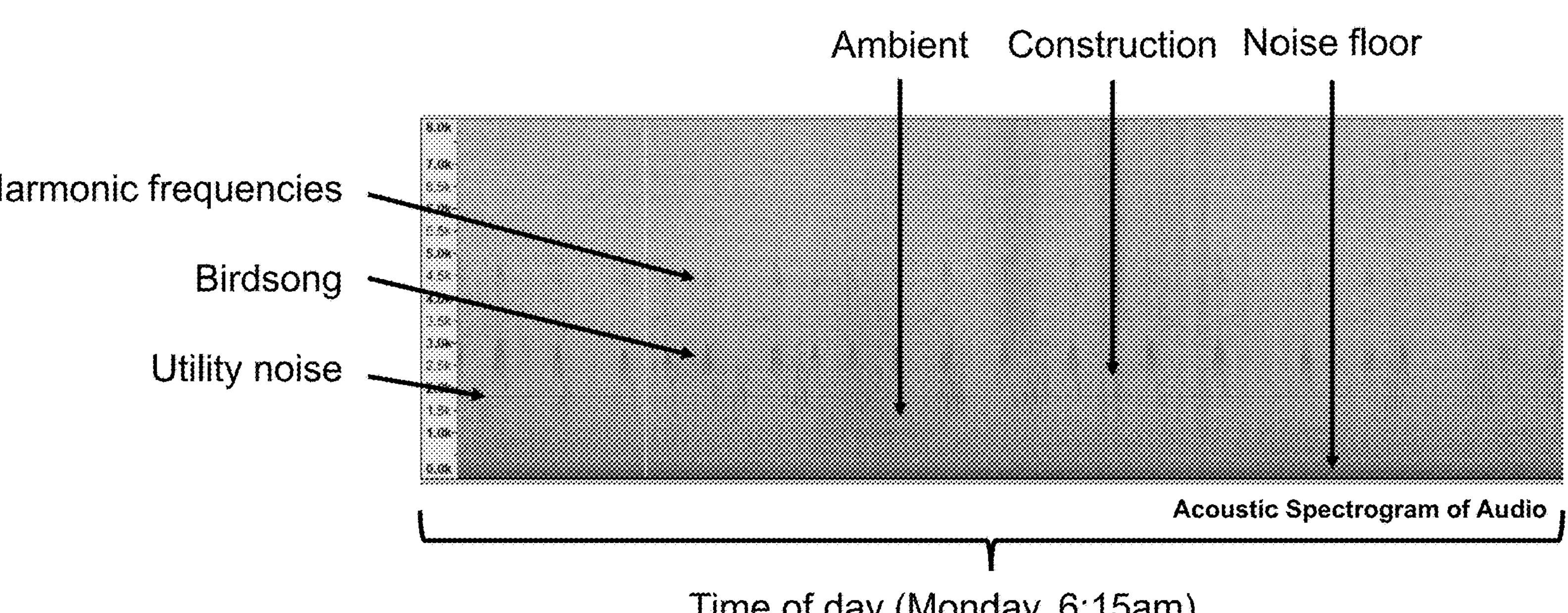

Fig 23. PRE Metadata Analysis

Single Day / Multiple Source Analysis

| Data Source | Classification | 0 | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 |
|---|---|---|---|---|---|---|---|---|---|---|---|---|---|---|---|---|---|---|---|---|---|---|---|---|---|
| Audio | Sleeping | | | | | | | | | | | | | | | | | | | | | | | | |
| Motion | Walking | | | | | | | | | | | | | | | | | | | | | | | | |
| Motion | Standing | | | | | | | | | | | | | | | | | | | | | | | | |
| GPS | Exercise | | | | | | | | | | | | | | | | | | | | | | | | |
| GPS/Audio | Home | | | | | | | | | | | | | | | | | | | | | | | | |
| GPS/Audio | Work | | | | | | | | | | | | | | | | | | | | | | | | |
| Audio | Talking | | | | | | | | | | | | | | | | | | | | | | | | |
| DAR | Messaging | | | | | | | | | | | | | | | | | | | | | | | | |

Cyclical (Day over Day) Analysis with Predictions

| Day | Classification | 0 | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 |
|---|---|---|---|---|---|---|---|---|---|---|---|---|---|---|---|---|---|---|---|---|---|---|---|---|---|
| 1 | Sleeping | | | | | | | | | | | | | | | | | | | | | | | | |
| 2 | Sleeping | | | | | | | | | | | | | | | | | | | | | | | | |
| 3 | Sleeping | | | | | | | | | | | | | | | | | | | | | | | | |
| 4 | Sleeping | | | | | | | | | | | | | | | | | | | | | | | | |
| 5 | Sleeping | | | | | | | | | | | | | | | | | | | | | | | | |
| Prediction | Sleeping | | | | | | | | | | | | | | | | | | | | | | | | |

Figure 24:
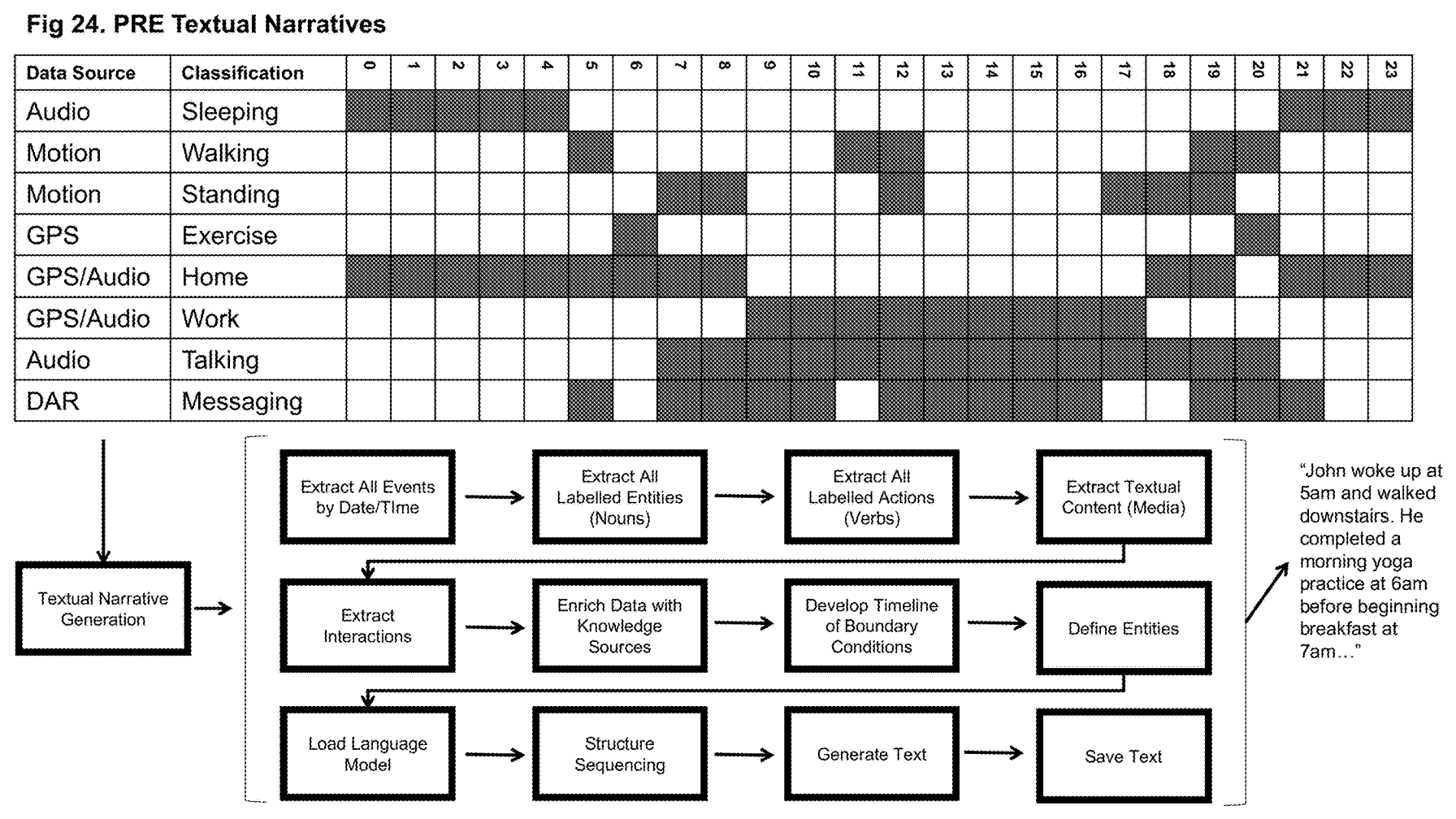

Fig 24. PRE Textual Narratives

| Data Source | Classification | 0 | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 |
|---|---|---|---|---|---|---|---|---|---|---|---|---|---|---|---|---|---|---|---|---|---|---|---|---|---|
| Audio | Sleeping | | | | | | | | | | | | | | | | | | | | | | | | |
| Motion | Walking | | | | | | | | | | | | | | | | | | | | | | | | |
| Motion | Standing | | | | | | | | | | | | | | | | | | | | | | | | |
| GPS | Exercise | | | | | | | | | | | | | | | | | | | | | | | | |
| GPS/Audio | Home | | | | | | | | | | | | | | | | | | | | | | | | |
| GPS/Audio | Work | | | | | | | | | | | | | | | | | | | | | | | | |
| Audio | Talking | | | | | | | | | | | | | | | | | | | | | | | | |
| DAR | Messaging | | | | | | | | | | | | | | | | | | | | | | | | |

Fig 25. PRE Model Visualization of Characteristic Occurrence Identification Over Time
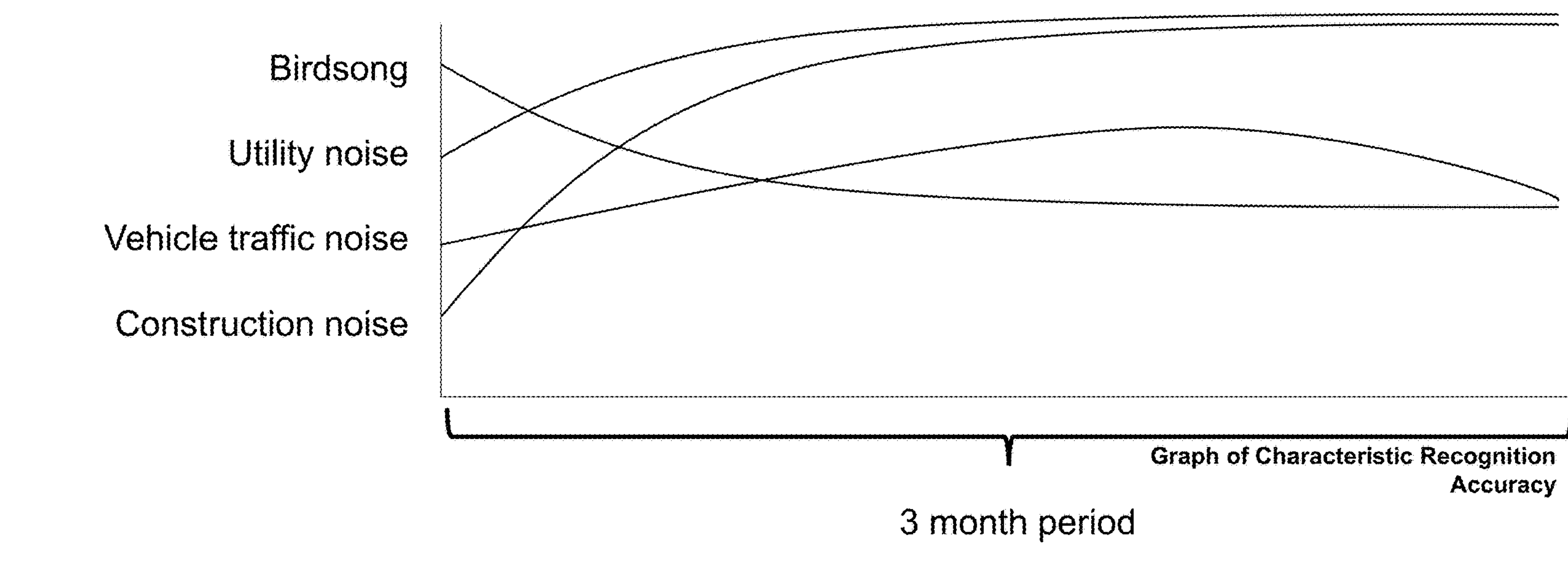
Characteristic presence may apply multiple measurement criteria including:
- Monitoring the presence of previously mapped characteristics and recording their rate of change;
- Monitoring the accuracy of each model's ability to accurately recognize characteristics Fig 26. PRE Multi-Model Consensus Divergence

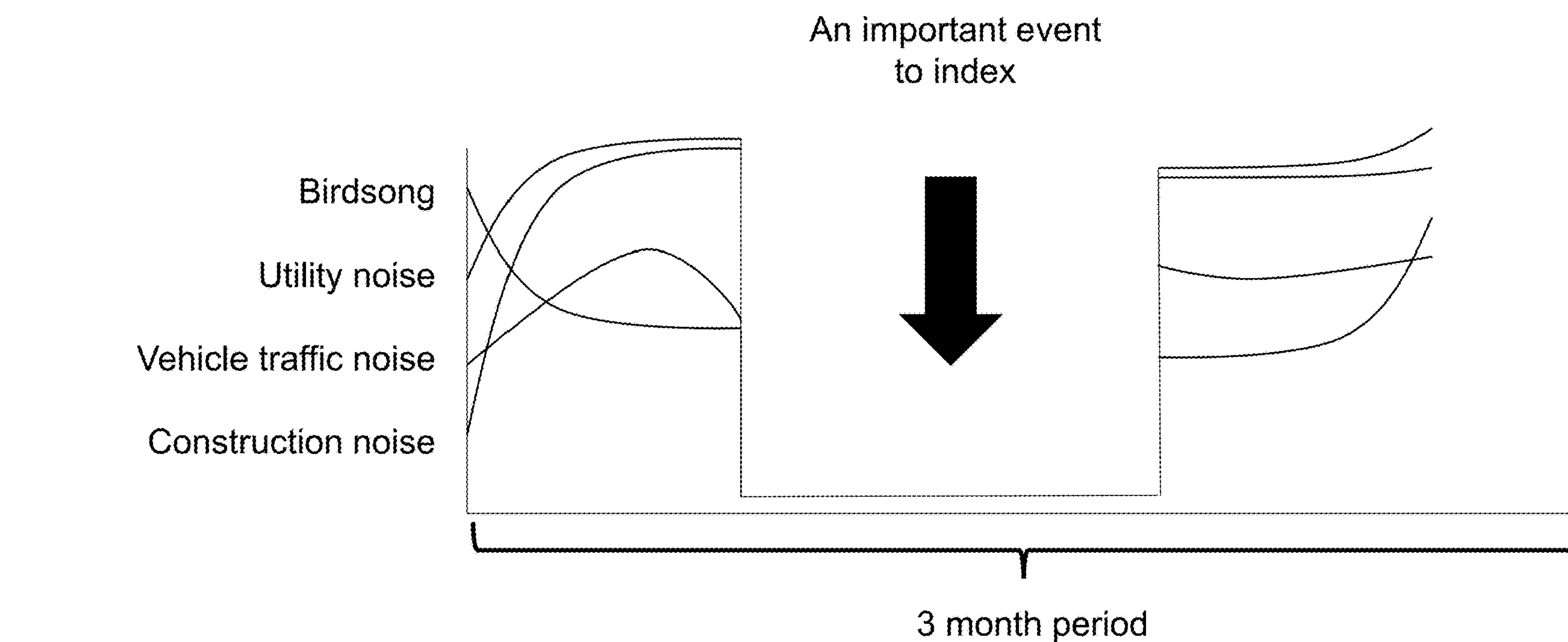

When multiple characteristic indicators change abruptly (models cease to accurately identify characteristics which have traditionally appeared in datasets) this represents “consensus divergence”

The ‘notch’ in machine learning predictive confidence indicates an unusual event that should be indexed for future analysis. Something happened to cause a change in the PRE’s ability to classify data. This notch represents an index in a biographical history.

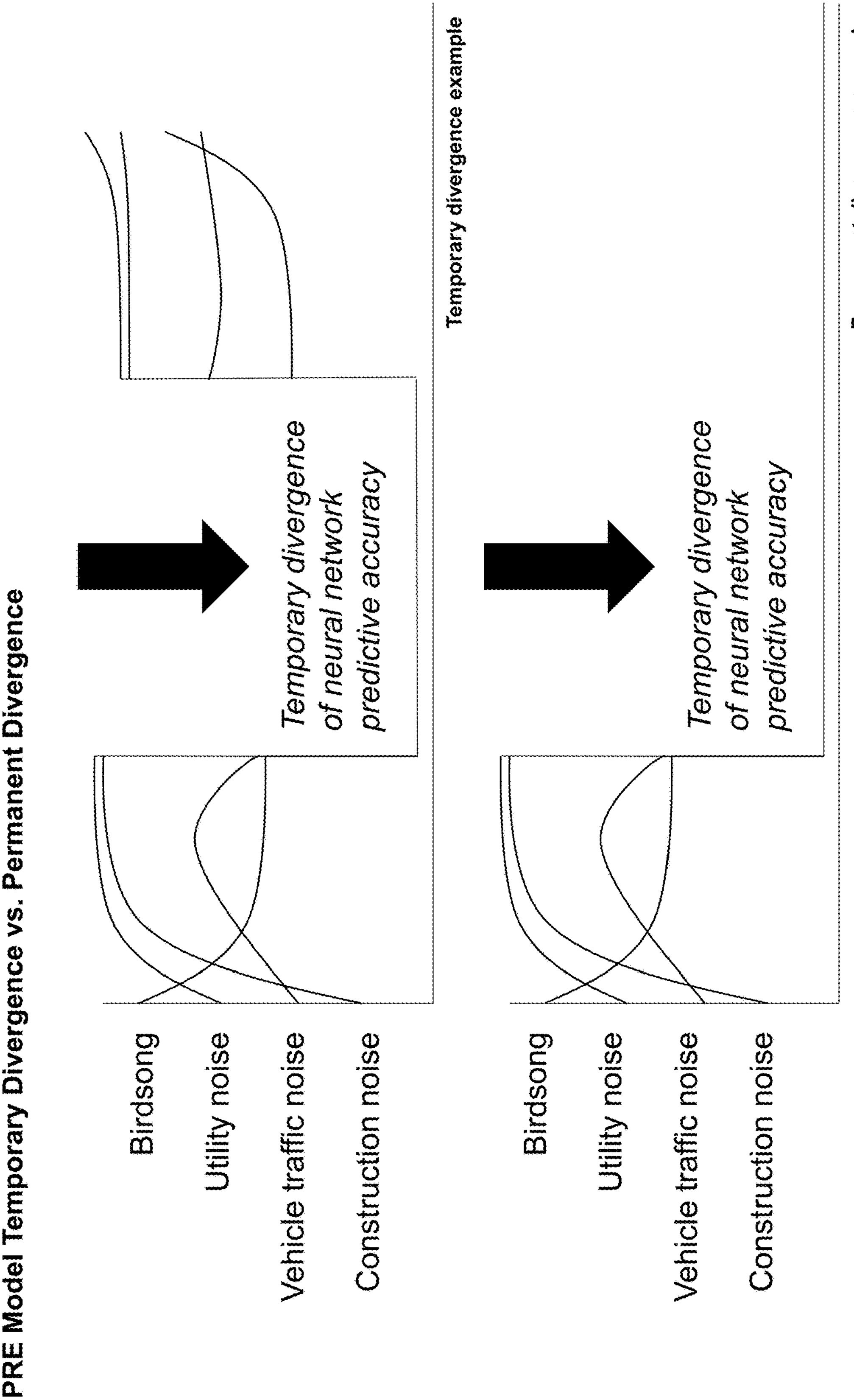
Fig 27. PRE Model Temporary Divergence vs. Permanent Divergence

Fig 28. PRE Model Performance Peaks and Plateaus

Model Accuracy Divergence "Peak"

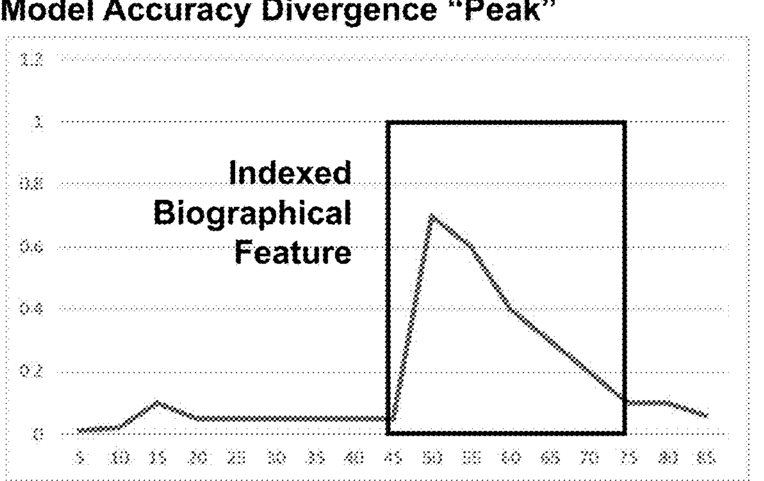

Temporary life event changed the classification quality of a trained neural network model.
Over time, without retraining model, the classification quality increased as the end user's actions re-aligned to training data.

Analysis: A temporary change in the end user's habits and patterns.

Model Accuracy Divergence "Plateau"

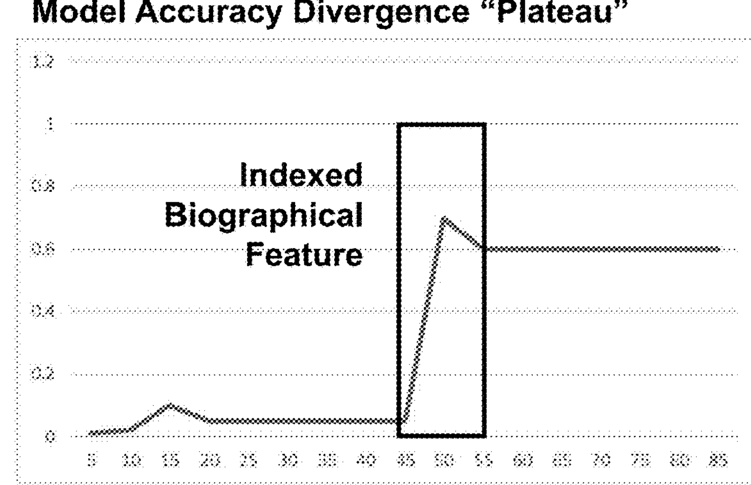

Permanent life event changed the classification quality of a trained neural network model.
The classification quality of the model never returned.

Analysis: A permanent change in the end user's habits. A new model must be developed.

Fig 29. PRE Models Divergence Over a Lifetime

Viewed over a lifetime, these divergences provide a visual index of eras of significant change.

As context changes, old neural network models cease to function and new neural networks require data acquisition to learn the new environment. These periods of transition and the valleys between the peaks provide insight into the areas of greater emphasis and potential interest in a biographical history.

- Applied toward indexing large datasets, model 'failure' through accuracy divergence provides a means of data indexing to support retrieval and interaction.
- Concurrent divergence (multiple factors changing / degree of change) provides greater insight into the degree of human interest into the data.

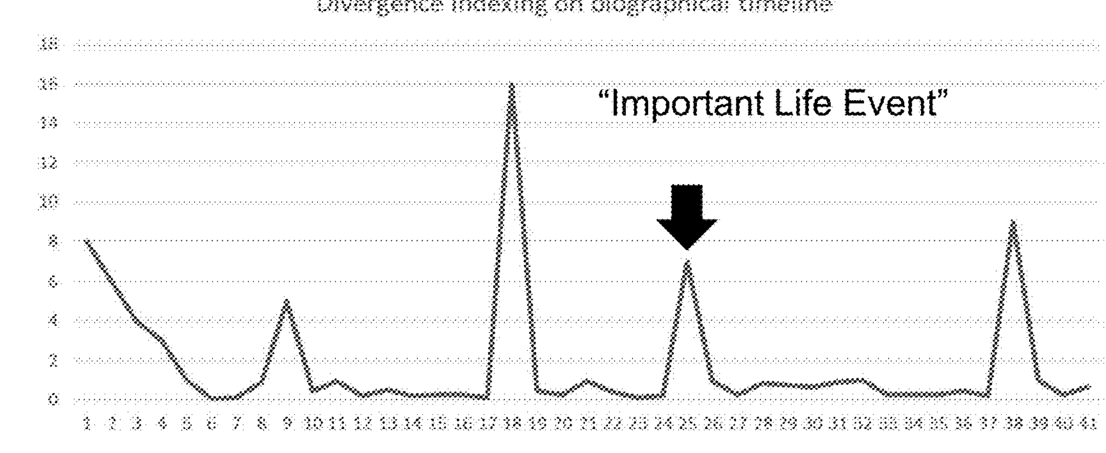

Aggregated divergence over a lifetime

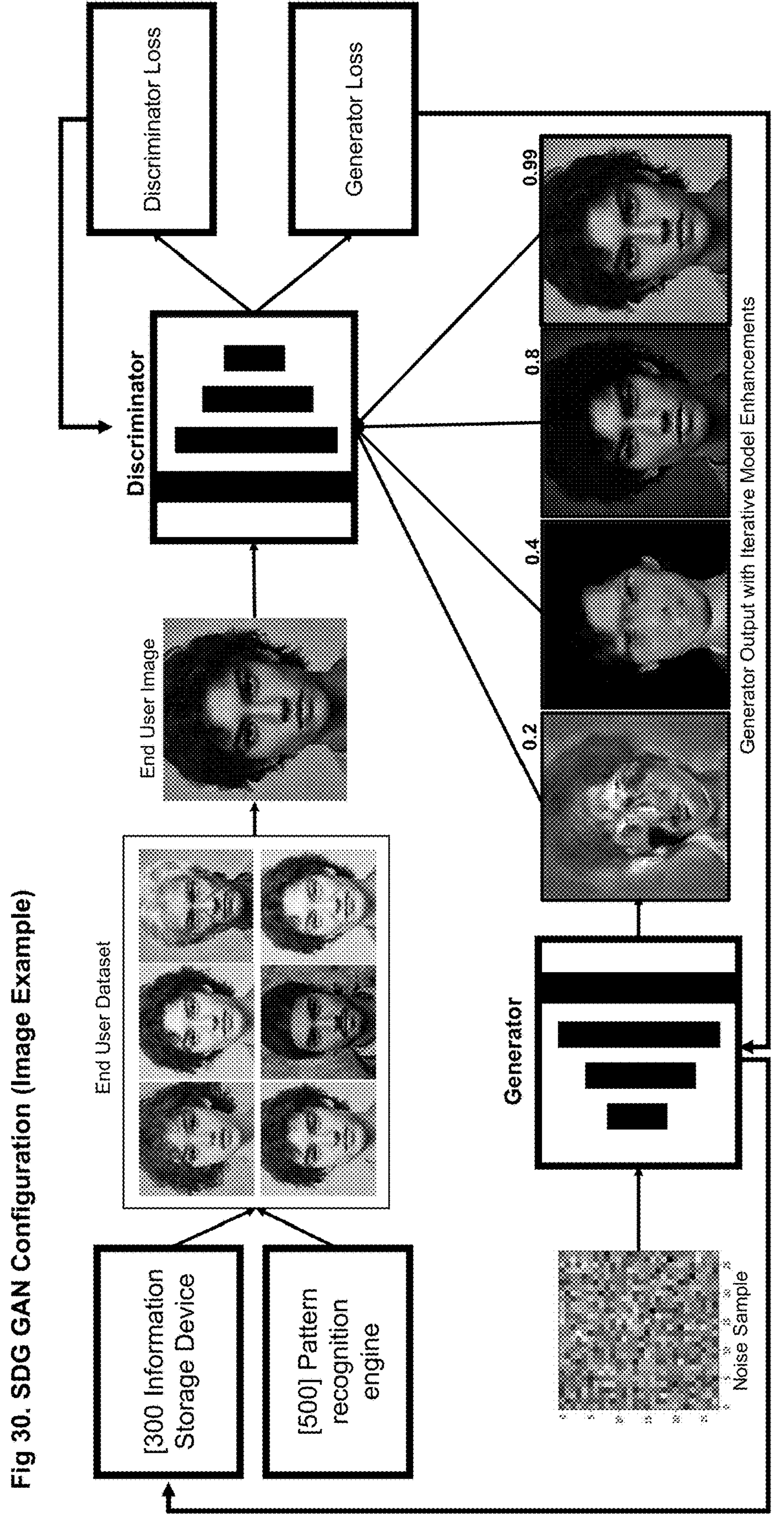
Fig 30. SDG GAN Configuration (Image Example)
[300 Information Storage Device
[500] Pattern recognition engine
End User Dataset
End User Image
Discriminator
Discriminator Loss
Generator Loss
Generator
Noise Sample
0.2
0.4
0.8
0.99
Generator Output with Iterative Model Enhancements
Results back propagation

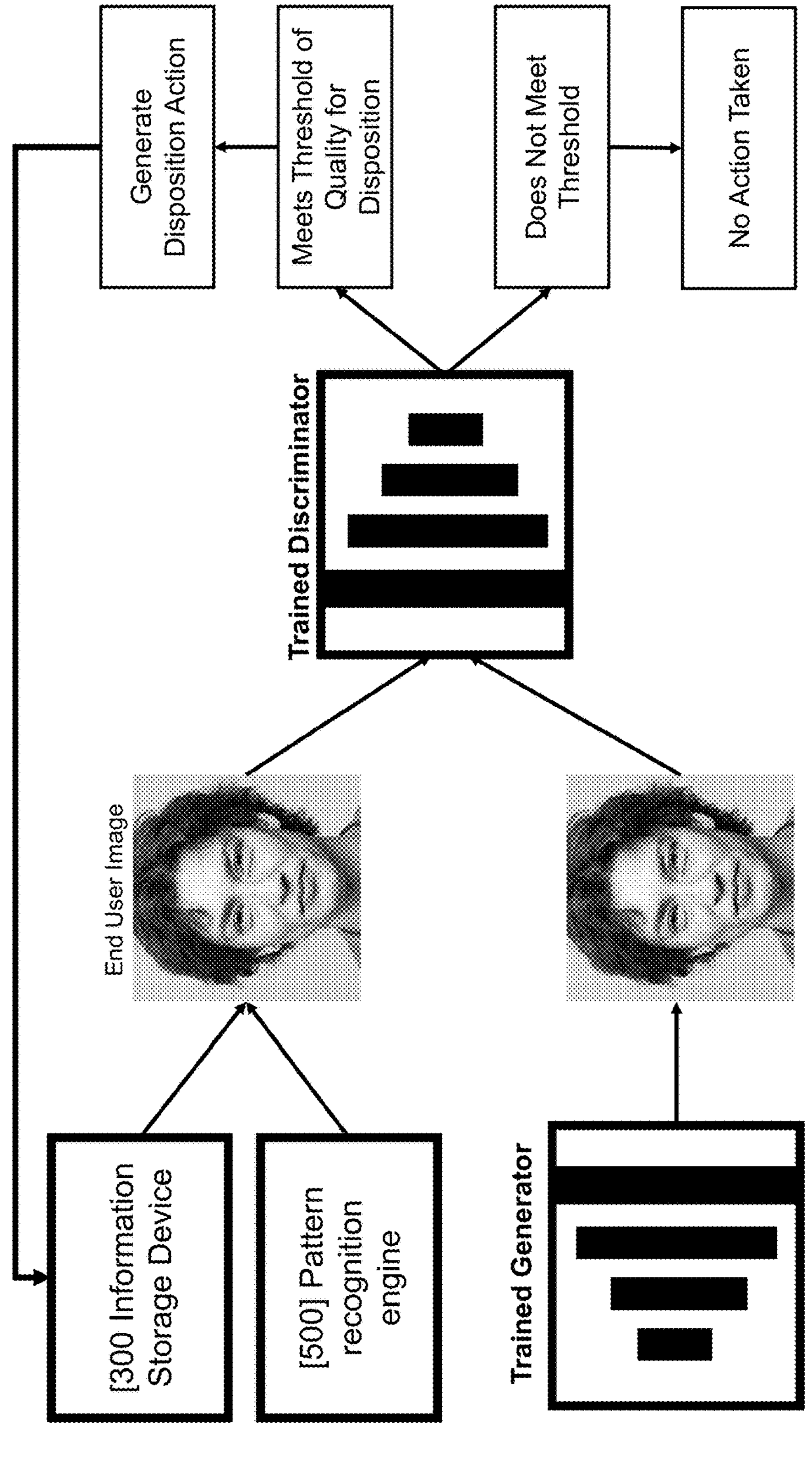
Fig 31. SDG Data Disposition

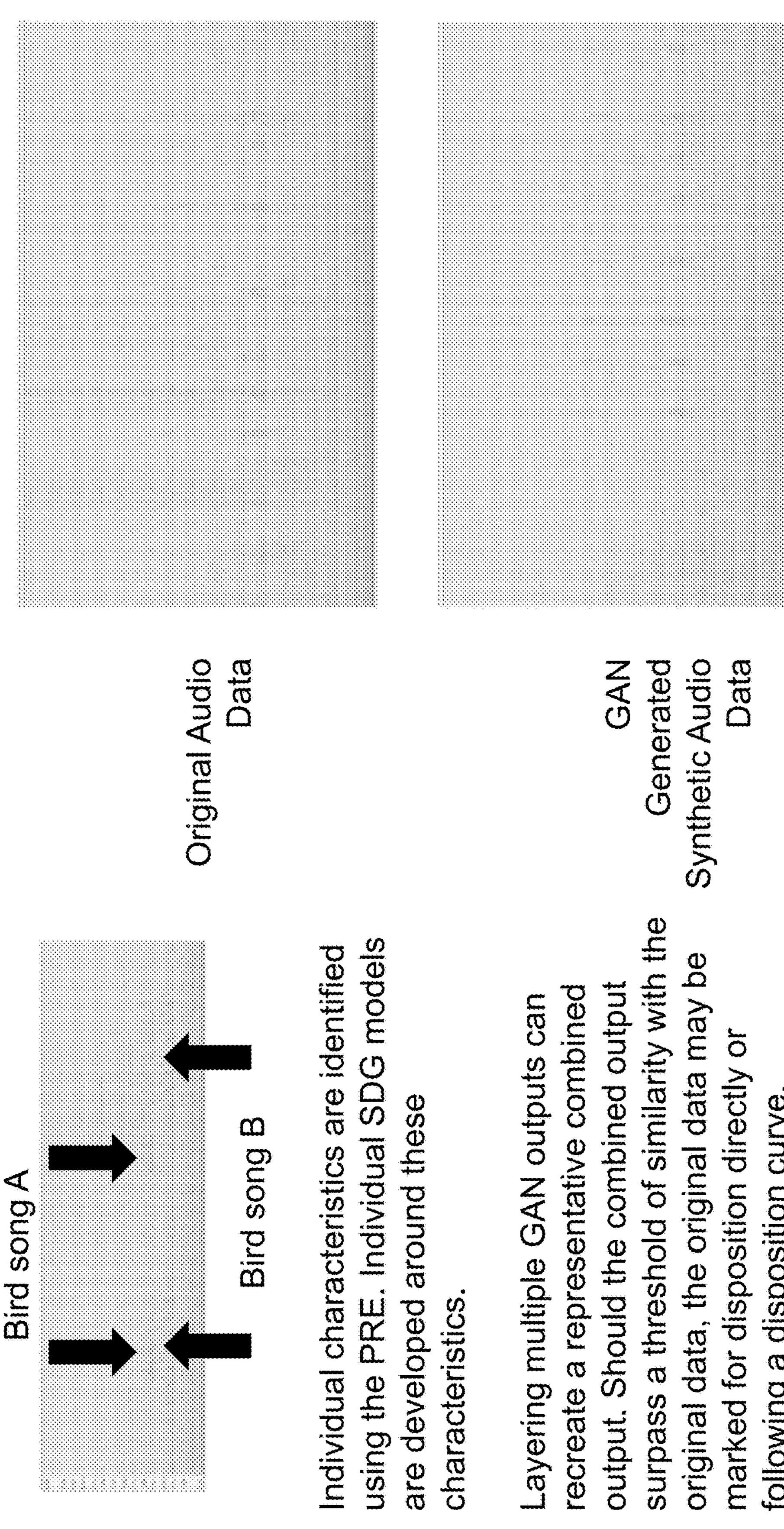
Fig 32. Synthetic Data Layering / Recombination of Multiple GAN Models
Bird song A
Bird song B
Individual characteristics are identified using the PRE. Individual SDG models are developed around these characteristics.
Layering multiple GAN outputs can recreate a representative combined output. Should the combined output surpass a threshold of similarity with the original data, the original data may be marked for disposition directly or following a disposition curve.
Original Audio Data
GAN Generated Synthetic Audio Data Fig 33. SDG-ISD Disposition Slopes
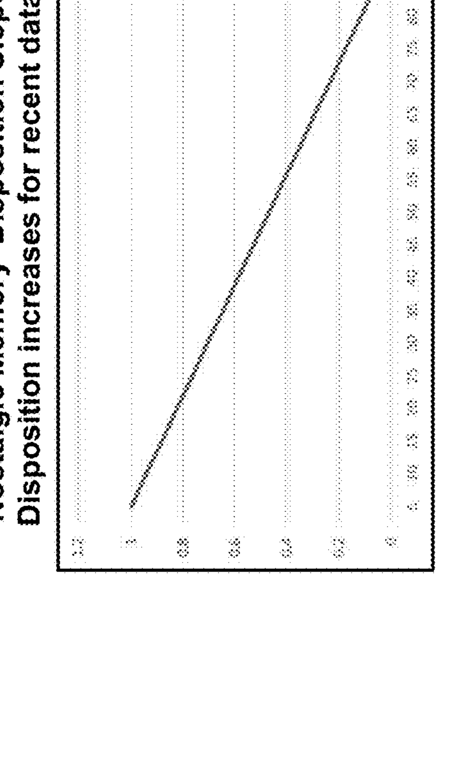
'Perfect Memory' Disposition Slope
No disposition of original data
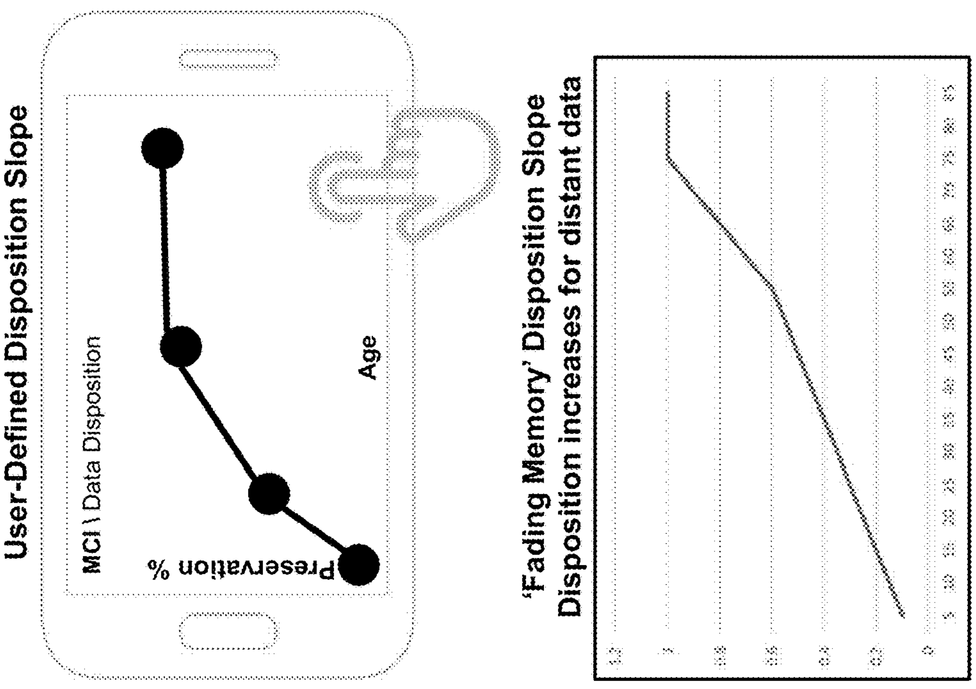

Fig 34. PSE Block Diagram
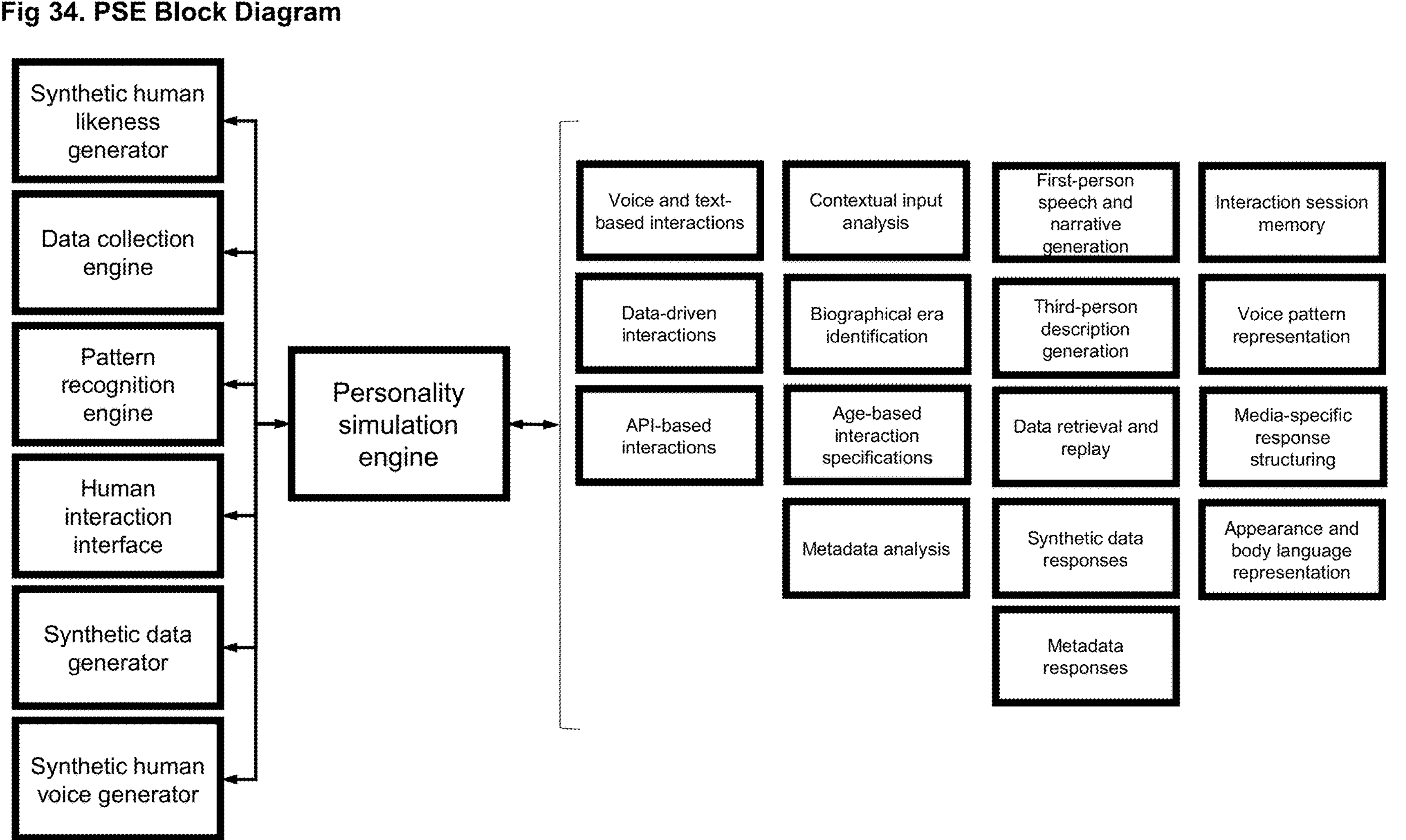

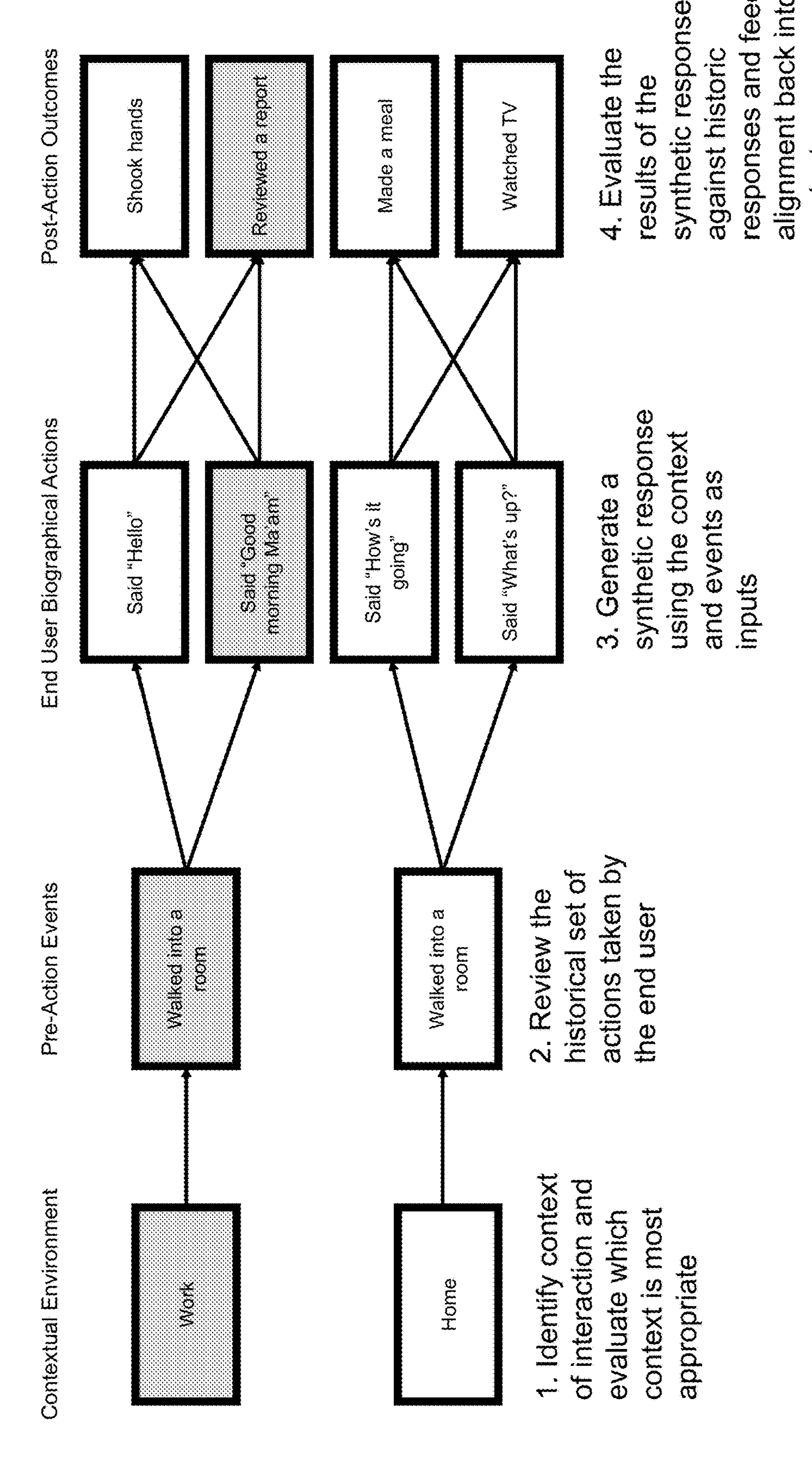
Fig 35. Contextual identification and search
Contextual Environment
Pre-Action Events
End User Biographical Actions
Post-Action Outcomes
Work
Walked into a room
Said "Hello"
Said "Good morning Ma'am"
Shook hands
Reviewed a report
Home
Walked into a room
Said "How's it going"
Said "What's up?"
Made a meal
Watched TV
1. Identify context of interaction and evaluate which context is most appropriate
2. Review the historical set of actions taken by the end user
3. Generate a synthetic response using the context and events as inputs
4. Evaluate the results of the synthetic response against historic responses and feed alignment back into context

Fig 36. PSE Historic Response Formulation
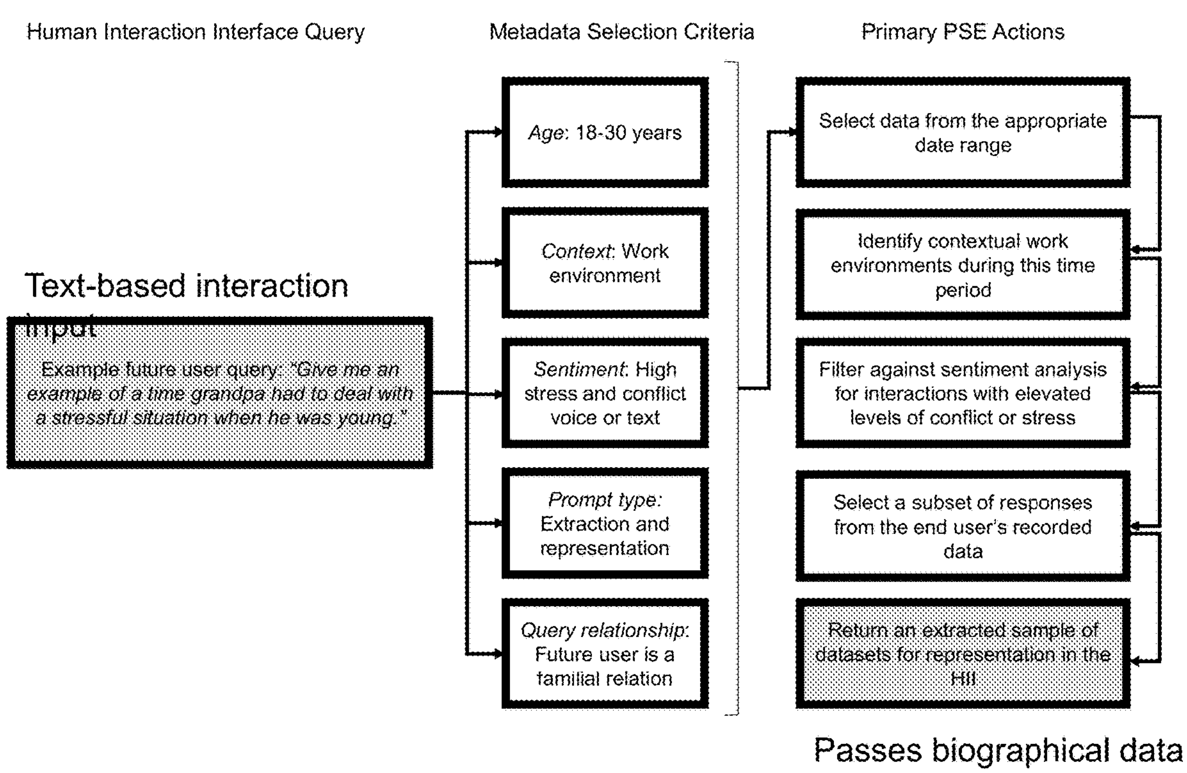

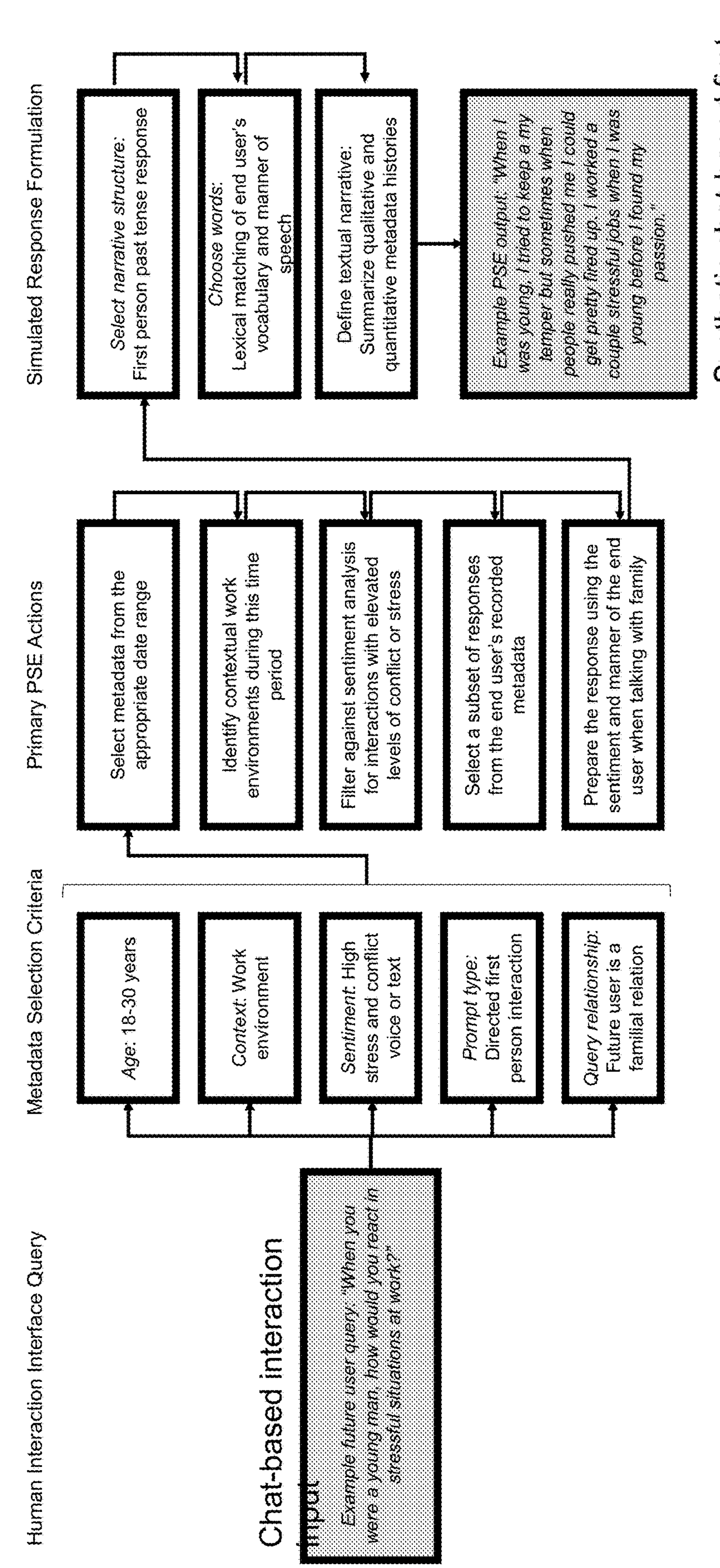
Fig 37. PSE Synthetic Response Formulation

Figure 38:
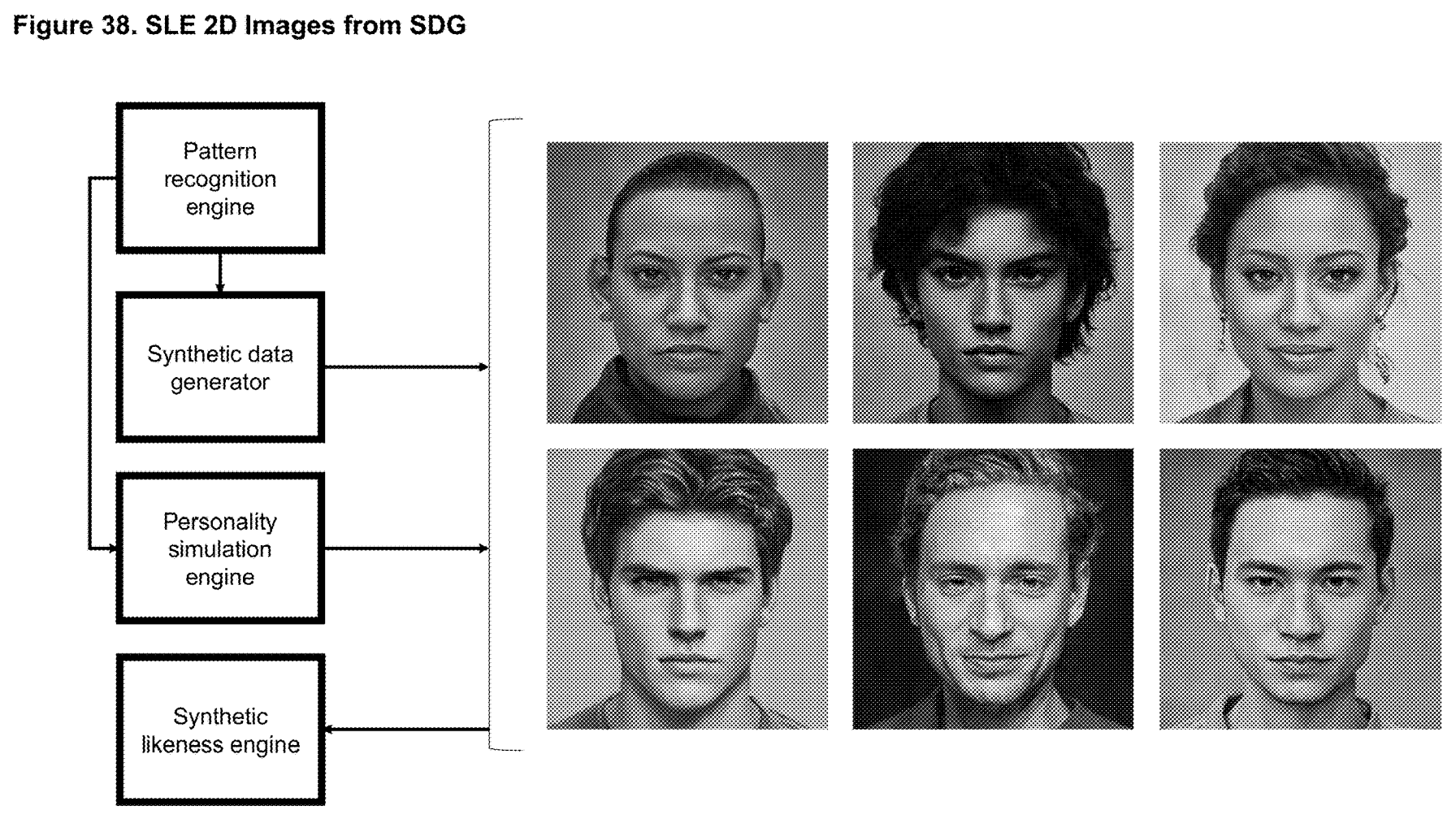

Figure 38. SLE 2D Images from SDG

Pattern recognition engine

Synthetic data generator

Personality simulation engine

Synthetic likeness engine

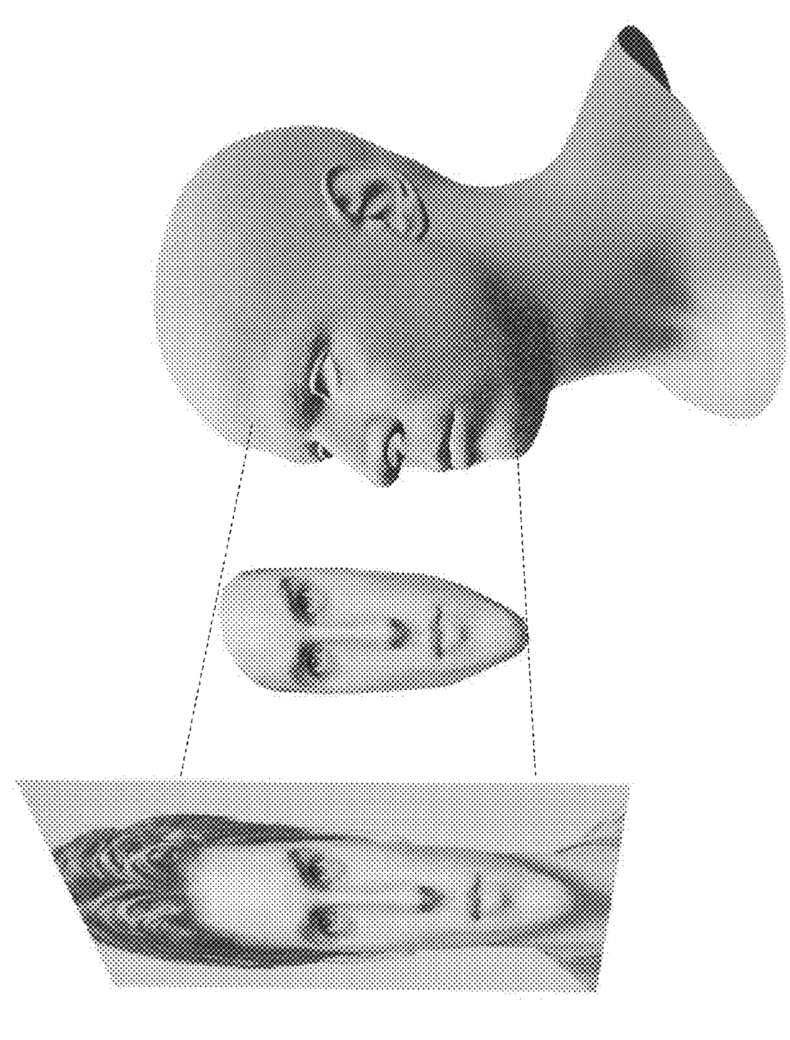
Figure 39. SLE 3D Model and Image Mapping

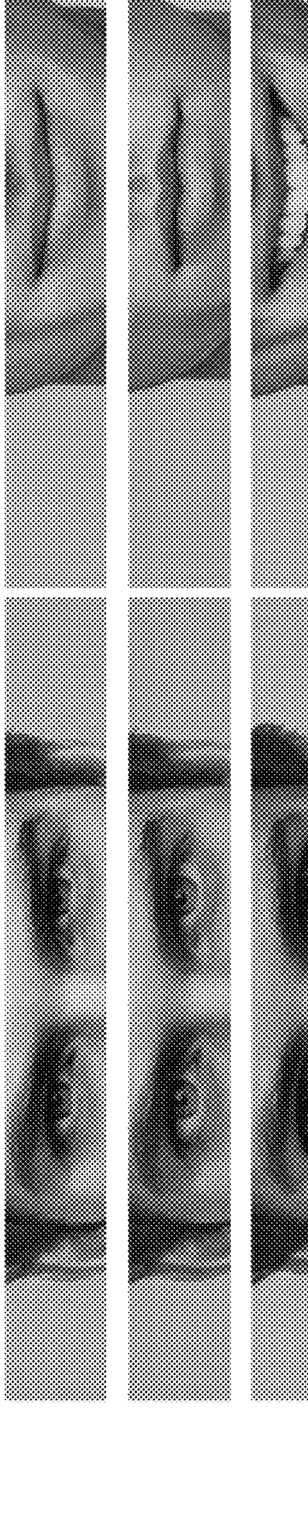
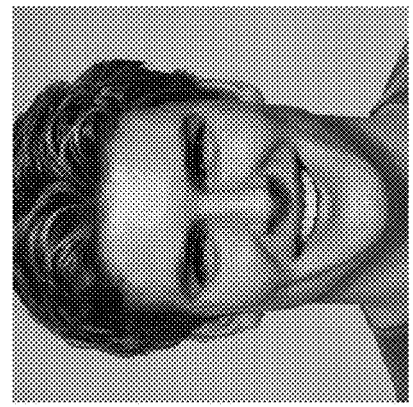
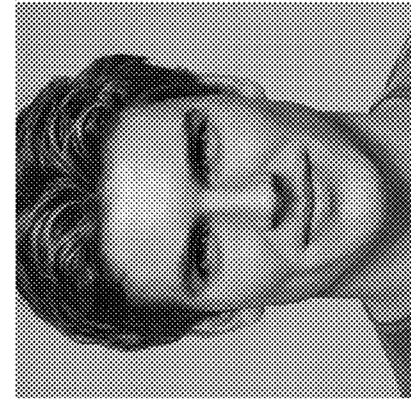
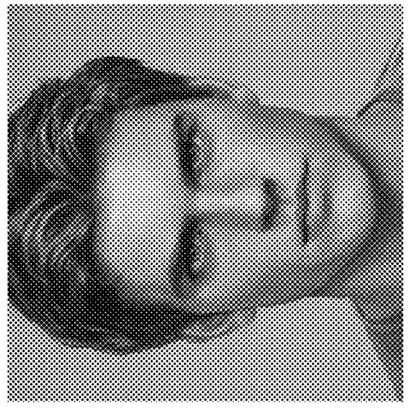
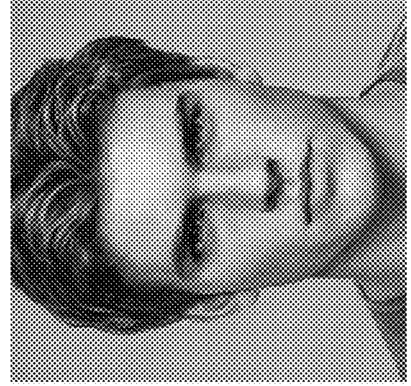
Figure 40. SLE Parameter Adjusted Micro-Expressions Fig 41. HII Block Diagram

Figure 42. HII Virtual Avatar Visualization

Figure 43. HII Virtual Avatar Interactions
Single Avatar Interaction
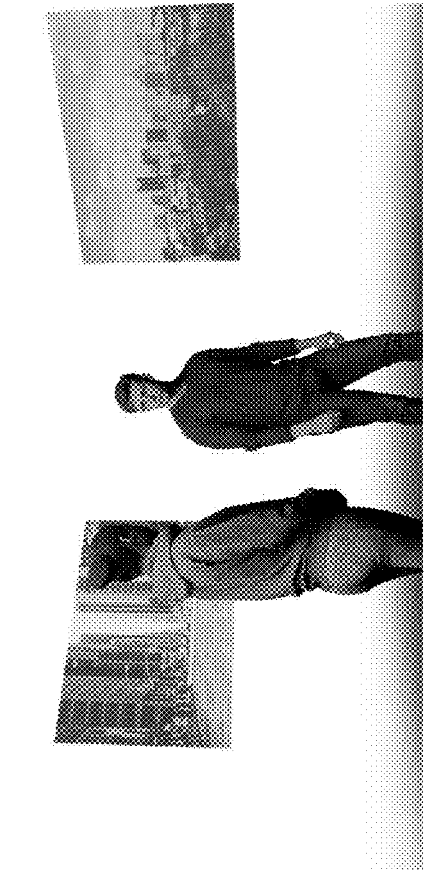
Multi-Avatar Interaction

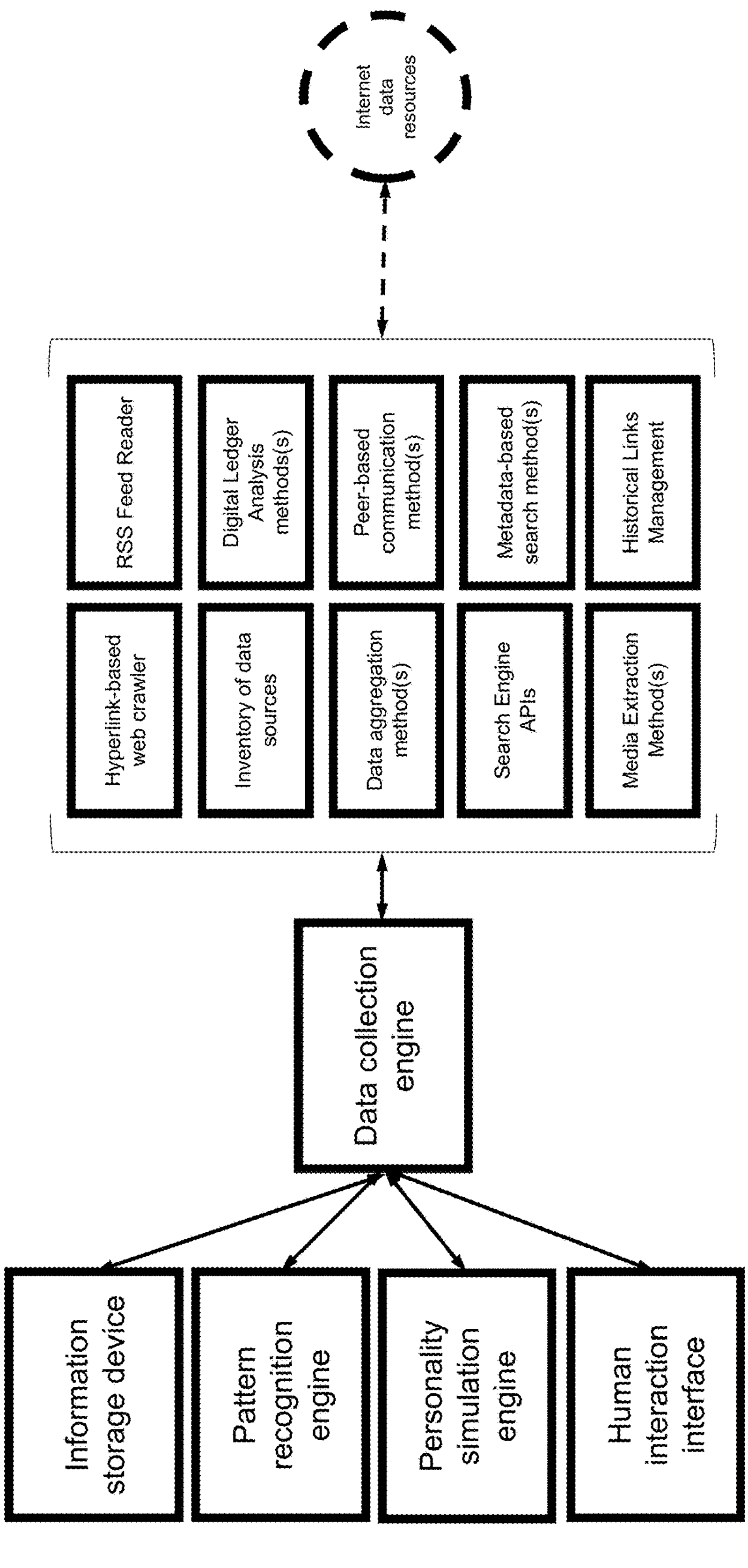
Fig 44. DCE Block Diagram

Fig 45. Indeterminate Adaptation of System State through Future User Interaction
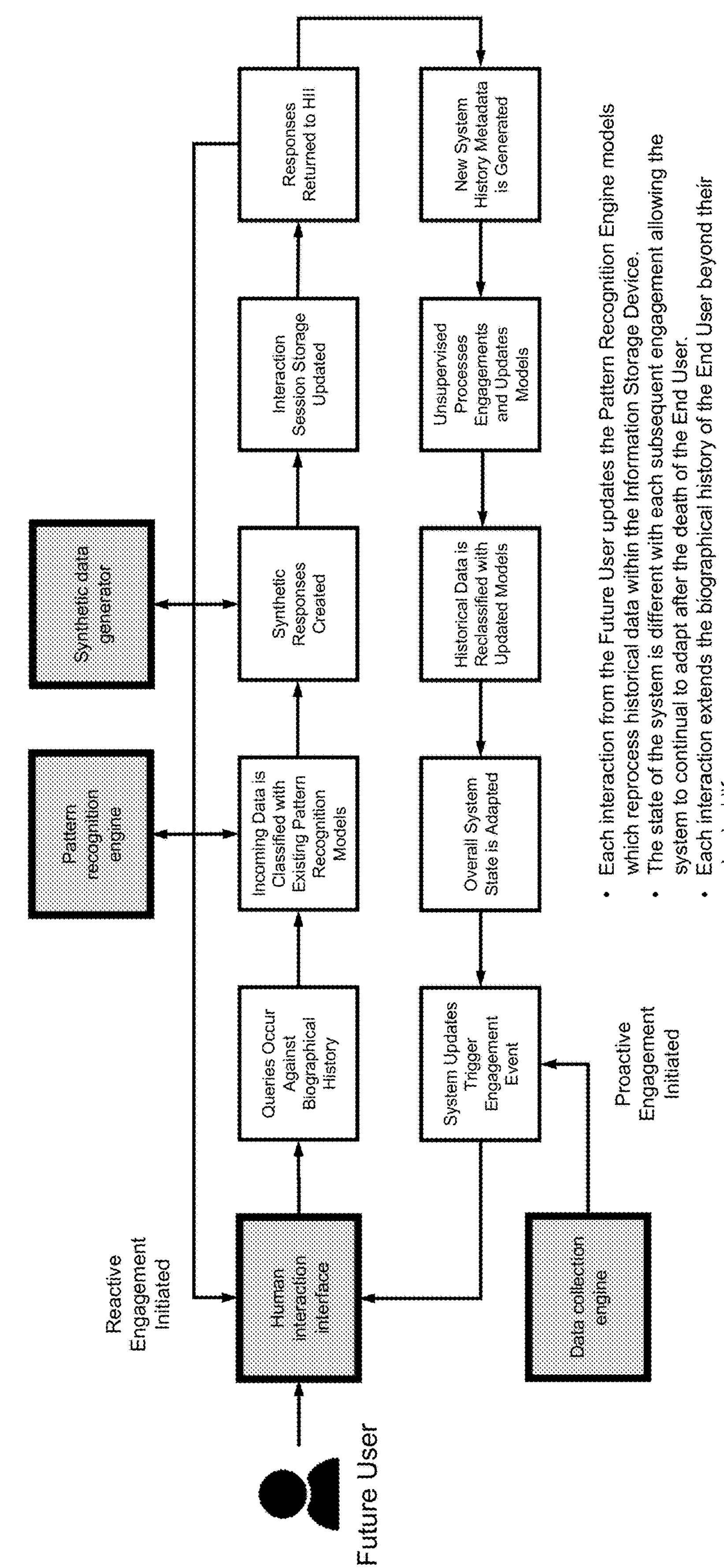

SYSTEM AND METHOD FOR CAPTURING, PRESERVING, AND REPRESENTING HUMAN EXPERIENCES AND PERSONALITY THROUGH A DIGITAL INTERFACE

FEDERALLY SPONSORED RESEARCH

Not Applicable

SEQUENCE LISTING OR PROGRAM

Not Applicable

TECHNICAL FIELD OF THE INVENTION

The present invention relates generally to a system and method to capture and interact with a comprehensive digital record of an individual's biographical history by means of a synthetic model of their personality. More specifically, the present invention relates to a system and method to capture and interact with a comprehensive digital record of an individual's biographical history and produce a synthetic model of their personality where the captured biographical history is a detailed record of this individual's actions, interactions, and experiences over a period which may span decades of their lifetime and the synthetic personality model presents an interactive interface which mimics the behavioral patterns, triggers, and characteristics of the individual as a means of representing tangible and intangible aspects of their individual nature and identity.

BACKGROUND OF THE INVENTION

The preservation of individual human characteristics has been a dominant social and cultural activity from pre-history to present day. Conscious knowledge of one's physical mortality and subsequent death prompt humans to develop or adopt social, technological, and ideological systems to overcome the emotional and psychological impact of this certainty. Conscious acts of self-preservation have been employed to preserve some fraction of an individual's identity into more durable media. Ideological and religious beliefs, held by most humans throughout recorded history, provide a conceptual framework which often includes models of posthumous preservations of self as a 'spirit' or 'soul'. Technology methods have been created to measure and translate human life to encoded messages for storage and transmission. Constructed social systems and laws have defined how one's property, including likeness and intellectual property, may be protected and passed down to subsequent generations.

In efforts to capture, represent, temporarily preserve, and share an artifact of one's personal identity, humans have employed a variety of representation techniques including but not limited to language, painting, architecture, storytelling, literature, recordings, digital data storage, magnetic, molecular, and biological data encoding. Such methods and media have been used to capture a range of individual features; the tangible nature of a person, such as their biology, physicality, genetics, and appearance, as well as representations of their actions throughout various periods of their life, and intangible or volatile characteristics, including their opinions, personalities, thoughts, experiences, and memories.

This universal drive toward self-preservation through representation, as opposed to biological reproduction, carries evolutionary advantages in the form of intergenerational knowledge transfer. Generally, the more data that can be preserved, the higher fidelity of that information, and the greater the longevity of these artifacts, the more beneficial it has been to subsequent generations. Modern humans frequently reference and celebrate preserved artifacts thousands of years old, inferring great knowledge of about our origins, identities, predecessors, and the nature of our changing environment. The preservation and sharing of an individual's experiences and knowledge may be considered, due to its ubiquity across time, geography, and culture, an adaptive and positive evolutionary trait for our species.

Yet despite the inherent value of this preservation, most individuals are unsuccessful in leaving behind any significant artifacts of their identity. While a small number of individuals are represented in historical record, most humans leave behind no lasting trace of themselves. Nearly all humans who have lived and died do so anonymously, their belongings and memory passed down temporarily before being lost within just a few decades or generations. For the subset of humans who have some records of their existence, many records only contain basic summary biographical information such as names, dates of birth, relations, and professions. Comprehensive and durable self-representation remains an unresolved human challenge till this day.

Representation faces numerous hurdles in terms of completeness, abstraction, encoding, durability, representation, and scope. All such methods of capturing human biographical histories or identities face the dual challenges of completeness of representation and scope. Representing a tangible event requires significant abstraction which often fails to adequately capture an accurate or comprehensive record of events.

Historically, manual (human-made) methods of representation (i.e. arts and crafts) have been subject to distortion due to the methods applied, skill of the creator, intentional misrepresentation, failure of memory, and the limitations of the medium to name just a few issues. The skill required to create such records manually paired with the demand for such skills made lasting representations rare and largely the domain of the affluent who could afford to commission and preserve such records from antiquity. More recently, mechanical (digital) methods introduced an objective means of capturing and representing experience with a higher degree of fidelity within a limited spectrum. Mechanically and digitally encoded methods preserve specific types of physical events (change) into a medium which may then decoded to allow these experiences to be recreated in the future; sound is captured by the microphone and then recreated by the speaker as light images are captured by the sensor and recreated with the display screen. Using such methods, it is possible to record limited representations of specific events for recreation at some future time. By applying a multiplicity of recording methods which capture a diversity of local actions and environmental characteristics (sound, light, motion, temperature, etc.), an objective and detailed biographical record can be created of an individual. The higher the fidelity of the recording mechanism, the more calibrated such devices are to human physical senses, the more accurate the encoding and storage of this history.

While mechanical methods increase the recognizability of the event, their representations are also challenged by scope. Objective sensor-based recording devices such as microphones, cameras, and sensors have more recently enabled the objective capture and representation of experiences using physical and digital media. The advent of such devices represents a dramatic shift in the potential for human self-representation within a storage medium. However, deployed within smart personal devices today they still are not configured to capture a comprehensive set of data and resort to brief, fractional capture methods. For example, if a person alive today was to take 10,000 photos within their lifetime, each photo may capture only 1/100th of a second. Compounded, these 10,000 photos would represent only 100 seconds of lived experience, translating to only approximately 1/25 millionth of a lifetime. Despite their fidelity, the implementation of digital devices still is only capturing a miniscule portion of the complete human experience.

Capturing a comprehensive record of a single individual by these means remains highly challenging. Where a brief digital record of an image, video, or audio clip may be easily reviewed, it is difficult presently to review large volumes of such data. Months, years, or decades of continual recordings become nearly useless because the subjective value of much of its contents is low and efforts to review such large representations highly time-consuming. A month of audio would require a month of continual listening by a person to identify the representation of any valuable events. Multiplied by the potential of recording from dozens of sensors or devices simultaneously to expand the scope of such a capture, it becomes impossible for any person to view or interact with the recorded data of another person. Due to such obviously limitations, the value of data may begin to dimmish without a sophisticated means of summarizing vast amounts of data.

Digital recording methods also suffer from many other challenges. A primary challenge is capacity of media. All recording media are limited by the capacity to store information, whether it is the canvas and the skill of a painter, or the resolution of a digital image saved to a hard drive, media is physical in nature and thus defined by limits. While larger digital storage devices are produced each year, they still have limits with how data is structured, in files and folders, and in their ultimate capacity. As such, data must be split across multiple storage devices when it gets too big. As data grows, the processing power required to identify and retrieve data grows as well.

Data storage fidelity and media decay are also major challenges today. Digital storage devices are only rated to store information for several years. Because of the vast volume of information that can be stored within a relatively small physical medium, natural decay within storage media may occur resulting in the corruption of data on storage devices. Once media decay occurs, it is common that digitally stored datasets can be lost in part or in full.

Current methods of digital encoding of information, which provide a logical structure to stored data, can also compound the impact of data corruption. Encoded data uses mathematical formulas to compress information to optimize storage space but is also used to identify which data relates to location, color, and numeric information within a digital file. When a single byte (one character) of information in an encoded format is lost, an entire file can be corrupted and rendered unrecoverable for common users. Digital decoding methods are sometimes able to verify when this occurs but often cannot recover from such losses. This issue significantly impacts compressed or cryptographically protected files.

Changing technologies and protocols for data storage are also responsible for a major loss of data. Changing standards and the loss of mechanical systems that can encode and decode old methods are expected to push the 20th and 21st centuries into a historical digital dark age whereby much of the knowledge generated will be lost and unrecoverable to future generations. Unlike traditional physical means of representation (painting, sculpture, etc.) which can last many decades, centuries, or even millennia in some cases, digital representations can be lost rapidly and permanently through technological change, becoming difficult or impossible to decode and represent.

Digital data is also subject to corruption by manual means by bad actors. Digital media is easily manipulated and faked to simulate events which did not happen. Current storage protocols do not implement methods for enforcing the authenticity of recorded information. Cryptographically enabled methods do exist and are used commonly on signals communications and distributed digital ledger technologies to store transactions, such as blockchain technologies, but are not commonly utilized to ensure or measure the authenticity of extensive datasets such as recorded experiences. While they may restrict access to a file (encryption) or confirm that it has not been further manipulated (hashing), they do not verify that the file is an authentic representation of an experience or event.

To overcome the physical capacity limits and integrity issues related to local data storage, network accessible computer systems may be used. Copies of information are created and transferred over the internet and stored on external storage servers. This method creates one or more digital copies of personal information and stores them at offsite data centers. However, this method provides a false limited control over several aspects of the data. Data storage must be licensed at greater costs as data volumes increase. License agreements which underline the responsibilities of the data storage company are subject to change without notice. Companies and storage sites often shut down or are acquired by third parties. Passwords, cryptographic keys, and access credentials to retrieve data are often lost resulting in unrecoverable data. Personal data on such platforms is also accessed frequently by unauthorized bad actors and stolen or encrypted as ransom. Since such services are relatively new within society, there is no indication that their usage will result in better data retention and fidelity over the long run and can conversely result in rapid loss through natural or human-made disasters. The technologies used by these providers is further subject to the same challenges identified above (loss, corruption, etc.).

Presently, some human experience and activity data is being recorded by applying several devices and utilizing numerous software applications, some of which save data locally on media storage devices while others which use distributed storage systems accessible by network. Increasingly, applications apply networked services as their primary method of data storage resulting in a significant decentralization of data. Image data, emails, biometric information, financial information, entertainment, phone calls, and calendars, to name just a few types of digital activities, are all produced for and stored on separate decentralized computing and storage systems. Each platform is subject to extensive license agreements which prevent the centralization of this data. Some of these systems permit download of this information but do so in uncommon encoding methods or in ways which are inaccessible to the average technology user. As more services are brought online daily and accessible exclusively over network devices, personal experience data faces greater decentralization, fragmentation, and potential for loss. For current and future generations, it will be difficult to impossible to repatriate this information to build a cohesive narrative of human experience.

One of the paramount issues in digital storage is the volume of data that would be generated in comprehensively capturing the life of a human. In addition to the media and communications generated presently, this invention adds numerous other sensor types which would reasonably expect to be in the range of terabytes, petabytes (1,000 terabytes), or zettabyte (1,000 petabytes). Such storage has historically and is presently cost prohibitive for users to access directly or through networked services. Presently, there is not enough digital storage in existence to capture comprehensive data on more than a small fraction of the human population.

Large data volumes are also difficult to search and to review by any human. A lifetime of data of one human would logically take at least a lifetime for another human to experience in its entirety if played back at normal speed. The value of such an extensive reserve of information is limited unless one can apply a means of summarizing and indexing such information to support its identification and playback.

All existing data storage methods fail to adequate summarize and abstract recorded biographical data into representations of personality. By applying pattern recognition methods against a comprehensive dataset, intangible human characteristics can begin to be captured and extracted through the analysis of this data. Features of a person's identity can be derived from the patterns of their recorded actions and reactions to environmental stimuli. Metadata on an individual's response patterns to stimuli represents their 'temperament' as it is demonstrated over periods of their life, while changes in such patterns represent 'growth' of the individual. Through the analysis of the patterns occurring in these records, it is possible to objectively analyze and deduce a comprehensive record of a person's preoccupations, interests, objectives, beliefs, fears, desires, and their psychological state, aspects which have previously in history relied on the biased and fallible recollections of the subject individual.

These myriad data challenges have to date prevented humans from implementing a reliable means of gathering a comprehensive dataset which forms an accurate dataset of their biographical experiences. This system will apply novel methods of data collection, management, and dissemination which, applied in sequence and in parallel, will provide a comprehensive biographical narrative and summaries of this data which may be used to interpret the personality traits of a subject human.

Hence, an improved system for data collection, storage, optimization, classification, dissemination, representation, summarization, and interaction will be advantageous to individuals who wish to preserve and share a maximum amount of information about their lives within their lifespan or following their death. The method taught by the present invention will be a significant enhancement over any other method of autobiographical self-preservation of individuals living or dead that is available.

SUMMARY OF THE PRESENT INVENTION

This method and system of the present invention breaks down into three primary parts: data collection and storage, data classification and synthesis, and interaction via a virtual avatar.

The modules in this device include a multimodal sensor device array, digital activity monitoring software running on existing commercial products, and information storage devices using existing digital media storage methods and systems. These modules are augmented using a novel configuration of neural network-based processes, including a pattern recognition engine, synthetic data generator, and synthetic personality, likeness, and voice engines. A set of human interaction interfaces and a data collection engine provide a means of interaction between the biographical history and personality and with external users of the system.

There are several specific methods and processes within this novel system which are believed to be the most unique and most likely to support the patentability of the system. These processes resolve the shortcomings of the existing state of the art identified above.

Continuous and diverse sets of data are gathered via a range of hardware and software devices. This multiplicity of sources provides the volume of data required for the training and operationalization of sophisticated neural network models without extensively relying on external and potentially biased training datasets.

Parallel neural network-based classification models are generated and applied to create a comprehensive biographical history through the production of descriptive metadata. The resulting metadata identifies and enriches the context of the individual's actions and experiences in a complex and dynamic environment.

The indexing of data through the observance of neural network divergence presents a means of identifying important moments and periods of change within extremely large and complex datasets. Performance divergence, especially when occurring across multiple data types, indicates that the individual's patterns and habits have changed relative to previously generated models. As divergence occurs, old models are no longer performant in analyzing and predicting the content of new data. By generating indexes for these specific moments of divergence, the system can identify, present, preserve, and share these events as a set of subjectively valuable data subset to optimize the search and review of biographical datasets.

Synthetic data generation, as a means of optimizing data storage, introduces processes of using neural networks to produce realistic data which represents biographical events. By comparing synthetic and original data and validating that generative models can surpass a user-defined level of authenticity, original datasets may be disposed to optimize data storage requirements without significantly inhibiting user experience.

The application of disposition curves to define data retention and disposition models change the rate of original data disposition based on its age and the relative accuracy of the synthetic data generation capabilities.

The representation of a human individual as the primary means of end-user interaction provides a universally understandable means of interfacing with a complex system and its large underlying datasets. The application of generative data processes to represent the original voice, appearance, and mannerisms of the subject human provides a means of highly recognizable self-representation.

While the objective of the present invention is to teach an overall novel system, these modules specifically differentiate this configuration of features and assist in making this invention novel and non-obvious in view of the prior art.

Definitions

"Application programming interface" or "API" is a means by which two or more computer systems or applications to communicate with via a defined protocol. A computer system that meets this standard is said to implement or expose an API. The term API may refer either to the specification or to the implementation.

"Application software" or "software" is a set of one or more programs designed to carry out operations for a specific application. Application software cannot run on itself but is dependent on system software to execute. Examples of application software include MS Word, MS Excel, a console game, a library management system, a spreadsheet system etc. The term is used to distinguish such software from another type of computer program referred to as system software, which manages and integrates a computer's capabilities but does not directly perform tasks that benefit the user. The system software serves the application, which in turn serves the user.

The term "app" is a shortening of the term "application software". It has become very popular and in 2010 was listed as "Word of the Year" by the American Dialect Society.

"Apps" are usually available through application distribution platforms, which began appearing in 2008 and are typically operated by the owner of the mobile operating system. Some apps are free, while others must be bought. Usually, they are downloaded from the platform to a target device, but sometimes they can be downloaded to laptops or desktop computers.

An "Avatar" is a recognizable, interactive, digital representation of the end user based on visual and auditory simulations that utilize end user data and metadata.

A "Biographical history" is a detailed or summary collection of recorded data and generated metadata describe with accuracy a variety of activities, interactions, and experiences of the end user over time.

A "digital HUB", "HUB", or "network hub" is a device that allows multiple computers to communicate with each other over a network. It has several Ethernet ports that are used to connect two or more network devices together. While switches send incoming data to a specific port, hubs broadcast all incoming data to all active ports.

A "Distributed ledger" is a means of storing data across multiple computation devices, called nodes, where there is no centralized owner or authority, and the rights to add data is controlled by a set of pre-defined rules. Participants in the network are sometimes rewarded with virtual currencies called 'coins' for performing validation functions.

"Electronic Mobile Device" is defined as any computer, phone, or computing device that is comprised of a battery, display, circuit board, and processor that is capable of processing or executing software. Examples of electronic mobile devices are smartphones, laptop computers, and tablet PCs.

An "End User" is the primary user of this invention whose life is being recorded and documented by the system.

A "Future User" is any permitted user who is accessing the invention through the Human Interaction Interface (HII) for the purposes of engaging with the biographical history or the simulated personality.

"GUI". In computing, a graphical user interface (GUI) sometimes pronounced "gooey" (or "gee-you-eye")) is a type of interface that allows users to interact with electronic devices through graphical icons and visual indicators such as secondary notation, as opposed to text-based interfaces, typed command labels or text navigation. GUIs were introduced in reaction to the perceived steep learning curve of command-line interfaces (CLIs), which require commands to be typed on the keyboard.

A "Ledger" is a means of storing data which uses cryptographic methods to validate the authenticity of the stored information. Typically, a set of data is used to generate a reproducible and unique digital code, known as a hash, which is appended to the next set of data recorded.

"Metadata" is any data generated which describes one or more characteristics of or within the recorded data of invention.

A "mobile app" is a computer program designed to run on smartphones, tablet computers and other mobile devices, which the Applicant/Inventor refers to generically as "a computing device", which is not intended to be all inclusive of all computers and mobile devices that are capable of executing software applications.

A 'Model" is a data categorization or generation script, code, or algorithm, typically configured as a neural network, capable of producing either generated data or metadata.

A "Neural Network" (also known as an artificial neural network or ANN) is a computational process whereby numerous inputs are accepted into a function (called the input layer), processed through a series of steps (called hidden layers), and resulting in one or more outputs (called the output layer). Neural networks commonly have activation functions which control the amplitude and form of the outputs.

A "Sensor" is an electronic means of capturing real-world events and interactions, such as physical interactions, electromagnetic radiation, or forces.

A "Simulated personality" is the tangible and intangible characteristics of the end user as may be identified through analysis of any of the available data within this invention. Personality traits are inferred through the identification of patterns identified within recorded data and metadata.

A "smartphone" (or smart phone) is a mobile phone with more advanced computing capability and connectivity than basic feature phones designed for person-to-person voice-based calls. Smartphones typically include the features of a phone with those of another popular consumer device, such as a personal digital assistant, a media player, a digital camera, and/or a GPS navigation unit. Later smartphones include all of those plus the features of a touchscreen computer, including web browsing, wideband network radio (e.g. LTE, 5G), Wi-Fi, 3rd-party apps, motion sensor and mobile payment.

"Synthetic Data" is any data which is created by a generative function or model which was not captured by sensors or generated by direct human interactions with technology.

"Training" is a process of refining the weights of neural networks by providing labeled or unlabeled data and evaluating the results. In an iterative fashion, the weights within the network are adjusted to optimize the output of the network.

A "User" is any person registered to use the computer system executing the method of the present invention.

A "web application" or "web app" is any application software that runs in a web browser and is created in a browser-supported programming language (such as the combination of JavaScript, HTML and CSS) and relies on a web browser to render the application.

"Wi-Fi", also spelled Wifi, WiFi, or wifi, is a local area wireless technology that allows an electronic device to exchange data or connect to the internet, commonly using 2.4 GHz UHF and 5 GHz SHF radio waves. The name is a trademark name and is a play on the audiophile term Hi-Fi. The Wi-Fi Alliance defines Wi-Fi as any "wireless local area network (WLAN) products that are based on the Institute of Electrical and Electronics Engineers' (IEEE) 802.11 standards". [1] However, since most modern WLANs are based on these standards, the term "Wi-Fi" is used in general English as a synonym for "WLAN". Only Wi-Fi products that complete Wi-Fi Alliance interoperability certification testing successfully may use the "Wi-Fi CERTIFIED" trademark.

BRIEF DESCRIPTION OF THE DRAWINGS

The accompanying drawings, which are incorporated herein a form a part of the specification, illustrate the present invention and, together with the description, further serve to explain the principles of the invention and to enable a person skilled in the pertinent art to make and use the invention.

FIG. 1 is an overall composition of the present invention.

FIG. 2 is an MSD Block Diagram of the present invention.

FIG. 3. is an MSD Device Schematic of the present invention.

FIG. 4. is an MSD Use Cases Examples of the present invention.

FIG. 5. Illustrates DAR API Connections to Hardware and Software of the present invention.

FIG. 6. illustrates DAR Data Type Examples of the present invention.

FIG. 7. illustrates DAR Features and Interface of the present invention.

Figure 8:
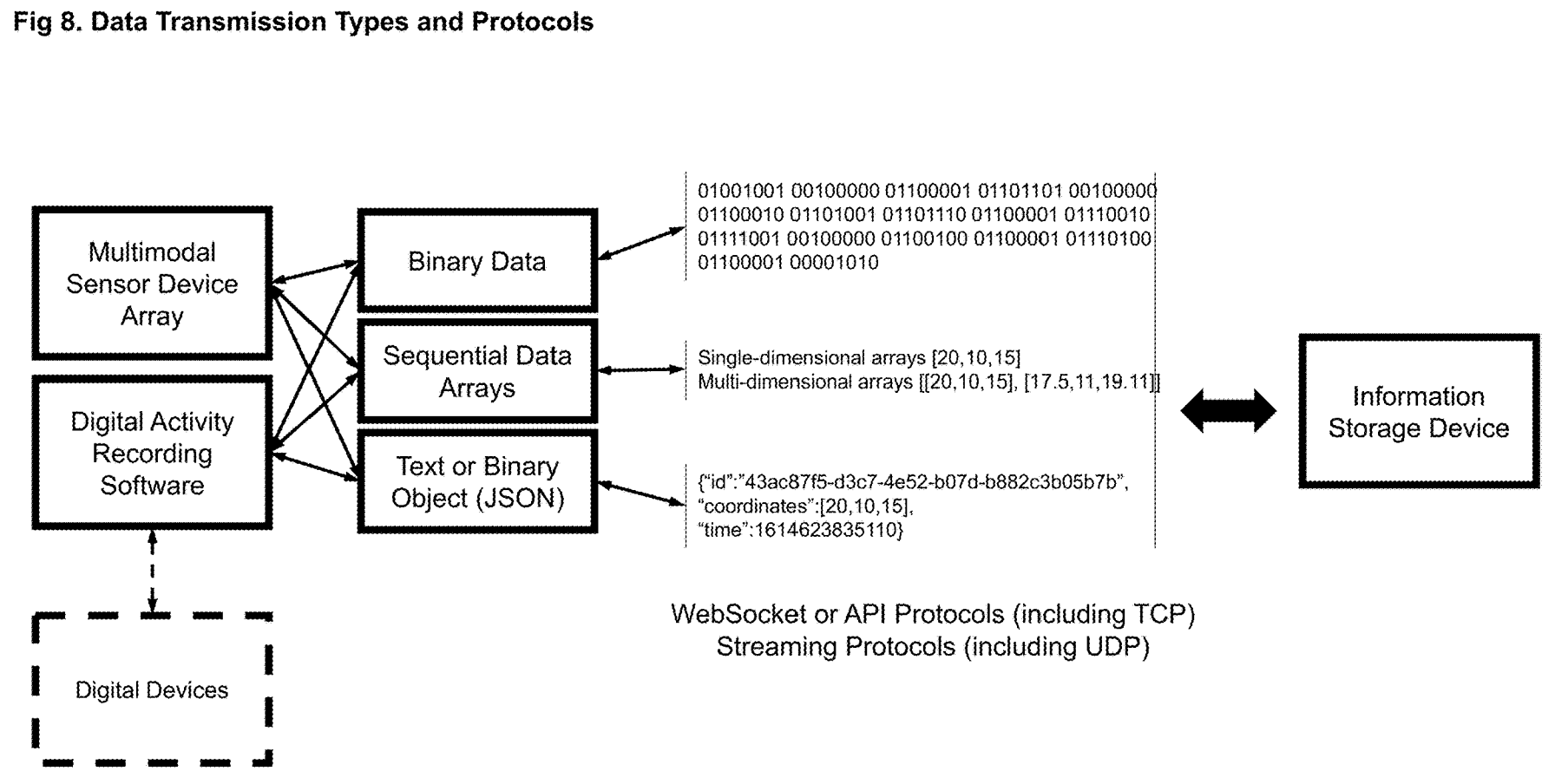

FIG. 8. illustrates Data Transmission Types and Protocols of the present invention.

Figure 9:
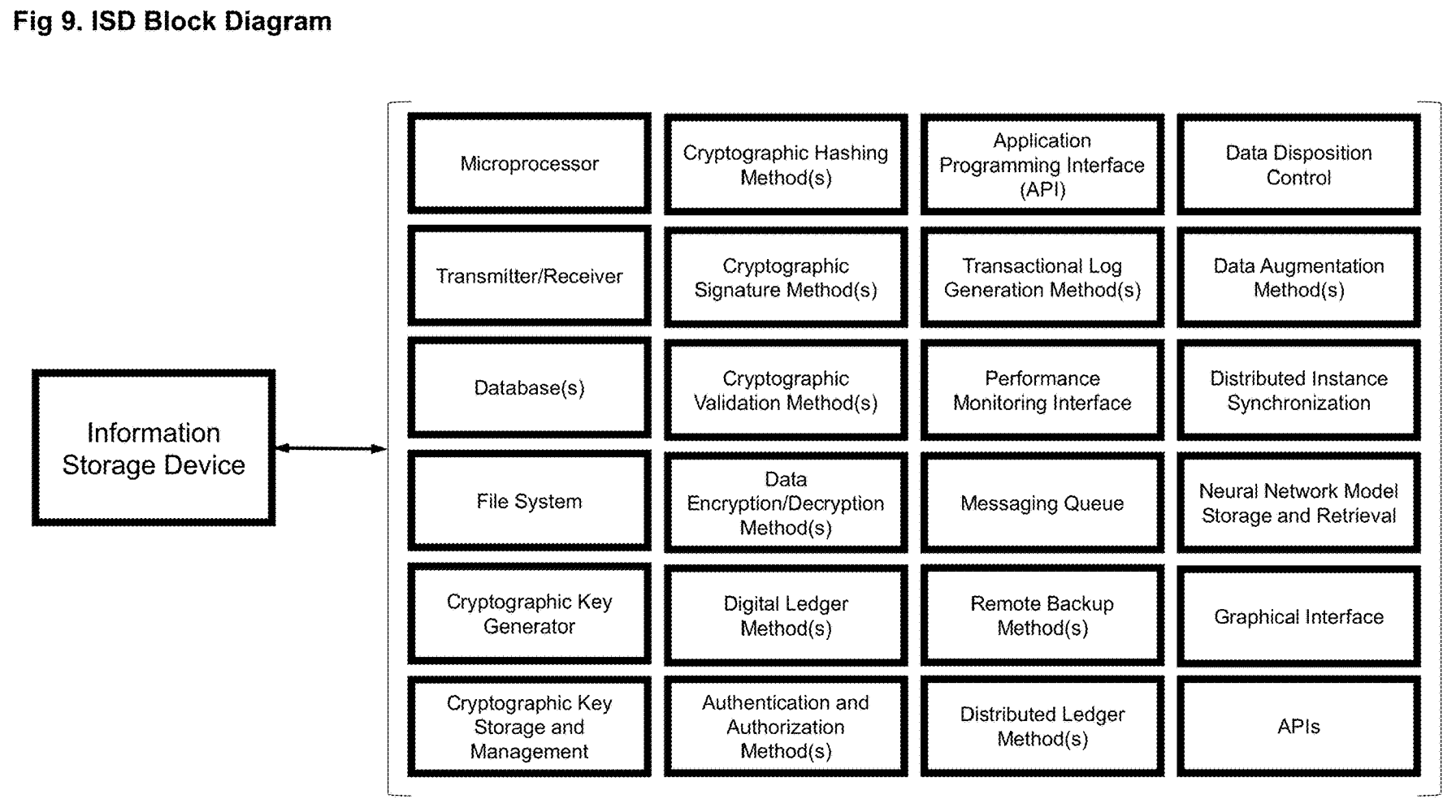

FIG. 9. illustrates ISD Block Diagram of the present invention.

FIG. 10. illustrates ISD Digital Signatures of Blocks of the present invention.

FIG. 11. illustrates ISD Block Mutability of the present invention.

FIG. 12. illustrates ISD Digital Ledgers Contribution of the present invention.

FIG. 13. is an MCI Block Diagram of the present invention.

FIG. 14. provides MCI Interview Process Examples of the present invention.

FIG. 15. illustrates a PRE Block Diagram of the present invention.

FIG. 16. illustrates PRE Algorithms of the present invention.

FIG. 17. illustrates PRE Neural Networks of the present invention.

FIG. 18. illustrates a PRE Gross Feature Analysis (Audio Example) of the present invention.

FIG. 19. illustrates a PRE VSSD (Audio Example) of the present invention.

FIG. 20. illustrates PRE Fine Feature Analysis (Audio Example) of the present invention.

FIG. 21. illustrates PRE Fine Feature Analysis (Image Example) of the present invention.

FIG. 22. illustrates PRE Multiple Character Extraction and Occurrence Measurement of the present invention.

FIG. 23. illustrates PRE Metadata Analysis of the present invention.

FIG. 24. illustrates PRE Textual Narratives of the present invention.

FIG. 25. illustrates PRE Model Visualization of Characteristic Occurrence Identification Over Time of the present invention.

FIG. 26. illustrates PRE Multi-Model Consensus Divergence of the present invention.

FIG. 27. illustrates PRE Model Temporary Divergence vs. Permanent Divergence of the present invention.

FIG. 28. Illustrates PRE Model Performance Peaks and Plateaus of the present invention.

FIG. 29. Illustrates PRE Models Divergence Over a Lifetime of the present invention.

FIG. 30. illustrates an SDG GAN Configuration (Image example) of the present invention.

FIG. 31. illustrates an SDG Data Disposition of the present invention.

FIG. 32. Illustrates Synthetic Data Layering/Recombination of Multiple GAN Models of the present invention.

FIG. 33. illustrates SDG-ISD Disposition Slopes of the present invention.

FIG. 34. illustrates PSE Block Diagram for the present invention.

FIG. 35. illustrates PSE Contextual Identification and Search for the present invention.

FIG. 36. illustrates PSE Historic Response Formulation.

FIG. 37. illustrates PSE Synthetic Response Formulation for the present invention.

FIG. 38. illustrates SLE 2D Images from SDG of the present invention.

FIG. 39. illustrates SLE 3D Model and Image Mapping of the present invention.

FIG. 40. illustrates SLE Parameter Adjusted Micro-Expressions of the present invention.

Figure 41:
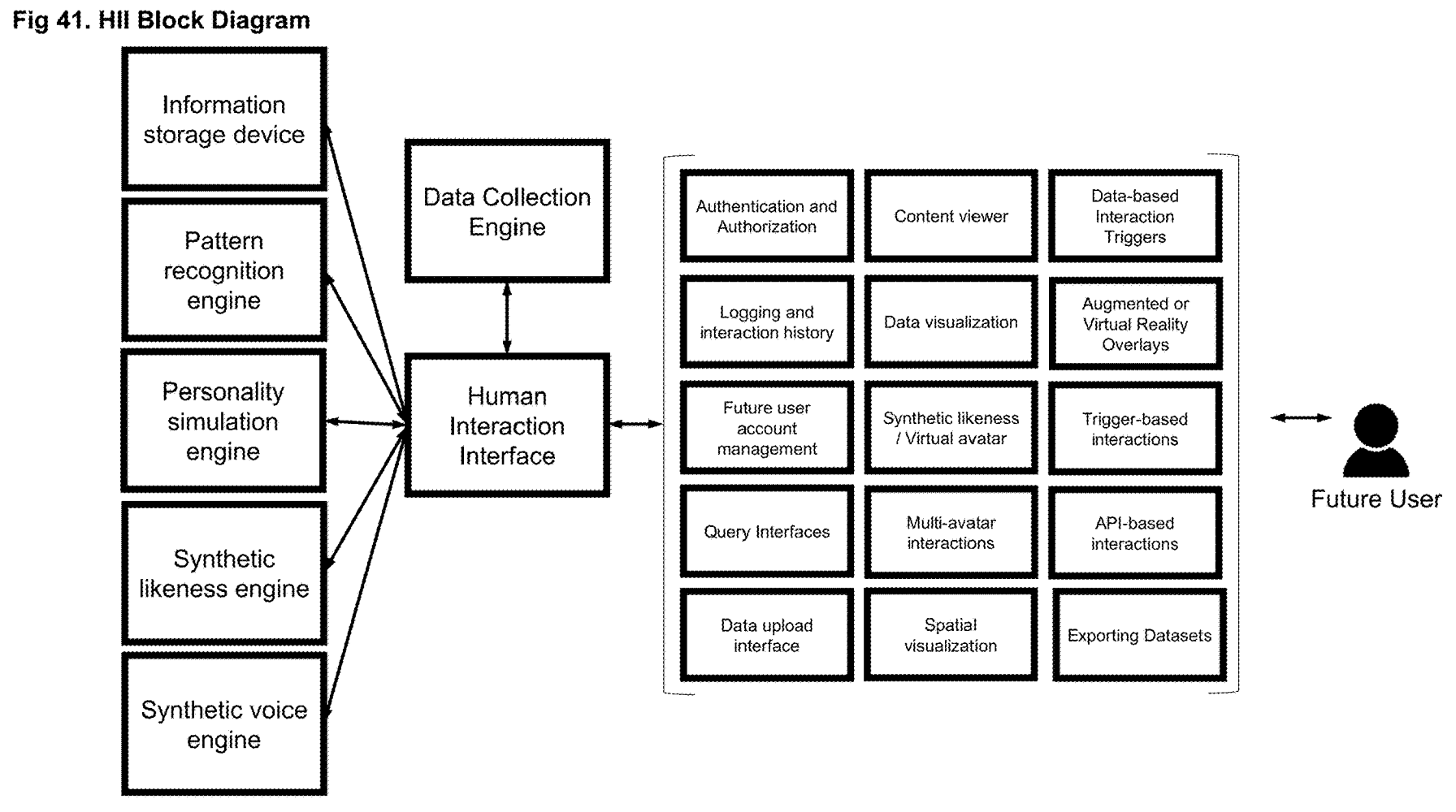

FIG. 41. illustrates an HII Block Diagram of the present invention.

FIG. 42. illustrates an HII Virtual Avatar Visualization of the present invention.

FIG. 43. illustrates an HII Virtual Avatar Interactions of the present invention.

FIG. 44. illustrates a DCE Block Diagram of the present invention.

FIG. 45. illustrates an Indeterminate Adaptation of System and State through Future User Interaction.

DETAILED DESCRIPTION OF THE INVENTION

In the following detailed description of the invention of exemplary embodiments of the invention, reference is made to the accompanying drawings (where like numbers represent like elements), which form a part hereof, and in which is shown by way of illustration specific exemplary embodiments in which the invention may be practiced. These embodiments are described in sufficient detail to enable those skilled in the art to practice the invention, but other embodiments may be utilized, and logical, mechanical, electrical, and other changes may be made without departing from the scope of the present invention. The following detailed description is, therefore, not to be taken in a limiting sense, and the scope of the present invention is defined only by the appended claims.

In the following description, numerous specific details are set forth to provide a thorough understanding of the invention. However, it is understood that the invention may be practiced without these specific details. In other instances, well-known structures and techniques known to one of ordinary skill in the art have not been shown in detail in order not to obscure the invention. Referring to the figures, it is possible to see the various major elements constituting the apparatus of the present invention.

Now referring to Figures, the embodiments of the present invention are illustrated.

100—Multimodal Sensor Device Array (MSDA)

The multimodal sensor device (MSD) provides a means of collecting and processing sensory information. MSDs are commonly configured in a multimodal sensor device array (MSDA) and function in parallel to capture data within one or more environments. The most common environment would be the end user's home environment, but could reasonably extend to a vehicle, workplace, outdoor environments, public spaces, or anywhere the end user spends time. The MSDA may be split geographically over large areas and utilize communication networks to transmit data for consolidation and processing.

A digital microprocessor and hardware. An MSD possesses one or more microprocessors to assist in the gathering and digitization of sensory information. MSDs are digital devices, using encoding methods to record data to storage media. MSDs possess several capabilities including but not limited to computation, network communication, temporary or long-term data storage, power and charging capabilities, digital and analogue input pins to receive sensor information from peripheral devices, noise filters, wired connections, including UART, USB, and serial connections, lights, and onboard sensors including environmental sensors.

Peripheral sensors and devices. Each MSD contains one or more peripheral devices, typically sensors, which are responsible for collecting environment information and converting this to either analogue or binary signals. Analogue signals are read as a variable voltage input which corresponds to a number within a range (such as 0 to 4095) whereas digital signals are binary and either 'high' voltage or 'low' voltage but alternating rapidly to represent binary numbers (typically high voltage states represent a 1, low voltage a 0). Peripheral devices may include environmental sensors, local storage media, such as SD Card or PSRAM memory chips as an example. Peripheral devices one or more communications protocols including but not limited to I2S, I2C, SPI, USB, UART, analogue to digital converters, and digital to analogue converters.

Each MSD possesses one or more power sources, typically a rechargeable battery or a direct current (DC) power source. Incoming power may be regulated to be delivered at one or more specific voltages (typically a nominal 3.3 v or 5 v) to meet the requirements of the microprocessor and its associated hardware. When a battery is provided, it is typically recharged via a charge controller and voltage regulator to meet its specifications. Power conversion when required is typically via a power supply, a low dropout regulator (LDO), or a buck converter which may be internal or external to the MSD. Current is regulated to ensure that the microprocessor and peripheral devices receive adequate power. Any combination of capacitors, inductors, resistors, or other methods are used to regulate power flow and reduce rapid and undesirable changes in current levels which may result in the degradation of performance.

Firmware and software. Each MSD is configured with firmware which is loaded over a wired or wireless connection to the device and saved in memory. The firmware controls the functioning of the microprocessor, the control of data input pins, the storage of information, and the operation of the physical features of the device. The device may also be loaded with an operating system firmware or software, such as a Real Time Operating System (or RTOS) which can be used to configure the reservation and utilization of system resources and processor computation. The firmware and software control the acquisition of data and how it is transferred to other devices.

Acquisition of sensor data. An MSDA can capture a variety of sensor data from numerous sources including but not limited to: Audio data; Motion data; Timing data; Touch sensor data; Proximity data; Environmental data; Digital signal communication data; Battery data; Network connectivity status and availability; Network communications latency; External device connectivity status and data; Mesh communications; and Synching and connectivity with charging stations which may bear a unique ID and a known physical location.

Audio data is gathered using one or more high-fidelity microphones. This microphone captures acoustic data (minute changes in air pressure caused by sound waves) and transfers it into electronic signals. The data from the microphone is transmitted to a buffer in the microprocessor for processing and transmission. The MSD is configured to capture audio for extended of periods which may span hours, days, months, or longer. Audio data is typically collected using a high sample rate (16 kHz to 44.1 kHz) in mono or stereo fashion.

Motion data is gathered using an accelerometer, magnetometer, compass, gyroscope, or a combination of these motion sensors which can determine rotation, bearing, motion vectors, vibration, acceleration, or other gross or fine movements. Motion data is collected as arrays of data which consist of X, Y, Z motion, rotation, acceleration, and bearing as it can be deduced by the combination of these sensor measurements.

Time data is gathered using both the internal clocks within a microprocessor unit or externally functioning as a peripheral device. Time data can also be gathered using a request across a communication network to an accurate time recording device capable of returning this information, such as an atomic clock, or wirelessly using remote satellite information from such services as GPS or through protocols such as LoRa or other satellite systems.

Touch sensor data is gathered using one or more capacitive touch sensors made available for human interaction. Capacitive touch data is captured in a binary fashion where the start, continuity, and cessation of touch are recorded with the times that they occurred. Capacitive touch sensors may be arranged to capture a discreet touch event or in an array to capture motions (swiping, sliding, rotation) where an end user's hand or fingers may move across multiple sensors in succession and be interpreted as motion. Non-capacitive methods, such as resistive touch, may also be used to achieve similar results.

Proximity data is gathered using one or more optical time-of-flight sensors, commonly referred to as LIDAR. LIDAR functions by measuring the interval of time it takes a stream of photons to leave an emitter, travel to and reflect off an object located some distance away, and for the photons to be detected by a receiver. Based on the constant C of the speed of light, the time from emission to receipt can be used to develop accurate distances from a sensor to an object. LIDAR data is used to detect the proximity, approach, and possession of the multimodal sensor by the end user, and to determine the nature of the environment around the device. This includes detection if the device is sitting in an open area or whether it is contained within the end user's clothes (such as a pocket) or other enclosure. In some instances, LIDAR data can be used to determine the reflectivity (albedo) of an object based on the strength of the signal returned to the receiver.

Environmental data is gathered from a temperature sensor of both the multimodal device as well as its environment. Temperature data can be used to determine the environment where the MSD is located and provides an indicator of the proper functioning of the device's hardware features. Air pressure, humidity, and air quality may also be tracked with designated sensors to further record or identify an environment.

Digital signal communication data is transmitted using various protocols including Wi-Fi, LoRa, and Bluetooth. The measurement of signal strength, the digital identification of wireless networks, the degree of interference of signals within an environment, the loss of packets during attempted transmission, the time of response from another wireless device (round-trip latency) can all be used to develop a clear understanding of the location of the device relative to other humans, their homes, their appliances, and other devices. Wired communication protocols including ethernet and RS-232 may be applied when devices are so equipped and wireless communication is not an optimal implementation.

Battery data is gathered by identifying the status of battery charge or and the voltage of the battery as power is consumed relative to the maximum and minimum known voltage permitted by the battery or control circuitry. The measurement of battery data provides indication of the usage of the device (how long since last charge). The rate of decrease of voltage compared to the activation of the sensors provides information on the battery performance decay over time and when the user of the device may have to charge or replace the battery.

The availability, identification, and strength of wireless networks is a clear indication of location and context of the device relative to other fixed or ambulatory wireless network devices, including routers or other equipment. Detecting network connections which have a named SSID (network ID) and MAC address provide a high degree of confidence of relative proximity to a known or unknown location. Signal strength provides a proximate distance measurement (close, midrange, or far).

Network communication latency of both local wireless communications to a router or other devices within a mesh configuration or the latency across a network are also indicators of contextual geographical location and the interstitial infrastructure configurations between the sensors and their endpoint connections. Consistent network latency may indicate that there is a long geographical distance between the multimodal sensor and the information storage device (ISD) in section [300] where the data is being received. Intermittent latency may indicate external network events (lots of users on the same network accessing limited bandwidth). Network packet loss may indicate an intermediate wireless protocol with inconsistent network connectivity or poor performance.

External device connectivity status and data is generated where one or more MSD can communicate with an array of external devices and peripheral sensors using common wireless protocols. When this occurs, data is transferred between the devices across a network or via a peer-to-peer protocol like Bluetooth. The multimodal sensor can receive or transmit to these devices. It may also be configured to pass on information from these devices wirelessly on their behalf. For example, it may receive a Bluetooth signal from a nearby peripheral and then pass on this data across a Wi-Fi, cellular, or LoRa network to the ISD.

Mesh communications and the presence of other compatible devices capable of forming a peer-to-peer connection occurs when an MSDA, operating in a mesh configuration, can determine which other devices are present on the network, their nature, their operating status, their function, and their approximate distances due to signal strength. The gain or loss of mesh nodes within a network may indicate movement of sensors in and out of the network range.

Additional peripheral devices. While the above sensors are standard in any configuration or embodiment of the multimodal sensor, an MSD may also be configured or manufactured with additional optional peripheral sensors which are contained within their enclosure or attached via a wired or wireless connection. This includes but is not limited to:

Image or video capture via an optical sensor (camera) enable where images may be captured and transmitted or processed and analyzed locally on the multimodal sensor using image recognition algorithms. Image data may be compressed prior to transmission in lossless or lossy formats. Analyzed images may be transmitted with full or reduced resolution. Metadata from the image analysis may be transmitted together or separately from image data.

Additional environmental sensors can also be attached via standard connections to the microprocessor. Optional air pressure, magnetic field, humidity, pH, and other sensors can be added to the device to gain a more multifaceted analysis of environmental conditions. Environmental features can be used to determine the location context of the end user as well as the physical context of the device (inside or outside).

Communications and protocols. The data captured by the MSDA is transmitted over a wired USB connection or wirelessly to an information storage device [300] to be stored, indexed, and analyzed.

The data that is transmitted from the multimodal sensor may be encoded in a variety of industry standard or custom/proprietary formats. Sensor data is most likely to be transmitted using a structured format, such as JSON or XML, which bundles sensor values with important metadata such as relative date and time (often specific to the millisecond or microsecond). Data from third party peripherals is likely to be encoded using the preferred encoding of that peripheral, potentially augmented by an MSD with additional metadata. Audio and image data may be transmitted in raw values or may be encoded using standard methods such as MP3, WAV, RAW, PNG, JPG, OGG, MP4, or other encoding protocols.

The MSDA may adopt several standard or custom transmission protocols including, but not limited to, TCP/IP, UDP, mesh broadcast, LoRaWAN, or WebSockets, depending on the nature of the data and the required transmission performance. Some protocols like TCP/IP can be evaluated for packet loss, as per above, while other protocols such as UDP and mesh broadcast do not resolve this information (packet loss is not measured to enhance transmission speed).

Edge data analysis and optimization. The MSD may contain software or firmware which enables the analysis of data on the device's microprocessor prior to transmission. For example, algorithms or machine learning models, such as neural networks, can be loaded on the device and executed as processes to evaluate the data being collected by the sensors and an initial analysis of the presence of gross or fine features (as identified by the pattern recognition engine (PRE) in section [500]). This analysis is recorded as metadata which is transmitted to the ISD. Additionally, it may also be used to optimize the operation on the device, including but not limited to optimizing power utilization and recharging requirements, performance, network traffic, and data storage requirements on the ISD.

Edge computation for data variability analysis. The operation of the MSDA may be optimized by utilizing data variability analysis of the datasets collected. If a multimodal sensor device were capturing several data streams, such as audio, motion, image, network, and environmental data, each of these streams of data may be analyzed for the relative variability of their data's maximum and minimum ranges within a period. As examples, the variability of sound is measured in decibels which records the degree of amplitude of the sound wave, motion is measured by the rates of acceleration, rotation in magnetic field or gyroscope readings, images in light intensity. If the variability is low, meaning the sensors are returning data which is relatively consistent from one sample or set of samples to the next, this would indicate low data variability. In real world terms, this might represent a quiet space, an unchanging image, a static set of wireless signals, or a consistent temperature or environmental information.

An MSD may apply this analysis to optimize the flow of information that it transmits across the network, reduce its sample rate from its sensors, or only resume transmission with the variability of the data exceeds a specific threshold, such as when a sound is detected or the device is picked up and moved to a new environment. This will have the desired effect of reducing data transmission and optimizing the overall performance of the MSDA and all subsequent data processing activities within the invention. It may be desirable to continue to send a subset of metadata to identify that the device is still working and connected (known as a ping, or heartbeat) to identify to the ISD that the connection is still valid but that the data variability is low. This will help form the narrative of the end user by differentiating between lost or missing data and static data that is omitted to optimize performance.

Additional or reconfigured devices. It is to be expected that the MSDA design and implementation may require alteration to meet the needs of their specific end user over an extend period of their life. For example, much of the audio recording information will be used to translate speech to text to record interactions. However, an end user may require or choose to interact with sign language to communicate, which would not be discernable by such devices. In a scenario where the end user desired to capture their interactions, each sensor device could be reconfigured or rearchitected to capture interaction data to optimize their biographical recording. This may be achieved by changing the configuration of the MSD or adding peripheral devices capable of capturing the required additional or alternate sensor data.

200—Digital Activity Recording (DAR) Software

Personal consumer devices, such as laptops and smartphones, provide a set of application programming interfaces (APIs) to connect to allow external software applications to connect to the device's hardware for unidirectional or bidirectional communication and control. Similarly, third-party software applications operating on these devices typically provide APIs for software-to-software unidirectional or bidirectional communications. API availability and standards are frequently changing and evolving as the hardware, controlling system firmware, and the software on these devices change, typically allowing for ever-greater integration of software and hardware. Additionally, a large set of APIs are available for software applications on local devices to connect to servers that are hosted locally or remotely on distributed networks.

The present invention incorporates a digital activity recording (DAR) software that is installed on one or more of the end user's digital devices. This DAR software leverages these diverse APIs for the purposes of capturing, recording, and transmitting the communications and usage patterns and activities of the end user. Because a large portion of an individual's interpersonal communications and activities, including business and personal time, are performed on digital devices, the DAR provides critical insights into the capture of human preoccupations, activities, events, interactions, and provides an essential set of primary information on the end user for the purposes of developing their biographical history and simulated personality. The DAR performs a secondary critical function of capturing contextual supporting information which is essential for the pattern recognition engine (PRE) in [500] to accurately categorize data to support the training of models.

DAR software is equipped with a means of configuration, typically via a graphical user interface, which defines the parameters for the collection of data from a device. This interface allows the end user to identify which data sources should be recorded and to grant permission to do so. Additionally, the DAR interface provides a variety of common functions which, if performed by another software, may not be accessible to the DAR due to the lack of APIs or restrictions in the function of these software. Examples of these common functions may be internet searches, as third-party browsers may not share browsing history via APIs to other software applications. In scenarios where the desired data is not accessible to be collected via API, the end user may use the DAR interface to perform some or all of the functions identified below.

DAR data collection and storage. The DAR software is configured to connect to one of more of the end user's devices or software applications and capture a variety of information, including but not limited to: Text SMS network transmitted text or multimedia communications; Audio recordings; Music and entertainment player; Internet searches and browsing; Photographs and videos; Usage patterns of applications installed on the device, including application names and details; Device network traffic patterns and communication methods; Notes and text stored on the device; Telephone call history and details; Biometric information (facial scans, iris scans, fingerprints); Calendar of activities; E-Books and audio books; Purchases of goods and services; Medical information; Food and recipes; Peripheral connections, identifications, and device usage information; Email communications; Peer to peer chat and communications; Device usage patterns; GPS location information; Screen wake and interaction time; Application usage patterns; File storage and data retrieval; Alarms and reminders; Network connectivity status; Charge and battery status; Music and multimedia playing; Browser navigation; Application store downloads or purchases; Paid subscriptions to reoccurring services; Locally created and stored media of other kinds (drawings, memos, etc.); Contact information for other entities (people, organization); Motion data, including accelerometer, compass, gyroscope data; and File storage information and capacity.

All digital activity data is collected with the express knowledge and consent of the end user. It is gathered for the purpose of developing a clear narrative of the interactions of the end user with other people, systems, and networks as well as the habits of the end user interacting with one or more of their personal devices. This data allows the invention to determine several important aspects of the user's activities to support the storage and recall of experiences and the identification of personal characteristics of the end user. The data above is collected with time and date information which can be used to define the context, location, activities, and interactions of an end user which can be correlated to other datasets from sources including the MSA.

The DAR utilizes a variety of application programming interfaces (APIs) provided by the device's operating system or installed software to gather this the above-noted usage information. APIs provide a structured means of detecting system events and interaction data from the operating system. Other software may also use APIs to enable application to application communications. Operating system features such as the file system also use APIs which allow the DAR to monitor for changes in files and folders and to detect new data being saved on the device. The DAR is configured to maximize access to these APIs. It may receive periodic updates, typically from the methods control interface (MCI) in section [400] to ensure that it is aligned to the latest APIs and is implementing the latest communications standards.

DAR-enabled devices gather essential data which is used to form inferences into the personal history, personality, and the psychological state of the end user through specific periods of time. Inferences are extracted from the data that the DAR collects and transmits to the information storage device (ISD) in section [300] to be analyzed by the pattern recognition engine (PRE) in section [500]. These inferences form an essential part of the biographical function of the method. Because this invention's purpose is to capture as accurate and complete of a representation of human experience and personality and to summarize and represent that data at a future time, these inferences into psychological states of mind produce a clear picture of data which cannot be collected by other means. Key inferences that can logically be derived by this data which collectively illustrate aspects of the biographical and psychological state of the end user, including but not limited to: Focus and attention; Preoccupations with contemporaneous events; Preferences and desires; Productivity and consumption; Sentiment and bias; Planned future events; Sentiment, opinions, and biases expressed via communications, and Personal media tastes.

Usage patterns of personal devices can indicate the degree of focus on a task. If a user is multi-tasking or only capable of performing a function for a few moments before being distracted by entertainment or an application or information source, it is possible to infer their relative engagement with their current activities. Longer uninterrupted periods of focus may indicate an activity is desirable or important to the end user. Brief periods of focus may indicate boredom or disengagement with their activities.

Search information, shared chats and communications, and browser search history provide mechanisms to identify what events and activities are topical during this period in the end-user's life. By evaluating the occurrence of key words, phrases, and concepts in the information the end user absorbs, it may be possible to identify the ideas which occupy the end user's attention.

The applications that the end user interacts with, or the items and topics that they engage with through these applications, provide an insight into the desires of the end user. These desires may be of mild interest or keen fascination, a scale which can be applied based on the patterns of the end user over an extended period. Extracted metadata about such desires may be measured numerically as the amplitude of the interest set against a time horizon to visualize the frequency of engagement. As preferences and desires grow and fall over time, such metadata should form 'peaks' of interest. These peaks, which may be present in multiple datasets collected by the DAR, help to form a narrative on the nature of the end user's changing desires over time.

Productive time may be inferred from the amount of time performing actions within a creative context, such as using an app whose primary purpose is to capture textual, graphic, or other creative outputs. Similarly, the amount of output from such activity is another measure of productivity or proficiency.

Consumption time may be inferred through the measurement of time spent using applications which do not result in a creative output, such as casual use of streaming and social media platforms where the ratio of time spent consuming vs. producing may be measured. Measuring the frequency and amplitude of consumption form the foundation to understanding how the end user's time is utilized and to what purposes.

At this point in our history, much of the communication that humans absorb is digital or digitally enabled peer-to-peer interactions. Digital communications and internet search information provide opportunity to extrapolate key information about the sentiments of biases toward key events. Exposed with the same events, from news or other sources, this invention may extract the patterns of topics which attract the end user. News coverage, for example, typically covers a range of topics. For the end user, one topic may be of specific interest, prompting more research and searching, while another topic is simply ignored. By performing a comparative analysis on the information that was presented to the end user versus the information which prompted greater research, it is possible to infer the topics of subjective value and derive insight into the interests of the end user. By evaluating the end user's metadata around their engagement (time, repetition, and sharing) on positive and negative opinions on each topic, sentiment towards or against specific topics, their bias, may be derived. Because views change over time, the change in interest of topics may also represent a directional shift of bias on topics one way or another, representing a change in personality or personal outlook.

An end user may use their device to plan future events. Task-style lists stored on the device or in other applications, chat communication, research on new topics, are all indicators of future direction or actions not yet taken. When an event or action is planned in the future, it represents for the end user a possible activity which could occur. This provides insight into how the end user acts leading up to potentially positive or negative events. The actions the end user takes to meet or avoid these future events provides insight into their mindset. Metadata derived may demonstrate a fatalistic approach, a proactive approach, or a negative or self-destructive approach to impending challenges. How the end user plans to reach future goals provides key insights into their personality and mindset.

The personal tastes of the end provides many biographical insights into their biases and preferences. With a diversity of different genres available in books, television shows, movies, websites, videos, blogs, and other topics, social interaction spaces and social media platforms, the personal tastes of the end user's chosen entertainment provide insights into how the end user prefers to be entertained, distracted, educated, and how they prefer to absorb new information. The end user may a consumer, a creator, or a participant in group learning activities. Each of these preferences can be measured proportionately and evaluated over time to derive psychological insights into how they absorb new sets of information.

The social network activities of the end user provide a contextual network of people whose interests and activities may be aligned to the end user, providing circumstantial information into the interests and desires of the end user. Social networks can include familial, friends, professional contacts, strangers, distant connections, neighbors, service providers, and business relationships.

Interaction with such networks can be measured on several scales including but not limited to: The number of people interacted with within a period of time; The frequency of interactions with people over time; The relative number of people interacted with relative to the size of the networks; The dynamism (likelihood of change) of the people within the social networks; The depth of time and communication with any members of the social network (superficial vs deep); The number of interactions with people outside any formalized social network; and There are numerous facets of biographical and personality information which can be inferred from these network interactions, including but not limited to: Relative degrees of introversion vs. extroversion; Planned interactions vs. dynamic (chance) interactions to indicate an openness to surprise and uncertainty; Depth of interaction vs. superficiality of conversation on specific topics and with specific people; The quality and importance of fostering and maintaining relationships; and The changing patterns of interactions across a network (consistent interaction vs rare or unpredictable interactions).

The physical wellbeing of the end user may be hard to derive via the measurement of their digital engagement (the interactions of healthy and unhealthy people may be similar), however the usage habits of the end user can be used to derive the amount of time performing sedentary actions vs. physically active actions. This information can be gathered based on the interactions with applications, monitoring of device sensor data to detect and count the degree, consistency, and duration of physical activities like walking, running, cycling, or other physical activities. The degree of personal fitness habits, and the reliability (likelihood to repeat) of the end user to perform these actions relative to other markers provides insights into the likelihood of the physical state of the end user and the degree of care the user puts into the maintenance of their physical wellbeing. Consumption habits may be inferred by spending information, such as the relative quality of food and supplements the user purchases.

Physiological and psychological wellbeing can be inferred from several markers, including but not limited to: Direct narratives on how the end user is feeling shared with a member of their social network; Ideation and preoccupation of the end user on ideas and concepts including self-care and self-harm; Direct analysis of communications (i.e. "I feel so angry"); Sentiment analysis of audio or textual communications; Consumption patterns of specific themes within entertainment and media; and Rest, recovery, and activity patterns.

Numerous inferences can be identified within each information type. Because this invention is primarily configured to evaluate one end user, the comparative analysis which is required to derive inference on biographical or psychological state may take a bulk of amount of data. Inference metadata is generated within the PRE and augments all relevant data within the ISD. Inference information can similarly be extracted from the data derived from the multimodal sensor device array (MSDA) in section [100].

It may be also possible for the end user to reference other users' information which is proactively disclosed and made available publicly. Performing a comparative analysis of the end user's peer group will provide a larger sample set to help to inform the end user how their psychological states compare with individuals in their peer group. Comparative personality analysis from a larger sample group provides a degree of relativity in the narrative which can be used to compare the end user's personality traits with those from their peer group within a certain era.

DAR as a method to support for supervised or semi-supervised learning within the pattern recognition engine [400].

The centralization of this data provides basis for contextual analysis of data and to the generation metadata to support supervised and unsupervised learning of the PRE. Comparing the data and metadata gathered by this device to the recognized interactions by the end user can provide a significantly more complex and rich contextual narrative of the end user.

DAR-derived information significantly assists in the development of PRE models by applying metadata which identifies the source, type, and context of gathered data. This metadata allows the extraction of labels and the development of categorization. Labelling and categorization are a foundational aspect of the supervised and semi-supervised development of neural networks as they allow the rapid and accurate building of training data samples.

The DAR software provides a mechanism for the end user to aggregate a large amount of biographical information which would otherwise be distributed across multiple systems and networks or simply lost. In aggregating this information from the end user's devices and directing it to a centralized repository (the ISD) which under the end user's direct control, then the end user can preserve the authoritative copies of the data needed to develop comprehensive biographical history and personality.

DAR software may be upgraded with version and code updates made available via internet hosted sites or directly from the MCI or ISD. DAR software may perform manual or automatic upgrades to add new features and enhancements including third-party integration methods.

300—Information Storage Device (ISD)

The information storage device (ISD) is a physical device connected to a local private network or a virtual device hosted on an external network. The ISD is responsible for several aspects within the invention.

A primary function of the ISD serves as a method of authenticating, receiving, storing, and retrieving data that is sent via the multimodal sensor device (MSD) array [100] and the digital activity recording (DAR) software [200]. The ISD is configured via the methods control interface (MCI) [400] to interface with and receive data with a collection of external computing devices. Through the MCI, the end user may also add in data from other sources.

Components. The ISD is equipped with one or more of the following hardware components: Microprocessor, Wired and or wireless data transmitter/receiver, Volatile memory (such as RAM), Data storage devices such as hard drives, Power supply, Optional peripherals such as input device(s) and or monitor screens, augmented or virtual reality interfaces The ISD is also equipped with one or more of the following software to permit its functioning, including: Operating system, Database, Cryptographic key generator (software or hardware), Cryptographic key wallet (software or hardware), Web server software, and Messaging queue.

Each device that is configured to work with the ISD is equipped with one or more asymmetric public and private cryptographic keys, which is used to validate its identity for secure communications and authentication purposes. Additionally, these devices are often capable of generating additional single or limited use symmetric and asymmetric keys. Upon network connection initiation between the MSDA or the DAR, the ISD receives device metadata including MAC address, IP address, local date/time, hardware characteristics, common alias, firmware version, public cryptographic key, as well as any metadata that has been assigned to the device during its configuration. ISD may authenticate each connecting device using one or more of these methods. When secure communication is required, standard cryptographic key exchange method is performed to enable a secure transport layer security (TLS) connection. The ISD returns an authentication token to the MSDA or DAR for ongoing communications which is valid for a particular amount of time to reduce the overhead of authentication.

The ISD can receive data following several protocols, including but not limited to TCP/IP, UDP, and WebSockets. It can also receive data via standard HTTP connection or secured HTTPS connections or related FTP and SFTP protocols. The ISD can receive and transmit data on common web protocols including but not limited to the REST protocol and GraphQL protocol for device communication. The ISD can function as a WebSocket server, client, or repeater to relay data to external subscribing devices to specific data streams as well as specific modules within the invention including the pattern recognition engine [500] and the synthetic data generator [600]

Data that is received by the ISD is programmatically augmented with additional metadata, including the system date of the ISD, any known details about the connection including the latency of the connection, the method of authentication, or other relevant data.

The number and nature of MSD or DAR-enabled end points is dynamic and may change and adapt, evolve to new versions, be expanded with new features or firmware, cease to function, be replaced, or be turned off for periods of time. Metadata which records the dynamic sources to the ISD is generated and recorded by the ISD. The addition of new data sources or the temporary or permanent losses of data sources all indicate a relationship with the end user's socio-economic capacity or their psychological engagement with the process of autobiographical capture identified in this invention, which can be expected to change over time.

The ISD stores the information it receives using a combination of temporary volatile storage (such as active memory or RAM) as well as long-term physical storage (such as traditional or solid-state hard drives or other durable digital media). The ISD can be augmented at any future point as new data storage technologies emerge which offer greater capacity, performance, durability, or reduced cost. Aging or failing media storage devices which are nearing or have exceeded their anticipated lifespan or warranty period can be substituted with new media storage devices, with data replication from one source to another to avoid unplanned failure and loss of data.

The ISD utilizes one or more database software applications which provide the means to capture data in a variety of formats, including but not limited to relationally (split into separate 'tables' which may be connected by unique values known as 'keys' which permit the future logical joining of data), as documents (structured hierarchical datasets which implement 'key' data descriptors and 'value' data value pairs), and/or graphs (data elements which are stored as 'nodes' and linked together with pointers known as 'edges' or 'links' which contain information about the relationship between the nodes), or any combination thereof. Additionally, ISD may store data as large binary objects, large text-based objects, or other means of aggregating data to be retrieved as one or more objects. The ISD may optionally use the file system of its operating system to also store files to a folder and file structure.

The ISD selectively implements and generates indexes for the datasets received. An index is a summarization of stored data which can be loaded into active memory to facilitate the searching and retrieval of stored information. Additional indexes of key features of the data may include its device of origin, data type, descriptive labels, text, time of receipt, and status.

Although the ISD has been identified as a device for simplicity's sake, it also can be configured to implement resiliency and data synchronization across multiple devices within one physical location or across a local or distributed network to minimize the potential of irretrievable data losses. For example, two or more physical computers could be established to function in parallel, with a main device receiving data from external sources and any number of secondary devices mirroring the main device and serving as redundant backups. In the event of a performance degradation of the main device, or any device failure, a secondary device can be selected through an election process (a peer evaluation of relative speed, capacity, and network performance) and a different device designated as the main device and assume the function of the main ISD to all externally connecting devices, such as the MSDA, DAR, or methods control interface. Similarly, the ISD may implement a process known as 'sharding' or segmentation to establish geographically separate instances which hold separate datasets.

Additional storage resiliency may also be configured for a single ISD or any number of ISDs working in synchronicity as identified above using storage methods such as RAID (or Redundant Array of Inexpensive Disks) which can be configured to save multiple hard disk copies in parallel or to permit the retrieval of lost data on one drive through a method known as 'striping' which stores sufficient redundant data on multiple drives to rebuild some or all lost data in the event of one of the drives becoming corrupted.

Several devices forming the ISD can also be configured to be geographically separated, such as across a network, and or virtualized by a third-party provider. Geographic displacement of various devices is a strategy to minimize the likelihood of loss due to catastrophic or interrupting natural evens, such as earthquakes, tornadoes, floods, or human-made events such as wars, sociopolitical strife, changing laws, climate change driven natural events, and relationships between regions. Several devices offering an ISD functionality can be configured for data replication. Less sophisticated storage devices can be used as simplistic backup methods. The ISD may also use distributed ledgers to disburse information across a large, self-managed network of participating nodes as identified in more detail below.

Data stored by the ISD is commonly encrypted at rest, meaning that the hardware, operating system, and or database software implements an encryption protocol so that if the physical ISD device or its storage hardware are stolen or compromised by an external actor, the data is protected through an acceptable cryptographic method to prevent its retrieval and abuse. Such cryptographic methods may face replacement or invalidation at some future date, so the encryption protocols used by the ISD may be upgraded with continually new methods to meet the latest data protection standards. Some degree of information may also be left unencrypted, such as specific indexes, to assist in the fast retrieval of encrypted information. Alternately, the end user may configure the ISD to leave a portion or all data decrypted for future access.

Data that is received by the ISD is digitally signed using a simple cryptographic hashing and signature protocol. Incoming data is received and queued for storage in 'blocks'. A block may be a packet or piece of data from a single MSD or DAR-enabled device, but may represent a range of data packets within a particular time period (second, minute, hour, year, etc.). Each new block of data is cryptographically 'signed' to include the hash of the previous block. The collection of signatures, known as a 'chain', can be used to validate the integrity of all the blocks of data.

If any block of data were altered, it would no longer align to its cryptographic hash and the alteration of the data can be detected by the ISD. While this method does not prevent the alteration of data, it does provide a means of detecting these changes and retroactively validating the integrity of the data.

Backward propagating of block signatures for enabling data disposition methods. Many current blockchain protocols do not permit the alteration or disposition of the data within the blockchain. This is to ensure that the integrity of the data is complete. In some configurations, data cannot be removed from the blockchain because it is required for validation. This is because validation of the data back to the original block is the paramount objective of these protocols.

The ISD enables the disposition of data in some circumstances as there are practical, legal, or logistical reasons to perform such actions over the lifespan of the end user. For example, if data stored in the ISD is deemed to be proprietary in nature or when the end user identifies it as desirable to dispose of this data. When such dispositions occur, the original data may be discarded and in exchange an authorizing disposition 'block' is stored to indicate that this alternation took place, and the authorizing information is stored in a secondary ('perpendicular') blockchain. Disposed blocks are replaced with 'stubs' which contain their original and new hashes, as well as the hashes from the secondary blockchain. The orphaned blocks which were written later than the discarded block, whose cryptographic hashes can no longer be validated due to the loss of a block, implement a backwards propagating signature method, with the newest block being identified as block 0, and the second newest block being identified as block −1, and so forth back to the point where the alteration is intended to occur. Where the chains now converge at the point of alteration, the authorizing disposition block signs both the original value as well as the backwards propagated signature, effectively joining the two together. The original branch of blocks ceases to be added to, and the authorizing disposition block is now used as the new source of authenticity. New cryptographic hashes are generated for the intervening blocks and added to a new 'branch' at the point of the authorizing disposition block. New incoming blocks are appended to this new branch going forward. This method of back propagation of cryptographically signed data enables editing in a way where the edits, and not the data itself, are indelible.

The purpose of this cryptographic method is to support the validation of the integrity of the biographical data. This method allows for flexibility on the edits but inflexibility on the record of the edit or disposition actions which has occurred. While some data may be removed permanently, the integrity of all the residual data can still be verified in the future, with the editing of data or disposition noted for historical record.

An unaltered record would also show the integrity of the lived experience, should it be required by the end user to validate or corroborate a specific account or narrative of events. Extensive editing or disposition of blocks, including the nature and degree of block alteration, would themselves be indicators of the end user's necessity or desire to have a 'revisionist history' of their lives on record. The veracity of recorded biographical histories would logically be viewed as less valuable if they have undergone extensive post-factual alternations, making them potentially less representative of the real events, experiences, and human actions as they occurred at the time. An interaction with the digital history of an end user who has extensive edits to their information may be seen to provide a less authentic, or honest, than one whose history is largely or completely unadulterated and provide insights into the end user's state of mind or environment where such edits were deemed necessary.

Storage of configuration data and history. The ISD stores configuration information, including authentication and end user access. It may also implement a standard open authentication method and permit third-party authentications for authentication and authorization. These methods are commonly referred to Open Auth, or OAuth, SAML, or other common authentication standards.

The machine learning models generated by the pattern recognition engine (PRE) identified in section [500] use the ISD are stored in the ISD. Additionally, the pattern recognition engine (PRE) will use the ISD for storage of any other data that it generates, including but not limited to entities, their relationships, and networks derived by the PRE.

Synthetic data and models. The synthetic data and the data generation models generated by the synthetic data generator (SDG) identified in section [600] are also stored in the ISD.

The personality simulation engine, synthetic likeness engine, synthetic voice engine, human interaction interface, and data collection engine all use the ISD as their primary means of storage.

Disposition of original data through synthetic model creation. The ISD possesses the capability of disposing of data and accepting disposition commands from the synthetic data generator (SDG) for the purposes of data storage optimization. As detailed in section [600], the SDG can apply machine learning methods to generate models which can recreate data with a high degree of fidelity to exceed a user defined threshold. When this occurs, original data may be disposed of within the ISD to optimize data storage. Disposition events and records are stored to the ISD. This process is covered in greater detail in section [600].

Distributed ledgers for data and models. The ISD possesses the capability to interact with one or more distributed ledgers for data backup, sharing, publication, and information exchange. Distributed ledgers are peer-based networks for data exchange whereby a network of computers, known as nodes, collaborate to replicates copies of data. Each node in the network stores a partial or full copy of all the data contained on the other nodes within the network. There is no central owner or administrator of the data. All users possess the same rights within the coded rules of the network. Due to its distributed nature of these ledgers, data resiliency is increased against natural or human-made losses.

The ISD possesses the protocols to connect to such distributed ledger networks and operate as a node for the purpose of sharing and receiving information for several purposes, including but not limited to: backup and preservation of its own data as a resilient and flexible distributed storage mechanism, backup and preservation of its pattern recognition and synthetic data generation models or original datasets, gathering public information which would enhance the invention's function and operations, including external pattern recognition models, the sourcing of training datasets, public information, information to augment the narrative of the end user, or any updates which are valuable to enhance the core functions of any of the modules of the invention, supporting the operation of the distributed ledger(s) as a data node, the self-publication or disclosure of information, the distribution of digital rights management information, the sharing of biographical information, machine learning models, raw or processed data, etc., receipt of data from a distributed array of one or more multimodal sensor devices which, for any reason, identifies the ledger as a useful means of sharing data back to the ISD, receipt of data from any device equipped with digital activity recording (DAR) software which, for any reason, identifies the ledger as a useful means of sharing data back to the ISD, publishing updates to software or firmware to MSDAs or DAR-enabled devices, and recovery of loss of information from other nodes to replace missing, destroyed, or deleted data.

These distributed ledgers may possess as few as two nodes, with no upper limit on the number of participants. Nodes may establish thresholds which define the quantity of data which they will choose to maintain on behalf of the network, contain only a limited subset of data or the full dataset, due to practical and systems limitations. Ledgers may limit the amount of data that each node may push to the network by implementing maximum caps on data shared within a particular timeframe, the maximum size of any dataset, the maximum frequency of updates, or any other practical limitation which permits the proper functioning of the network.

400—Methods Control Interface (MCI)

The methods control interface (MCI) is the primary means for the end user to visualize, interact with, configure, and control the functioning of the modules of this invention. The MCI is a software application which operates on a standard computer or server. Provided the MCI has a means of connectivity to the modules of this invention, such as via a local or wide network, the MCI can operate in a separate environment from the rest of this invention's modules.

End user and delegate access. The end user must authenticate themselves in a variety of methods to gain access to the MCI. By default, the end user possesses the highest level of access and control within the system, commonly called an administrator or superuser. The end user may also identify delegates who have lesser or equal control to themselves, including future users of this system. The end user may also designate delegates as the primary administrator of the system and conversely limit their own access.

Setting and maintaining authorizations of devices and users, including granting other users access within the MCI module. The MCI is the primary means of controlling or delegating access to the modular components within this invention. Modules of this system which require configuration and management are centrally managed by this interface. Each module in this system contains an application programming interface (API) which enabled bidirectional communication with the MCI.

Data management and administration. The MCI provides a granular set of role-based access rights to view, create, edit, and dispose of data. The MCI contains information on the physical and logical structured of the data storage media, including the capacities, brands, ages, and performance of physical storage media.

Selection of devices, datasets, and data types from MSDAs and DAR-enabled digital devices. The MCI enables the end user or their delegate to identify the devices from which the ISD is authorized to accept data and the type, manner, and form of this data. For MSDAs or DAR-enabled devices, the MCI can configure the types of data which will be transmitted to reduce the submission of unnecessary or undesired data.

Data management protocols within the ISD, including encryption. The MCI provides the primary means of establishing data management configuration, including database management and administration, file system management, metadata management, and data retention and disposition rules. The MCI enables management of storage media including physical storage devices (hard drives or equivalent), network accessible storage (NAS), and remote third-party provided storage (such as internet-connected storage). The MCI defines the standards and protocols for the encryption of data, including the management of public and private keys, the encryption protocols used, and any necessary steps to upgrade encryption protocols for new or previously encrypted data.

Classification of datasets and data encoding types. The MCI provides controls to classify datasets with additional metadata. For example, image data transmitted via an optical sensor must be encoded using a machine-readable encoding method and reinterpreted to display this image to the user at some future time. Setting the data type for this data source within the MCI will determine how the ISD encodes this data upon receipt using custom or standard encoding methods.

Enrolment and participation in distributed ledger networks. The MCI controls the enrollment of the ISD to participate within distributed networks, the degree of data shared, the degree of external third-party data it will maintain as a node on this network, and all associated rules with respect to participating in such distributed ledger networks.

Selection, extraction, and distribution of subsets of data within the ISD. The MCI permits the viewing, extraction, and distribution of any datasets within the ISD, provided the user is delegated sufficient permissions to do so. Extracted data from the ISD can optionally be signed to authenticate its originality or to apply digital rights management information identifying the provenance, copyright, an ownership of this data under applicable laws.

Import and manual creation of machine learning models, including externally developed modules. The MCI provides the ability to import externally created or third-party machine learning models. These models may be incorporated within elements of the invention which utilize such models, such as the pattern recognition engine (PRE) or the synthetic data generator (SDG). The MCI also provides an interface to design, train, validate, and deploy custom or user-defined machine learning models. The MCI allows the end user to configure which models are aligned to specific data types and how they are configured within a parallel or serial mode of data analysis (linked together so the outputs of one model feed the inputs of another model). The MCI provides an interface for evaluating the efficacy of models as well as any enhancement or degradation of their performance over time.

Manual addition of data to the ISD, without passing through MSDA or DAR. The MCI provides an interface to allow the end user or delegate to import additional data into the ISD. The end user will logically have data which was created prior to their adoption of this invention or produced in parallel with its use using systems that are not connected. As the end user may want to centralize all the relevant data they possess, the MCI permits this inclusion. The MCI can evaluate the incoming data to determine type and classification, as well as extract metadata about the incoming data to determine when it was created, edit, and any other data properties that are available. The MCI also allows the end user or delegated user to add relevant metadata to properly classify the data temporally and to apply additional contextual information which will be used to properly classify, index, and return the data at a future point.

Manual disposition of data within the ISD. The MCI provides an interface and means to initiate data disposition actions within the ISD, as identified in section [300].

Configuration of pattern recognition engine and synthetic data generator functions and models. The MCI provides an interface and means to configure the pattern recognition engine and synthetic data generator modules to optimize performance and configure internal controls within these modules.

End user interaction with the personality simulation engine (PSE) in section [700]. The MCI provides a means for the end user to interact with their PSE. These interactions enable the end user to evaluate and test the efficacy of the system. They also enable recorded interactions which form part of the end user's biographical history as their interaction with this system is part of their lived experience.

Configuration of the functions of the synthetic likeness and voice engines in [800] and [900] respectively. The MCI provides an interface and methods to configure both the synthetic voice and likeness engines. The MCI allows the end user to adjust and refine the methods of synthesis, to make parameter changes to both engines which control their outputs, and to add additional data to augment their sound and appearance outputs. The MCI provides the means to upload 2D an 3D assets for likenesses as well as filters and modifiers for voice and sound generation. This interface provides a means by which derived visual characteristics on appearance can be tailored through the adjustment of physical measurements and parameters which will control the appearance of the avatar.

Establishment and identification of external users who are authorized to access the human interaction interface (HII) in [1000]. The MCI provides an interface and methods for the end user or their delegate to determine which external users may access the human interaction interface (HII) identified in section [1000]. This may include generating and distributing access keys or codes, establishing pass phrases, or any other means of limiting and controlling access to known or unknown third parties. The MCI may limit certain users or user types to specific subsets of data which are based on time, activity, or metadata accessible by the search functions within the HII. For example, designated family members are granted access parts of the end user's biographical information not accessible to unknown or unrelated members. The MCI also provides means of allowing external systems to access any part of the device via an application programming interface (API) to allow indexing (such a search engine) or the extraction of data to a third-party software. The end user may also identify data subsets, including all data in the system, to be made public gradually over time or all at once.

Identification of datasets, sources, and searching methods within the data collection engine (DCE) in [1100]. The MCI provides an interface and methods to allow the end user or their delegate to configure the data collection engine (DCE) in section [1100]. This includes identifying known data sources for the DCE to monitor and import data or establishing network 'crawler' features which can search and identifying data sources through iterative analysis of third-party or internet content.

500—Pattern Recognition Engine (PRE)

The pattern recognition engine (PRE) performs a core set of functions within this invention by translating raw data within the information storage device (ISD) [300] into structured metadata using a variety of algorithms and machine learning methods, including but not limited to artificial neural networks.

The metadata generated by the PRE forms the basis for the categorization of data within the ISD for searching and interaction. It also serves an important support function for the synthetic data generator (SDG) in section [600] and the generative adversarial network (GAN) processes contained therein. It also provides essential metadata for configuring the outputs for the synthetic human voice and likeness engines by classifying data which can be used to tune their outputs.

The PRE processes data through one or numerous data processing steps which are flexible and customizable by the module control interface (MCI) in section [400]. Because this invention is intended to be used in a highly continuous fashion for a long duration, including the entire life span of the end user and beyond, it is expected that the specific technical methods, such as the use of neural networks as identified below, will change as new methods are adapted and discovered. However, the general functions of extracting data and generating metadata for the purposes of classification, search, and synthetic data generation are the core principles of the PRE and are the most relevant to this module of the invention.

The PRE contains and produces a large, dynamic, and diverse set of neural network models which are trained and evaluated regularly against the data in the ISD. It is expected that over the duration of the end user's natural life, the PRE will generate thousands of distinct pattern recognition and predictive models which are designed to produce metadata for all types of data within the ISD. Models will be created through the analysis of data from single and multiple data sources. Training of models will also include variable time ranges of the end user's life span. Models may be created for specific time-based subsets of data and used to measure their fall-off in performance as an indicator of the variability of the life experiences of the end users. Other models will be created to be continually retrained based on new data. It is anticipated that over time, the efficacy of trained models will diminish in classifying information within the end user's life as the person ages and changes through natural progression. However, these models are still highly valuable as their inability to classify data later in life is an indication of the degree of change in the biographical narrative and the habits and actions of the end user.

The PRE has access to and processes numerous data types, including audio, motion, sensor, time-series data, unstructured text data, human-generated and human-computer interaction data, and any ad-hoc or end user-provided data. The PRE enables the analysis of dozens or hundreds of diverse data types and encodings within the ISD. While the specific protocols for extracting training and analysis data would vary across data types, the following methods within the PRE generally apply to all different data types. For example, some neural network configurations are optimized to work with feature recognition in images, some are optimized to work with language and sound pattern recognition, while others are best suited for time-series data, including motion data or location data. In numerous examples below, audio is used to illustrate how the system functions as it represents both time-series data but also contains numerous dimensions which enables visual analysis and representation for illustrative purposes using standard graphical representations such as sound wave forms and full-color spectrographs. However, the use of audio analysis for explanatory and illustrative purposes does not limit the diversity of different data types which will be analyzed within the PRE.

Categorization of gross features within data using rules-based or neural network-based methods. The PRE applies multiple methods to evaluate data within the ISD and identify gross features within the data. Gross features refer to the values of data which may represent a change in state. For example, gross features in audio data may be areas of relative silence (low amplitude data) or areas where sound increases (amplitude increases). The silent area in this example would be one gross feature, while the period of noise that is detected would be another gross feature. In the process of gross feature categorization, the nature of what the data represents is not the primary focus, merely the identification of basic patterns which can be associated with time, area, volume, or other dimensions identified within the dataset. Audio will have periods of time where it is quiet and loud, depending on the interaction. Images will have areas where there are detectable edges, color patterns, contrasts, or artifacts. Three-dimensional data may have volumes bounds in 3 or 4 dimensions (for animated forms) which contain one or more meshes or objects. These are examples of the gross features which are detected within the PRE.

Gross feature categorization applies both static algorithms as well as trained neural networks to perform this categorization. Algorithms establish logical boundaries which can accurately determine logically analyzed parameters, such as a change in the amplitude of audio data, the variability of motion of location data within a certain period, the presence of certain colors or color contrasts within an image (such as the 'vibrancy' of an image), to name just a few potential parameters. When the presence of data within a dataset meets the algorithm parameters, a function may be triggered which identifies the presence of a feature. Similarly, the same algorithm or a subsequent algorithm can be configured to determine when that feature is no longer present within the dataset, marking the end of a feature.

The use of neural networks for high data variability. Some datasets, like accelerometer motion data, are highly variable and change unpredictably based on the orientation of the device. This is especially true in sensor data, where there are many factors which can alter how data is recorded. In these situations, neural networks may provide a superior method for categorizing data provided the neural network can be trained to recognize boundary conditions. Neural networks perform this evaluation by considering training datasets, accurately identify data samples which represent either features or boundary conditions. For example, a training set may contain extracted audio samples which represent one person or many people talking. If this training set is inputted into a neural network, and provided the sample size is sufficient, a neural network would establish a complex mathematical model that could accurately identify situations within the data which represented human speech within a degree of confidence between 0 and 1, with 1 representing complete confidence. Similarly, two neural networks could be trained to recognize the moments of transition between relative silence and the start of speech (when someone starts talking) as well as the transition between speech and relative silence (when someone stops talking). These transitions represent features within the data which a neural network would be well suited to identify.

Variable duration data sampling. The PRE implements both algorithms and trained models to conduct variable duration data sampling (VDDS). VDDS is a mechanism of either analyzing large pieces of information in smaller datasets or synthesizing small datasets into larger ones. VDDS is a critical component to gross feature characterization because it generates sample datasets of the appropriate size to capture specific boundary conditions and features which can be analyzed for feature identification.

For time series data, such as audio, the VDDS supports the classification of features by analyzing or synthesizing audio into different time ranges. For example, if you have 60 seconds of audio, you may want to know if this audio contains human speech. Fed through an algorithm or a trained neural network, you may detect that it does. However, you would not know how much speech it contained, or where in the dataset this feature was located. Practically, you may want to extract out all the periods of time where human speech is occurring so you would need to know when it started and stopped. In this case, the VDDS may extract out data in incrementally smaller segments from 60 seconds down to individual seconds and then evaluate these segments. You would then receive 60 results from your analysis (one for each second) which state the probability that this second contains human speech. Aggregating these results, you would then be able to determine the ranges of time where human speech occurred. Alternatively, the VDDS can extract out 60 1-second increments and feed them into an algorithm or neural network that recognizes boundary conditions where features start or end. Using this method, you would return a smaller dataset of all the 'start' conditions and all the 'end' conditions from which you could derive the periods of time when speech was occurring within the dataset. The PRE thus generates metadata which indicates the presence of a feature and the time (location) when that feature is found relative to the larger dataset. Finer grained VDDS analysis may produce more accurate identification of the location of the boundary conditions with the trade-off being that each smaller sample has less data to be analyzed which may make recognition more difficult. Thus, VDDS may encounter an operational floor by which the samples are too small to support accurate pattern recognition. By monitoring the 'failure' point of this VDDS sampling approach, the PRE identifies the optimal sample size for the accurate generation of metadata.

VDDS may also present longer periods of data for macro-feature analysis classification. For example, joining data samples together into a large dataset such as hours of audio would allow for the measurement and creation of bulk classifications such as "Quiet periods" occurring at night for several hours while the end user is sleeping, or "Active periods" during time where there is a relatively diverse and continuous number of activities captured within a period of time.

The VDDS provides the same sort of analysis potential for all other dimensional datasets where data can be extracted from the whole. This method can be applied to unstructured datasets, such as text, to extract out paragraphs from passages, sentences from paragraphs, words from sentences, and letters from words for example. It may also be applied to images to develop a tessellated sampling of images to extract out bounded sample sizes.

Analysis of gross features for multi-feature analysis. The above process of gross feature analysis can also be applied to extract multiple features within the same dataset by applying different algorithms or trained neural network-based models. The 60 seconds of audio used in the example above may contain human speech, but it could also contain environmental sounds which could also be recognized. For example, it could contain 10 seconds of human speech followed by a dog barking, an appliance being activated, and a large truck passing by. The audio may also possess signature qualities which represent various environments such as an inside space, a vehicle, or an open-air exterior space. Multiple neural networks could be applied to the same samples of audio at various durations extracted by the VDDS, resulting in multiple features being categorized within the dataset and their locations within the data adding additional metadata to be stored.

Fine feature analysis. Once gross feature analysis has identified the areas for further processing, fine feature analysis can be applied to further classify gross features down to specific events and translate the data within those designated time-ranges into relatively accurate and complete metadata to support biographical history narratives.

In addition to sampling data based on its time, the VDDS may also sample data based on other characteristics such as amplitude, volume, intensity, etc. In this case of audio, this may be frequency and amplitude. For example, a fine feature analysis may wish to only sample data within a specific frequency range or amplitude range. The VDDS will sample the full dataset but return a sub-sampled dataset accordingly, a process known as filtering. Filters provide bounding thresholds and ranges for data analysis where data that falls outside these ranges may be excluded from the training or classification set of the neural network. An example of this in audio data would be high-pass, low-pass, and notch filters. These filters work by removing specified audio data whose frequency falls beyond a specified frequency range in Hz. A high-pass filter allows all high frequency signals to be kept while discarding all the low-frequency signals, while a low-pass filter performs the equal but opposite function. A notch filter performs both functions, establishing a low and high threshold and only permitting data within a specified frequency to be analyzed. The benefits of applying filters allow for aspects of the data to be classified independently. Again in the case of audio, a high-pass filter could be applied to remove most of the human speech, which resonates at a relatively low acoustic frequency of approximately 0-300 Hz, varying typically for men, women, and children. A high-pass filter set to remove higher frequencies such as 400 Hz or above would largely remove the human voices and allow for fine feature analysis of the other noises within an environment, such as environmental acoustics for classifying rooms, appliances, or other devices within the data set. Similarly, applying a notch filter at specifically 60 Hz in a North American context would allow for the detection of electrical noises generated from any device powered by alternating current (AC). Such data would be indicative of devices and their relative location within an environment from the sensor and the end user, permitting analysis of the end user's activity and movement through a space.

Filters may be applied toward all data types. Image filters may similarly isolate certain colors to support feature analysis, increase or decrease the contrast of images, reduce or change the hue or saturation of colors, invert, convert to grey scale or black and white, or subsample the image (reduce its resolution) to support faster analysis and classification to name just a few potential filters. Filters can also be applied to unstructured data, such as dropping out textual content that is irrelevant or over-represented to better establish context and narrative. Filtering may be based on algorithms with specific mathematical or numerical definitions (such as ranges) or can be based on neural network filtering which applies methods of selective data removal. For example, one neural network may be trained to classify and remove all 'background' information from an image, leaving only the foreground or human subjects for analysis. Another neural network may be trained to remove all foreground subjects and analyze only environmental context (sky, light, nature) to classify the local weather and estimate the environmental experience for the end user.

Reprocessing previously examined data. From time to time the PRE will return to analyze data again after its models have been updated or enhanced through retraining or its algorithmic threshold bounds adjusted. Newly created models or adjusted algorithms may provide incremental enhancements or degradation in its ability to extract metadata. Reprocessing previously classified data provides an opportunity to glean any remaining features within the data, boost confidence in the metadata scoring, and to compare the performance of distinct model to evaluate overall whether confidence and accuracy have increased. The model is expected to produce different results with different degrees of confidence with each evolution of the neural network. If the measured performance of the updated model scores lower on previously processed datasets, this can be an indication that the new model is not as good as the old model. The results of re-processing data will inform the PRE on the efficacy of its model creation processes, such as the most suitable number of data samples required for training of new models, providing opportunities for enhancements or refinements.

Cross-data contextual analysis using relative time. Cross-data contextual analysis also plays an important role in accurately classifying the biographical experiences of the end user. Data collected specifically by the MSDAs and the DAR-enabled devices can frequently work to corroborate or contextualize the events which are detectable within the stored data. An example of cross-data contextual analysis may be to perform a comparison of audio data, image data, motion data, and location data from the end user who goes for a walk while carrying both a multimodal sensor device (MSD) as well as a smartphone equipped with the DAR software. The smartphone GPS location data captures the general exterior path of travel for the end user. The motion data from the MSD captures fine-grained accelerometer information which can determine the cadence and mode of movement (walking vs. jogging vs. cycling). The image data may capture both the end user and their environment and be analyzed to determine the end user's environmental experience (is it hot, sunny, rainy, cold), as well as the presence of other people and things. The location data may detect that at certain times the progress ceased moving. It is impossible to know from the GPS data whether the person sat, fell, went to sleep, were hit by a car, or just dropped their phone, all which would produce the same location data. However, the motion and bearing data from the MSD indicates that the person is still standing, moving from time to time, and facing a specific direction. The audio data provides much greater context as the end user's interaction can be analyzed. In this example the end user's audio information contains human voice patterns, and the end user can be heard having a conversation with another person. The presence of human voice, as well as the textual analysis of their conversation indicates they are discussing the weather with another person who is in proximity. Any photographic images may be used to identify and classify the specific person the end user interacted with.

The biographical narrative which comes from cross-data contextual analysis is much more complete when multiple data sets are brought together to build a corroborating narrative. In this case, in additional to the specific experiential metadata, narrative metadata would be generated by the PRE generated. Such a narrative may describe: "The end user took a 37-minute walk, starting and ending at their house. Along the way, they stopped for 6 minutes to have a conversation with Jane, their neighbor who lives 900 m away, about the weather. The end user took 3 pictures which indicate it is a bright, sunny day". The event then becomes searchable at a future point based on this narrative analysis, finding all the end user's interactions with Jane, their yearly fitness and mobility habits, the weather patterns of specific times, current events and topics and any other search criteria biographical and personality analysis. Had any of the data elements been absent, it would not have been possible to capture a complete or accurate narrative. Greater or fewer datasets impacts the nature and completeness of the narrative.

Training models from external sample datasets. The PRE may be configured to incorporate external datasets for the purposes of training robust neural network models. Depending on the habits of the end user, it may take a long time for the user to generate sufficient data to produce a robust training sample for neural network development which results in highly accurate classification and prediction. In such cases, it may be required to import external datasets of non-biographical data to augment these models to produce systems capable of recognizing and classifying new images, faces, objects, or features within any dataset.

When external datasets are imported, they may be sampled to create or augment training data. For example, if an end user never rides a bike, their personal data will not include the motion data which correlates to bicycle riding, and the neural network will be unable to classify this motion accurately if it were to occur. An end user may interact, through the MCI, to manually define this new unknown action as cycling, which would help to classify this information (a method known as supervised learning). This would potentially decrease the degree of feedback the end user must provide to the PRE to classify new experiences. By importing external datasets which include cycling, the PRE would have been able to more quickly classify this information. From this initial classification, the end user's data can be properly categorized and incorporated into future training data.

Bias in external training data. Importing external datasets does come at a risk of introducing unintended bias into the machine learning model which can potentially decrease the efficacy of this invention's ability to accurately record history and end user information. As this system is intended to be highly biased toward recognizing end user data, external datasets have the potential to skew this bias making models less accurate in classification or prediction. For example, the external dataset may contain data for training a model to detect cycling, but the data to be analyzed is of the end user rollerblading. This may cause the rollerblading information to be erroneously identified as cycling because the training data is biased toward cycling and does not contain samples of a similar, but different, rollerblading motion. There are many similar scenarios where bias in language analysis or image analysis models may struggle to classify information from people who look or speak differently than those within the end user's context. This may result in models which cannot contextualize the interactions of the end user accurately and result in incorrect biographical information.

Transitional training bias elimination. To overcome training bias where external datasets are applied, the PRE performs a phased or transitional bias elimination method. As new end user data is collected and classified, existing models are retrained so that the ratio of end user over external data increases, thereby reducing the potential impact of external data in the development of biases. This process repeats until the end user-derived data is sufficiently complete to support re-training models using only end user-generated data. The external data can then be phased out of the training data completely and purged from the ISD, and previous data sets can be reclassified with these user-centric models.

Inherited models and training data. The PRE enables the importing of large external training datasets where the contributor is one or more known persons within an existing familial or social context. For example, a parent could donate years of their lived experience data as the 'seed' for a child as a new end user. The parental experiences and their classification would provide context for recognizing all the people and things within the shared environment of the parent and the child. The models would readily recognize the parent and family member because these features are present in the training material. A similar process can be performed at the community level, where many people within a community donate training data for a new user so it possesses a broad set of training data. Data banks could also be established of open-source data donated by a global community to build robust culturally aligned training datasets.

In this way, the PRE is mimicking the human method of enculturation in the development of its pattern recognition methods. In humans, a child born into a social and environment context where their food, language, clothes, toys, rituals, and daily experience are fully defined by the biases of its parent or caregiver. These contextual patterns create biases which are present throughout childhood but begin to be supplanted as the child grows through adolescence through to adulthood. While biases of parents and culture are never fully eliminated, the new experiential data changes how the individual thinks and views events around them. Their own experiences and memories become a stronger influence on their future actions than when they were a child who relied almost exclusively on their parents to contextualize their experiences. In the phased elimination of bias within this invention, the end user may choose to eliminate external datasets over time or add their experiences to these datasets and form a hybrid set of trained neural networks which reflects their personal experiences as well as a broader set of non-lived experiences which could enable the system to better classify data as experience changes. Due to this invention's generational approach of mass data collection and categorization, such a process could continue over generations to leverage multiple lives to build a strong foundation of training data and neural network models which would be pass on and enhanced over an extended time horizon.

Training data generation and augmentation through data abstract corruption and manipulation. In many instances, the data generated by the end user may not contain enough diversity to ensure that the models learn to recognize all scenarios adequately. For example, a neural network trained to recognize a single image of a person may become proficient at recognizing that image but not the person contained therein. Instead, it is important that there are many pictures of that person, in many angles, in many lighting scenarios, making many facial expressions, and at various data sample sizes (resolution) to ensure the model can accurately classify the picytures of the person across a diverse number of scenarios. In short, the common patterns that the neural network learns must be varied enough to be recognizable within an acceptable range of situations.

To overcome this challenge, the PRE applies several algorithms and functions to support the grow of training samples from limited data. Image gross features may be extracted, rotated, blurred, noise or distortions added, color pixel data adjusted, mirrored, duplicated, skewed, or abstracted in any number of ways, with each abstraction joining the training data. Just as a human could recognize an image of the Eiffel Tower even if it were rotated, had its colours inverted, and dimensionally skewed by recognizing the features of its geometry and the patterns of its architecture, a neural network trained with adequately diverse training data is capable of learning and identifying the features which remain after the abstraction.

Different data will require different abstraction methods. For example, while an image might be reversed and still be recognizable, sound data would not likely be reversed. While an image might be rotated, sound would not swap time for amplitude. However, motion data would be, as it is quite common for the relative axes of motion data to change as the orientation of the sensor device changes in respect to the nature of the rotation and the force of gravity.

Another method especially for time-series data such as audio or motion data is to overlay segmented datasets and combine them through additive functions. Extracting one person talking and overlaying other audio samples, such as other people talking, pets, nature sounds, environmental interferences, echoes, and entertainment programs will also diversify the ability for the neural network to recognize the features of the end user. While image data may not be commonly additively overlaid (known as double exposure), as this is not a common image effect, images may be tessellated, collaged, tiled, or blended, to create new scenes and new interactions for enhanced training. Applying these data distortion and abstraction methods will strengthen the feature recognition of the neural network and build more robust pattern recognition models.

Cyclical analysis of data using standard time to develop biological narratives and identify noteworthy divergent events. In addition to recognizing features directly within the data from the MSDAs, the DAR-enabled devices, or any other datasets added via the MCI interface, the PRE also detects features and patterns within the metadata that it generates. This metadata assists in the purpose of establishing biological rhythms and patterns of the end user. This 'second-tier' metadata analysis provides the basis for biographical narratives and understanding pattens of unique and common behaviors for the end user.

Because generated metadata contains specific time-based information for the purposes of build a biographical history, metadata itself may be analyzed as time-series data capable of being analyzed to derive habitual patterns and cycles. This second-tier analysis allows the PRE to build models which may detect and predict reoccurring, such as daily, patterns which are part of a recognizable individual habit or ritual. Some end users may be more inclined to be pattern followers, while others undertake schedules which are difficult to classify due to their apparent unpredictability or randomness. In either scenario, such classifications are valuable as they both provide insight into the characteristics and personality of the end user as well as their biographical norms and activities.

Combined divergency from standard events as an index toward data classification and recall. When divergence from standard habitual patterns occurs, these divergence events are important features within the broader biographical narrative and form a means of indexing data for future recall. Divergent events occur when cyclical patterns within data or metadata disturbed. This might occur when something within the context of the end user experiences a significant change. Examples of such change may include any number of life events, such as when they have a new baby, adopt a new hobby, undertake a new activity, relocate for vacation or vocation, or are participating in a new job or role which requires patterns to temporarily or permanent shift.

By charting the degree of divergence between the data and the confidence of the previously trained neural network models (as in the failure to accurately classify or predict the actions of the end user based on previously identified patterns), such events would form 'peaks' of divergence. These divergence peaks would mean that established habits have changed temporarily, but over time return to their previous patterns. Divergence 'plateaus' might mean that a habit has changed permanently, and that the accuracy of a previously trained model is no longer reliable. In this scenario the model would need to be retrained or a new model generated to take into account the changes in data.

Divergence peaks provide a highly valuable way of indexing the entirety of an end user's life. They represent the moments of greatest change or transformation and would be natural areas of biographical interest. Indexing the data within these timeframes for future recall and prioritization provides a means of allowing the end user or future users to narrow in on periods of biographical information that are potentially the most interesting. Such periods of change are also highly indicative of how the end user responded to changes or challenges in their lives, whether they are excited or stressed, optimistic or pessimistic in the face of change. Such classifications support the creation of a simulated avatar.

'Plateaus' of divergence provide insights that a habit pattern and cycle has changed for a long period of time or perhaps permanently. While these plateaus provide valuable narrative insights into biographical histories, they are also evidence that a trained models is no longer performing well. Such plateaus provide the PRE evidence that it is time to retrain a new model to identify the new habits or patterns. The old models, trained on the previous datasets, is maintained and continues to examine the data alongside a newly trained model which is built on the new patterns. Should habits reverse at some future point, the old model will provide an indicator of whether 'things got back to normal'. If both the old and new models plateau at some future point, it might indicate that another large and permanent life change has occurred and yet another model is required. In addition to these periodic retraining, the PRE also maintains a model which is continually retrained. Such a continually learning model would provide ever-greater acceptance of habit changes. When the continually learning model encounters divergence peaks, then a significant life events would be detected and then integrated into the latest models.

Regardless of the approach, metadata analyses provide opportunities for classification and indexing of life data and will provide crucial markers for both the personality simulation engine in section [700] and future users of the system to identify features of keen interest or growth of the end user.

Augmentation or resolution of data with encyclopedic and contextual knowledge datasets. Data within the PRE will commonly be augmented with knowledge datasets to provide classifications and labels to data based. For example, if the ISD receive and possesses extensive GPS data, consisting of longitude, latitude, altitude, and time, the PRE may recognize locations but lack the context to determine why the end user is there. To establish a narrative, external contextual knowledge datasets may be added to support the labelling of data. In this example, importing geographic information, such as open-source street map data or named features with known latitudes and longitudes will allow the PRE to label the datasets. A specific longitude and latitude can be resolved to be a building, with a type (office or residential), a civic address, image reference data, and so forth. This augmentation allows for far more intuitive data management and discovery by humans who possess similar contextual knowledge.

The end user or future user searching the data would be able to search by address, neighborhood, city, country, and so-forth to find data which matches these criteria by proximity or by being within the bounds of a geographic feature. The address information, and its designation by the end user ("my home", "the office") also provides contextual data to structure more detailed and common biographical narratives such as "John went from his home to the office, arriving at 8:46 am". Any other labeled dataset can be used to augment the PRE to accomplish similar outcomes with other data. Labelling provides a means of supervised learning within the PRE to enable text-based indexing for future analysis and recall.

Applying unsupervised learning, semi-supervised learning, and fully supervised learning. The PRE implements unsupervised, semi-supervised, and fully supervised neural networks model creation. With supervised learning, training data is pre-classified (usually manually via the MCI) into datasets which are used to develop models which can recognize (accurately classify) data and to align it into known categories. In unsupervised learning, the PRE develops its own classifications based on the features that it identifies within the data which may be verified and named at a future time. The classifications that are created with the model can then be identified when compared to another labeled dataset or by a human capable of recognizing and naming the feature that has been classified. Semi-supervised learning provides a small amount of labeled training data with a large amount of unlabeled training data.

In the case of unsupervised or semi-supervised learning, the PRE may refer data samples or attempts at classification to the end user for adjudication via the MCI interface. In requesting adjudication, the PRE may ask the user to enter the label for the features identified within the dataset, or it may compare this dataset with a labeled dataset and ask the end user to confirm their alignment. User-confirmed classification provides validation that the model is correct, and the interactions with the end user through the MCI significantly enhance the learning outcomes for the PRE. Similarly, dishonest responses from the end user can completely corrupt models and make them perform erroneous pattern recognition.

Pattern and feature recognition, as discussed above, are core functions of the PRE, and the labelling of such features is a critical function of the overall system. Such labels form the basis of indexing but also form the linguistic and textual basis for forming language-based narratives and enabling the personality simulation engine to produce language-based descriptions of biographical events. Label accuracy is therefore especially important in the system. As data is labelled, any unlabeled datasets or datasets whose label confidence is low are reprocessed to potentially enhance the quality of its classification at a future point.

Prediction of events based on previous events using neural network methods. In the above methods, the PRE evaluated data for the purposes of classification of data and the production of metadata. The PRE also applies predictive modelling to generate metadata which describes events or features likely to occur within a dataset but which have not yet been recorded. In biographical narratives, which tend to be largely historical in nature and experiential, the value of prediction may be low. However, prediction provides an important mechanism for ensuring the continuous functioning of the invention's modules and performs a mechanism to audit the quality of the PRE's models in real time. If the PRE predicts the end user will perform an action, and they do, confidence in the models increases. If the PRE predicts an event which does not occur, and such predictions trend poorly despite the frequent retraining of such predictive models, this may indicate that the system does not have enough data yet to make predictions or that the end user's actions are relatively unpredictable by nature.

In either scenario, unpredictability provides crucial feedback to the PRE to take a variety of actions. It may expand its training dataset to include more data or shrink it to focus only on a smaller dataset, apply more abstraction to its training data to support unpredictable habits, request additional external data be added to its ISD datasets via the MCI including training libraries which would enable more accurate classification, or all the above. Another action may be to notify the end user that the PRE and the system is not yet ready to accurately classify the information, that the models are still premature, as a means of providing information to the end user on the functional health of the invention.

Influencing the actions of the end user through prediction. The PRE also informs the user of their degree of predictability, which could have the effect of changing the patterns of the end user. In providing feedback on the predictability of the user's actions, either high or low, the end user may change their actions in response to the PRE. When informed that their life is highly structured and predictable, the end user may choose to alter their habits and try a new routine. When informed their life is unpredictable, the end user may seek to provide structure. In either event, both outcomes are beneficial for the PRE as such actions will expand the side of sampled data and may be leveraged to enhance the efficacy of the PRE's neural network-based models. This predictive feedback method is an important factor in maintaining the overall health of the system.

Trend analysis of preference and bias over time based on frequency of matched or related events. As noted, because the PRE generates metadata and can perform metadata meta-analysis on trends over time, it is capable of recognizing when actions and habits change. These habits may be routine-based, or they may be interaction or experience based. For example, if the end user frequently plays one song within a period of time, but then over time the frequency of replay of this song reduces, these sets of events indicate that song may have become old, boring, and not interesting for the end user due to the frequency of exposure. Mapped over time, the PRE may generate a mapping of the changing experiences which rise, peak and then may wane over time. By analyzing the patterns of experiences of the end user, and the duration of time that these experiences repeated and persisted, a model of bias may be developed which demonstrates persistent interests verses transitory interests and their rates of change. Those persistent interests form a stronger bias indicator. The more persistent an experience, the greater its alignment to personal bias, and a stronger narrative can be developed.

All interests change over time and the PRE can use this persistence index to develop a bias trend line of interests. As the interests and experiences may be related, the bias can be modelled as a changing narrative. For example, if the end user hears one song they like, perhaps they then listen to the rest of the album. If they like that album, perhaps they expand and listen to multiple artists in the genre. Then they listen for a large time range within the genre, or cross into other genres they discover through more listening. The persistence and positive feedback element of these experiences demonstrates an appreciation bias toward a particular type of experiences for the end user.

Patterns of bias may also experience sharp changes. The PRE also supports the evaluation of classification confidence with the expectation that the degree of confidence will be lower during and after periods of the end user's bias change.

For example, the end user may become bored of a certain genre or experience and stop altogether. They may also experience something or gain some knowledge which sours their opinion of something, resulting in a rapid cessation of interest rather than a gradual shift. Such major shifts are biographically relevant as they may indicate an important life experience of the end user. Other experiential data, especially knowledge data, may provide the key to understanding what caused this shift in bias and interest.

Creation of textual narratives from metadata analysis. The PRE generates metadata output in the form of textual narratives, formulating categorized and labelled events as linguistic sentence structures. While the personality simulation engine (PSE) and the synthetic data generator (SDG) methods detail in their respective sections the means by which the system produce linguistic structures following the patterns of the end user, the PRE's textual narratives are objective and descriptive. Within these textual narratives, the nouns are derived by arranging the detected and labeled features within data with verbs which describe the sequences of recognizable events. The PRE references linguistic rules to formulate these narrative structures to produce sentences which are descriptive and literal narratives of events as they were occurred within the data.

Using this method, the PRE produces sentences such as "John walks to his front door, picks up his keys. He opens the door, walks through the door. He closes and locks the door". This structure is made possible through the analysis of motion and audio data within the ISD. Motion data detects the action of walking as the end user (John, in this scenario) carries a multimodal sensor. Other sensors detect the change in audio as he moves from room to room in his house, establishing direction. Audio data corroborates the action of picking up keys (the scrape and jangle of the keys), the opening and closing of the door, and the change in acoustic signature of an exterior space versus the previous interior space. Because each of the nouns has been previously classified using categorization models, they can be arranged in a time-based fashion following standard sentence construction to arrange the labeled data into a readable literal narrative.

Activity and movement data from motion datasets. The PRE can evaluate movement data and categorizing movement types into various labeled structures through structured and unstructured learning. Data types are validated with the end user through the MCI and gain labels during data generation or after the generation is complete. External training datasets may also be evaluated by the PRE to recognize previously unlabeled movements.

Human feature recognition and categorization within graphical datasets. The PRE can evaluate image data to recognize and classify faces and bodies within graphic datasets. Identity validation will typically be requested to the end user through the PRE once a degree of confidence has been gained that there is adequate data within the system for confident classification.

Human speech identification within audio datasets. The PRE can perform audio speech analysis to classify the speech of different speakers within the audio data. Voice classification forms an important part of the biographical narrative as verbal communications is a primary aspect of human-to-human interaction which can be central to data of primary importance and future engagement. Identification of difference voices also forms the basis of establishing the entities and their relationships and interactions within the data.

Speech-to-text extraction using natural language models. In addition to building and implementing models to accurately identify the presence of language data, the PRE can also translate speech audio to text using natural language classification models. These models may be trained fully on the voice of the end user or augmented through trained models which use general pre-built datasets largely conforming to standards and mores of linguist patterns in the end user's target languages. Because the PRE must classify the interactions of the end user with many other people who may speak with different languages and vocal characteristics, including a variety of ages, genders, accents, languages, the PRE will commonly apply models that have been trained on a highly diverse dataset within one or more relevant languages present. Further, as many bilingual speakers 'code switch' between their tongues to share different concepts which they feel are best aligned to specific languages, or to speak to others in the language of the choice, several models may need to be applied in parallel. The presence of linguistic code switching within speech data may be difficult to properly classify due to the fact it does not follow a single linguistic model but blends various models together dynamically. In these cases, models which can extract and classifying single words or sentences are preferrable and literal text extraction methods may be utilized.

Sentiment analysis of voice patterns. Sentiment analysis may be derived from both spoken words as well as textual analysis. For spoken words, sentiment may be derived from the tone, cadence, relative volume, speed, and delivery of the words, irrespective of its content. Words may be said sarcastically, kind words may be spoken with malice, harsh words may be spoken with jest or love. By applying externally derived or end-user defined sentiment scores for specific words, phrases, or audio characteristics, the PRE produces models which classify the sentiment of the spoken word into various categories which may be evaluated against labeled training data.

The PRE can also perform textual sentiment analysis by analyzing the relative positivity and negativity of the use of key words and sentences to derive the specific and overall sentiment of a passage. Sentiment in text may take many forms. Text may be terse, aggressive, academic, dismissive, conciliatory, inflammatory, simple, convoluted, or other categories. Text may possess many of these characteristics singularly or in parallel. The sentiment of text that the end user creates through speech recognition or analysis of textual data derived from the DAR provide an indication into their personality and state of mind. Similarly, the classification of text content that they ingest through media or printed text shows insight into their biases and predispositions toward specific methods of communication. The sentiment classification of how the end user speaks and how they prefer their content to be written is valuable metadata with respect to generating synthetic data and simulated personality traits.

Communicating with the end user through the methods control interface (MCI) [400] for data classification and supervised learning methods. At various times, the PRE has been shown to validate information with the end user through communication through the MCI. This communication may vary in its complexity and manner. Some common means of the PRE communicating with the end user includes but is not limited to the presentation of data for classification. This may occur through the MCI interface which enables the end user to observe the data that is being classified and provide one or more textual metadata labels. Additional contextual data, such as time, other media, and a larger data sample may be provided to enable understanding by the end user; Requests for clarification, where the PRE may generate a request to classify information which is happening in real time or which has recently occurred; Prediction notices, where the PRE may generate prediction of the end user's next actions; Performance statuses, where the PRE may communicate the performance of specific models or of the overall performance of the system. Additionally, the PRE may indicate necessary steps to remediate performance of models, such as the need to acquire external training data when the development of models lacks the necessary diversity or depth of data.

The sophistication of the PRE's communication methods via the MCI may change over time as it grows an ever-increasing degree of classified information. For example, the use of nouns and verbs within the end user's data will change the sentence structure of the PRE to incorporate these words into its communication. Response data from the end user within the MCI interface is also evaluated as a data stream. The speed, long-term accuracy, and depth of responses from the end user are also evaluated to gauge engagement in the process of biographical and personality recording, itself forming part of the biographical history.

Returning of metadata to the ISD and applying it to data using relational, document augmenting, and/or graph methods. The pre produces both models for classification and prediction as well as metadata. The models themselves are stored within the ISD and may be loaded, operated, and evaluated by the PRE's core functions. The metadata is typically created as structured data objects which are linked to the relevant data blocks within the ISD. Metadata typically possesses time and date information to associate the classification with the source data. Metadata may be human readable text, such as labels, binary or numeric classifications of confidence against those labels, or other outputs which are not human readable classifications. Metadata generated by the PRE is commonly stored in relational tables, document structures, or in graph databases, depending on the nature of the original data and the nature of the metadata.

The role of PRE feedback and its influence on the end user's actions. The PRE's classification and prediction of the end user's actions is a critical function for biographical indexing and narration of the end user's lived experiences. However, the results of the various models described above may illustrate aspects of the end user's life that, if the end user chooses to review, may influence their future actions. If the end user sees their actions are now or trending toward a certain direction, they may use this knowledge to make life choices. When this occurs, the trajectory of their lives might change, resulting in simultaneous changes of the accuracy to the PRE's models. The presentation of metadata may therefore reduce the quality of the models used to create it.

For the PRE, there are no positive or negative life choices, only changes in the accuracy of data classification and metadata generation. The emphasis is on the classification of data, not the judgement of action. When it classifies data, such evaluations may be made by the end user because now the information is quantified for review and reflection. If the end user evaluates the results of the PRE and this review results in a change in the life patterns and habits of the end user, this change is highly informative to the biographical narrative (the end user saw a need to change). The PRE can record these review interactions and correlate them against future changes in habit. The end user learned something about themselves which resulted in a change, which itself is a notable biographical event.

In this sense, the PRE evaluation process provides the end user with a subjective 'mirror' reflection of their lives as represented within the metadata. A mirror may show an individual that they have some dirt on their skin, causing the person to wipe the dirt away. The mirror did not wipe the dirt, only showed its presence, however it played a crucial role in the awareness of the dirt, while the person performed the classification (I am dirty), the judgement (I do not want to be dirty), and the action (I removed the unwanted dirt). Unlike a mirror, which is static, the PRE can identify that the awareness of the feedback to the end user caused an action, thereby deriving insight into the objectives of the end user to augment their biographical history.

600—Synthetic Data Generator (SDG)

The synthetic data generator (SDG) performs a critical bridge function between the elements that have been identified in sections [100] to [500] which are largely associated to data processing and the classification of the end user's biographical and personality information and the proceeding sections which are largely related to personality simulation, likeness, and interaction methods with this data. The SDG has several core roles which are central to the proper functioning, optimization, and sustainability of this invention.

The SDG's main function is to use the raw data in the ISD and the categorized and classified data from the PRE to produce new data which is both representative of the recorded data of the end user and synthetic in nature. Synthetic data is generated algorithmically or by the application of specified neural network models and contains representative features that are also present within the end user's original data. The SDG produces both the data synthetic data and data generation models which are leveraged by the other modules.

The generative adversarial network (GAN) method for producing synthetic data. The SDG invention uses Generative Adversarial Network (GAN) processes for developing data creation and evaluation methods. GANs utilize two distinct neural networks which iteratively leverage each other for mutual training and refinement. The first network is known as the Discriminator and the second is known as the Generator. Each network is reliant on the other network to train and function and produce recognizable and realistic synthetic data.

The role of the Discriminator is to predict whether a data sample is original or synthetic. Original data is data within the ISD which was somehow derived through observation of the end user. Synthetic data is data generated by the Generator function. Alternating datasets are fed into the Discriminator. The first dataset is a collection of labeled data which is the real data. The second dataset is data from the Generator, which at first randomly generated data which matches the same sample size as the real data (image resolution, audio sample duration, etc.). Using these two sets of data, the Discriminator is trained to recognize the different between real and generated data. The Discriminator outputs a 1 when it identifies real data, a 0 when it identifies generated data, and a floating-point value (between 0.00 and 1.00 for example) which represents its confidence in its assessment. A low confidence of classification may be 0.1 whereas a high confidence may be 0.9, and so forth. When it accurate classifies the correct type of data, the result is fed back into the system to refine the model.

The role of the Generator is to attempt to produce data with the characteristics which the Discriminator will classify as real data and score as high of a confidence as possible (1.00, or as close to 1.00 as it can achieve). Initially, random data samples are inputted into the Generator, which uses a neural network to produce an output sample. The output sample is fed into the input of Discriminator, as identified. The results of the Discriminator, between 0 and 1, are fed back into the Generator through a process known as 'back-propagation' to update the Generator's neural network weights, thus updating the weighting of the neural network nodes and changing its future output.

The Discriminator and Generator are trained iteratively. With each training iteration, the Discriminator gets better at differentiating between real data and generated data. Similarly, with each iteration the Generator gets better are producing outputs which are better at 'fooling' the Discriminator. Through an extensive set of iterations, the Generator becomes capable of producing synthetic data which is highly realistic. For example, if the Discriminator is fed portrait data of humans for example as real data, the Generator model is refined to produce faces which look highly realistic, even photorealistic in some cases. Similarly, any other dataset becomes possible to replicate or mimic using the same general method.

There are several different established models for optimizing GANs which exist, and it is expected that such methods will continually be discovered through the lifetime of this invention. Therefore, the SDG is configured to accept optimizations of the GAN algorithms and training approach to accept and implement more optimal methods. Currently known and applied methods, such as the StyleGAN process which is commonly used today, optimize the inputs into the Generator to enhance the quality of outputs and overall performance of the neural network training process.

Variational autoencoders. Variational autoencoders (VAEs) use an alternate method of inputting labeled training data which possesses a wide variety of pre-classified parameters and outputting generated data which attempts to generate data which matches, as closely as possible, these same parameters. VAEs have some significant output variations in comparison to GANs which may make them superior or inferior depending on the type of synthetic data being generated. VAEs may be configured to work with GANs, or to produce synthetic data in parallel to GANs. The SDG may use the Discriminator of a GAN to evaluate and compare the output of the Generator with a VAE to identify whether the output quality of the VAE is acceptable, superior, or inferior. VAE's offer opportunities for adjusting outputs based on the modification of input variables which also provide significant opportunities for 'tuning' the outputs to meet a desired purpose.

Using synthetic data for the optimization of data storage through targeted disposition. One of the primary roles of the SDG is to develop generation models which can synthesize data which meets a specific threshold of realism, this triggering the disposition or replacement of data within the information storage device (ISD) in section [300]. After a GAN is trained to reproduce labeled data and adequate training iterations have occurred to have a high degree of confidence in both the quality of the Discriminator's ability to discern real data from generated data and the quality of the Generator's ability to produce outputs which are highly realistic, the SDG begins to evaluate data within the ISD which can be generated by the SDG's models. Based on the classification of the GAN's training data, the SDG searches the ISD for other data whose metadata aligns to the training dataset. When additional data is found, the Discriminator checks it against the Generator to see how similar the datasets are. If the Generator's output exceeds a threshold of confidence, the SDG may trigger the ISD to discard the original data.

The purpose of this disposition process is to optimize the storage of data within the ISD. Although it takes data to train the Discriminator and Generator models which produce a GAN, once the GAN is produced, the model can produce synthetic data of sufficient quality which can be substituted for real data. In these scenarios, when the realism of the GAN's output exceeds a threshold of realism, the original data is no longer required as it can reliably be reproduced synthetically. Should the end user or a future user of the device wish to access this data, the SDG is able to regenerate the data that has been discarded and replace the missing datasets with synthetic data.

Synthetic data carries many of the same traits as original data but lacks the obvious value as a factual biographic record. However, it can play an important role in the representation of data for the end user or future user, especially in relationship to largely generic, repetitive, or low-value digital content. Over the decades of use of this invention by the end user, it is expected that there will be vast amounts of data whose relevance and replay would contain little to now value to any person. Low-value experiential data, which has already been parsed for biographical metadata and found to contain few or no unique events, may be replaced to significant optimize the storage and retrieval of data.

To provide some examples, the MSDAs and the DAR-enabled devices may capture numerous datasets which are of low value within the biographical and personality recording context of this device, including but not limited to: Domestic sounds, such as the sounds of sleeping, water running, doors opening and closing, fans, appliances, exterior traffic, Acoustic sounds from empty rooms, GPS or motion data when the end user is stationary, Device status information when MSDA or DAR-enabled devices are largely dormant, Exterior noises, such as traffic noises, wind, rain, animal calls, and Duplicate pictures and images of the same subjects.

With the GAN able to reproduce faithful imitations of this data, these datasets can be classified by the PRE, evaluated by the SDG, and then disposed of by the ISD. This process of disposition will yield massive storage optimizations within the ISD, purging data which has no specific value and does not contribute to an understanding of the end user or their biographical history or personality.

Disposition vs. synthesis. If certain datasets can be classified as low value, why not simply dispose of low value data? Whereas disposition alone would create 'holes' in the dataset, synthesis fills those holes and allows for an experiential understanding of the end user's biographical history, including recreations of the end user's sensory and environmental experience. The experientiality of the historic data can be recreated through the SDG's synthetic processes, even if the original data is no longer present. This allows the end user or future user to immerse themselves in a biographical history and view and interact with moments of the end user's past. If the original data has been disposed, the synthetic data may be used to recreate the specific experience. Although some of the data may be synthetic, the immersive and experiential nature of the history may still be enjoyed and potentially indistinguishable by the user.

The experience is likened to a virtual environment within an immersive video game. Within a game environment, many of the sounds are derived from samples which, when overlaid sufficiently, combine to create a unique environment that the player accepts as realistic and engaging. Video games may use synthetic data or sampled data to make this environment dynamic to the player's interactions, increasing the realism of the experience. The SDG's data synthesis performs a similar function, generating realistic experiential data for a future experience while significantly optimizing the storage of data on the ISD through disposition.

Disposition thresholds and slopes. Using the MCI, the end user can identify the degrees of disposition of data. The degree of disposition may be related to the confidence threshold of the Discriminator, where only data with a high degree of similarity to the synthesized data, above a high threshold of 0.99 confidence for example, is disposed. If those thresholds are lowered, the amount of data disposed will be increased and storage optimized. The end user may also select a sloped threshold, whereas data that has been recorded most recently, which may be of the highest value to the end user, has a high threshold but older data may have a lower threshold for disposition. The slopes can take any geometric form including but not limited to, linear, sinusoidal, curved, stepped, or user defined.

It is possible that the end user for practical, financial, or performance reasons would choose to dispose of all original data beyond a certain age and replace it with synthetic data or regenerate it on demand using SDG methods. Because the PRE has already classified and produced metadata for all the recognizable experiences, original data may not hold value anymore. Instead, the trained SDG models could be used to recreate experiences fully or at least sufficiently. As the models to generate data may be significantly smaller (tens, hundreds, or thousands of times) than the data they represent, the overall system performance may be optimized. Extensive disposition of the data will limit the ability of the PRE to perform historical re-classifications of data as its models are developed and updated, limiting the PRE to only evaluate data which has not undergone disposition or to utilize synthetic data for training purposes. While synthetic data may be indistinguishable from original data for the GAN and many humans, as proof of one's actions for evidentiary purposes it contains little to no value relative to original data and must be utilized and disposed of with prudence.

Generating synthetic data for events which never occurred. The SDG also generates data for events which are not found within the biographical history of the end user. These may be fictional events which combine the outputs of the SDG to produce new data and experiences of hypothetic events which are 'collaged' together from the outputs of the SDG. This manner of synthetic data is utilized in the creation of the virtual avatar which can embody actions and reactions not contained within the original dataset.

Model sharing and substitution. The SDG is also capable of representing multiple end users and containing distinctly identified libraries of models. Because each instance of an SDG is responsible for developing GAN models of their end user, the outputs are highly tailored to the user's experience. However, once a model is generated it may be shared with other end users to augment the recreation of their experiences. For example, two end users may have their own copies of this invention. End User 1 has a GAN capable of reproducing her likeness and voice which is highly accurate due to the availability of years of training data. End User 2 has a GAN which can produce his likeness and voice in the same way. Should these two users share a set of historical biographical experiences, they may choose to share their GAN models for ingest into their own SDGs. After sharing, each would possess an enhanced ability to reproduce higher quality synthetic data, optimizing their respective ISDs through greater disposition of data and enhancing the quality of the experiential recreation of their biographical histories.

Synthesizing metadata. The SDG has the capacity to synthesize metadata which is produce by the PRE. Like any other form of data, all forms of metadata can be simulated by a GAN. Metadata has the advantage of being highly categorized in its description of events making it ideally suited as training material for supervised training of models. This synthetic metadata is useful for producing the narration of descriptive events primarily for the personality simulation engine (PSE) in section [700].

Generating models for the personality simulation engine (PSE) in section [700] and the synthetic likeness and voice engines (SLE and SVE) in sections [800] and [900]. Generative models generated within the SDG are exportable for use within the PSE, SLE, and SVE. These exportable models are used by these engines to produce new content to simulate biographical or interaction events including interactions with future users.

700—Personality Simulation Engine (PSE)

The personality simulation engine (PSE) utilizes the classified metadata that is generated within the PRE to identify and return segments of the end user's biographical history or synthesize reactions to stimuli which are recognizably alike those of the end user. PSE reactions are driven by external inputs. Input stimulus can come from a variety of different sources but is primarily driven by the human interaction interface (HIT) in section [1000] or the data collection engine (DCE) in section [1100]. The HII input interface gathers a representative amount of data to identify the context of the future user's specific interaction objectives and passes these parameters to the PSE.

Diverse input types and parameters. The PSE accepts a diverse range of inputs, accepting data from the HIT and DCE. The three primary methods are textual/linguistic-based, data-driven, and system (API)-based queries.

Textual/linguistic-based interaction. This will be sets of textual data which represent the linguistic, conversational, and idiomatic structures of the end user. This text-based interaction can be routed to the synthetic voice and likeness engines [800] and [900] as the basis for generating audio and visual data which is delivered to the future user via the human interaction interface (HII) in section [1000].

Data-driven queries. The PSE may receive non-textual data queries including data driven queries. When a query is accompanied by media data for example, the accompanying media data will be analyzed by the PRE classification models to identify its relationship, if any, to the end user.

System-based queries. The PRE also receives objective system-based queries which may provide requests for the retrieval or simulation of specific periods of biographical data or the synthetic simulation of such data from the SDG. System-based queries provide their specific context via metadata within the query and do not need to be parsed to determine context from a textual or linguistic request.

Identifying query context. For textual/linguistic queries the PSE first identifies the context of the query. Such queries are often presented to the PSE as first-, second-, and third-person interactions. If the query relates to the end user in the second person (you, your, yours), the PSE prepares a synthetic response in the first person (I, we me, us, etc.) on behalf of the end user and based on its personality traits and the context of the question. If the query relates to the end user in the third person (he, she, his, hers, theirs, etc.) then the PSE response is returned in kind. In either response, the reply from the PSE is structured to most align the linguistic and textual patterns of the end user; a first-person response will mimic the end user's tone and voice within the context of the engagement and a third-person response will mimic how the end user would have described a historic event from memory, mimicking the end user's 'voice' and style.

Historical context. In addition to the narrative context of the query, the PSE also extracts out the historical era, situational context, the subject or purpose of the engagement, as well as the nature of the relationship between the end user and the person making the query (the future user).

Establishing the era of the end user's life. The PSE establishs the era within the end user's life for which it is simulating a response. If the invention is correctly configured to capture the complete duration of a person's life from birth to old age, it will contain many eras where the trained models and potential responses to interaction will differ significantly. Queries may include requests for age-specific responses, multi-age responses, in aggregated life responses.

Age-response types. Age-based responses will identify and utilize a subset of the end user's biographical history, bounded by specific date ranges. Multi-age queries will identify the best response from whichever age is most aligned to the query provided. For example, one response may come from the embodiment of the elderly end user, while another may come from a child embodiment of the end user. Aggregate life responses will utilize one or more personality models made up a composite of the end user's life. Although this version of the end user may have never existed, it may represent the most desirable means of interaction as this simulation will contain all of life's experiences, history, and reference information, representing the synthesis of the end user's recorded experiences.

Environmental context. Based on the query, the PSE will also attempt to identify the appropriate environmental, spatial, or social context of the end user. Within the defined age-based response, the end user's metadata may contain numerous contexts including home, work, travel, physical or social activities, and any other setting which has been identified by the PRE. The PSE will further refine the response to the best-matching context of the query.

Relationship to future user. The PSE will also attempt to identify the relationship between the future user and the end user. While this may be defined through structured data fields gathered by the HII, the PSE will also attempt to deduce the nature of this relationship to further define the nature and lexical structure and sentiment of the response. For example, if the future user is family member vs. a stranger with no prior association with the end user (researcher, biographer, investigator, etc.) the responses will be structured to utilize the appropriate response language, tone, and structure of the end user based on their recorded social interactions.

Response methods. The PSE can response to these inputs in one or more manners including synthetic textual responses, synthetic data responses, original data responses, and metadata responses. The PSE will utilize the appropriate response type to best match the nature of the incoming query and to furnish the appropriate data based on the nature of the end user's relationship to the future user making this request and their associated privileges.

Response types. The PSE collects input stimulus has several primary modes of interaction. These modes include but are not limited to: Conversational interactions between a future user and the PSE via the HII, Replay or of data from specific periods and events; Recreations of events which occurred, miming or re-enacting events; providing external data; and Direct System to System Queries.

Replay or of data from specific periods and events. The future user may request either a replay, where the data exists, or a recreation via synthetic data of events as they were recorded to have occurred.

Recreations of events which occurred, miming or re-enacting events. The future user may wish to see recreations or re-enactments of events. Re-enactments leverage both the synthetic human likeness generators identified in sections [800] and [900].

By providing external data, the future user may bring in external data for analysis and classification by the models stored within the system. Based on the interpretation of this external data by the models, the PSE will perform a query and return either matching information from the ISD (similar experiences) or the simulated end user shares its perspective on this data, representing how the end user likely would respond to this data.

Direct System to System Queries. The PSE also permits system to system queries, providing an intermediate layer for another system to query data rapidly and request metadata types, periods of time, and data with greater specificity. The PSE returns a metadata response of a likely interpretation and response to this query.

Time-constrained interactions. The PSE is designed to provide a set of realistic interactions within a time-constrained context of an engagement which could last a few seconds to several hours or longer. Within this constrained interaction window, the PSE generates a set of responses to external stimulus which are intended to be as highly representative of the end user's own reactions within a user-selected window of the end user's biographical history. The PSE accepts these interactions via either the MCI interface, controlled by the end user or their delegate, or through the HII.

The PSE evaluates the metadata patterns, classifications, and narratives within the PRE and develops models capable of generating predictive behavior data. Using the classified biographical actions of end user, the PSE evaluates the data preceding those actions to create models of environmental or interactive triggers which correlates to the end user's response. The PSE analyzes available data to find which events may have triggered reactions from the end user. The PSE categorizes these events into triggering sets based on a broad spectrum of metadata, including textual analysis (speech or written), human to human interaction patterns, environmental factors, cyclical patterns (time of day, time of month, seasons) to determine how the end user reacted to interaction, confrontation, positive and negative stimulus, environment, and many other sets of metadata derived by the PRE.

Based on a subset of recorded data that follows the triggers, the PSE uses predictive models (such as those generated by the PRE) to produce an array of possible responses that the end user would most likely demonstrate given all correlated triggers. The PSE samples biographical data on what the end user said and did in response to a similar set of triggers as well as generates a list of alternate responses based on observed responses to other scenarios. While the triggers of the original event and the HII interaction are unlikely to be identical, the PSE implements a cascading evaluation of all known triggers (time of day, nature of interaction, stimulus) and gradually reduces the specificity of the triggers until a user-defined threshold is reached of possible predictions of the end user's reactions. An action and response are then generated.

Interaction session history as inputs to personality simulation. In addition to historic actions of the end user, the history of the interactions between the PSE and the future user forms a history of its own. Each interaction cycle results in a transitory or permanent session history which also has a weight on the nature of the interaction and forms a set of triggers. Without a history, the PSE would produce responses without context to the interactions which came previously. The result would be highly artificial and potentially jarring as the responses may not have continuity to the future user. The PSE's interaction memory for the session adds additional triggers to guide the consistency of the interaction. If a user begins to interact with the PSE on one subject which elicits a strong response from the PSE, the memory of these responses forms an output which is channeled back into the input of the PSE as part of the context for any subsequent engagement. The session memory of the PSE influences each subsequent response, as to not backtrack onto previous topics, as well as to build on the sentiment of the conversation.

Storage of interactions for post-end user system augmentation. The end user may specify whether PSE-generated interactions become an expanding part of the end user's model and augment the data within the ISD or whether these sessions are transitory to maintain the fidelity of the date from within the end user's recorded life. A continual learning model would allow each subsequent interaction to expand the neural networks within the PRE and PSE and provide the invention with an evergreening set of data to continue to modify the simulation. However, it could also introduce simulation-driven 'trauma' or 'fatigue' where the new data degrades the efficacy or integrity of the models generated from the end user's biographical data. The end user must define through the MCI their preferences which will impact the experience of the future user.

Recreation of voice patterns, language, syntax, vocabulary. The natural language outputs from the PRE are configured to identify the language and vocabulary as it is spoken by the end user, not as grammatical rules dictate. Humans do not typically follow language structure slavishly within their interactions, and verbal interactions can be rife with repeated words, broken sentences, stutters, verbal ticks, non-verbal noise responses (grunts or guttural sounds), laughter, whistles, language code switching, inappropriate punctuation (such as statements said as questions). Interaction information documented by the PRE captures the nature of this interaction as fully as possible to build a representative vocabulary to represent how the end user would communicate. Based on the above, common natural language models based on standard linguistic models will not be suitable to represent the end user's vernacular. For an accurate recreation of the end user's personality, knowledge, culture, context, and biographical information, the PSE adopts language in the form it was recorded by the PRE as the basis for its interactions with a future user.

Tone and vocabulary variability by context. The PSE emulates the speech patterns of the end user based on changes to the subject of the inquiry. This may occur when the subject, familiarity, and nature of relationship with the subject of their interaction changes, such as shifting from peers to family. When speaking to family and friends, idioms, word usage, speed, and subject matter is likely to be highly different than when speaking to peers or superiors in a professional or public setting. This is because the end user has different relationships which leverage different parts of their lexical knowledge. Experience and education may have identified some idiomatic usage as inappropriate in some circumstances (swearing in a familial or professional setting for example). A desire to associate with one's close friends and family linguistically may also move the end user to speak most closely to the patterns of those in their proximity, adopting the mores, tones, syntax, or other characteristics of those in their environment.

The PSE leverages the linguistic variability of the end user communicates when shifting from verbal communication to textual communication. Written language structures follow a modestly different pattern and structure from vocalized sentences, meaning that most people do not speak like how they write. While textual information may be the clearest to interpret and recreate, it may form an inaccurate basis for simulating the personality of the end user in all contexts. Depending on the nature of the interaction with the personality through the human interaction interface (HII) in section [1000] and the nature of the relationship between the end user and the user of the HIT, the PSE may choose to adopt one or more of these linguistic models when generating interaction information.

Body language inference. The PSE sources the associated body language metadata within the ISD and passes this information to the synthetic likeliness engine (SLE) for the visual representation of the avatar. However, it is anticipated that such biometric metadata will be limited due inherent challenges of accurately capturing such data. To the end, the PSE utilizes the MCI to engage the end user on a series of sessions to capture this information through a recorded interview process. During the process, the end user's body language is captured by the MCI and recorded as a training set for modelling and reference. Body posture and gross body movements are captured via motion capture. Finer movements, such as finger movements, facial expressions, minor motions of the head and neck, are all captured and analyzed via video. These bodily features may use external training data to classify these motions and changes for their intensity, motion, and postures. To provide a reasonable sample, this interview process must be repeated several times over the life of the end user to gather data on how they respond throughout their lives and at various ages. This training data is used to develop models for simulating the end user's bodily motions in association to the sentiment and presentation of their responses to the future user.

Topics of interest. As has been mentioned previously in the section on the PRE, the DAR provides an opportunity to capture the end user's topics of interest. Since many of an end user's life experiences are increasingly delivered through digital infrastructure, the end user's interests may be captured through digital means. This interest mapping is aligned to the period of the end user's life and can be charted as progressions in interest and bias over time.

Within the PSE, these interests form a basis for interaction between the PSE and a user. Interests can form a natural framework for interaction between humans and is utilized as an interaction gambit between the PSE and the future user to direct conversations along topics which have been experienced by the end user. For example, the end user might have read an eBook, and while their recall of the book's content may fade, the recording of their reading over a period of the end user's life provides insight into topics that both interested and potentially influenced their outlook on life. By leveraging the interaction between the PSE and a user, such external content can be referenced and brought into the interaction as related materials. The PSE may either reference the content, display the content as part of the interaction through the human interaction interface in section [1000], or pantomime or paraphrase content from such sources as it relates to the era of the end user's life that is the subject of the interaction.

Variable age recreation. As has been mentioned the PSE has the capability to sample a sliding window of time from the end user's biographical experiences, associated metadata, and models to represent likely responses to interactions suitable for any iteration of the end user personality and the future user's desires.

Weighted selection of data based on the indexing of uncommon events as key points of life. As has been mentioned, the PRE indexes moments where its recognition models failed to accurately predict the end user's patterns. These eras represent periods of change or transformation in the end user's life where the experiences did not align to an experience that had been recorded previously. During the early part of the end user's experience, it is expected that these peaks will happen frequently representing the significant changes and growth of childhood and adolescence. However, such changes will continue to happen during each transition of the end user's life.

By over-indexing on these periods of change, the PSE generates interactions and share knowledge in these periods as primary areas of interest and potential interaction with a user. Like how humans tell stories of periods where their life underwent great and unexpected change such as the inclusion of new family members, an accident, a new job, migration to new areas, a new vocation or educational program, socioeconomic or political strife, the learning of new languages and information, the PSE will draw from these areas in a weighted manner in preparing responses to user interaction.

Interactions prompted by the data collection engine (DCE) identified in section [1100]. Emergent events that are contemporary to the future user's life may be gathered and evaluated by the PRE and PSE to identify commonalities and themes present within the biographical history of the end user. When commonalities are found, these trigger proactive interactions from the PSE to the future user. Commonalities are identified and interactions are structured around the nature of the new data identified.

Interactions may be triggered pseudo-randomly or irregularly by the PSE, bringing forward excerpts of knowledge or experience proactively and are transmitting this to the future user via the interface without Specific requests or prompting (such as digressive, non sequitur, 'magic 8 ball', or anecdotal modes).

800—Synthetic Likeness Engine (SLE)

The synthetic likeness engine (SLE) produces a likeness of the end user as an animated 2D image or representation of a 3D form. For each era of the end user's biographical history, this likeness is adapted to represent their appearance during that period. The likeness is known as a virtual 'avatar' which is depicted to walk, speak, gesture, pose, move, and act in alignment to biometric data recorded from the end user. The avatar reenacts biographical events and interactions that the end user experienced. In addition to human representation, the SLE represents objects and forms to contextualize or interact with the avatar's actions.

Blended 2D 3D representation. The SLE avatar implements a blended method to make the avatar realistic through the combination of gross animation of the 3D form combined with fine animation of the textures which are mapped on the avatar to give specific features, such as wrinkles, blemishes, distinctive marks, hair patterns, skin tone, and micro-expressions. Whereas the gross movements are informed by sensor data, image, and video materials which capture how the end user moved in life, the fine features are generated from likeness images produced by the synthetic data generator (SDG) in section [600]. These images are then texture mapped using common 'UV' mapping methods to align to the geometry of the 3D model's body. The combination of 3D form with applied texture mapping produces a realistic likeness of the human which may be dynamically viewed from any angle within a representative 3D environment.

Bodily representation. The SLE represents the end user's entire body. Sensor derived datasets may not contain this information as much of the activities of the end user may be obscured by the environment, clothing, or the angle of scope of visual records. To facilitate a comprehensive visualization of the end user, additional image data can be added via the MCI to complete any required image datasets for a realistic and comprehensive image of the end user's body, skin, and physical characteristics.

Foundational rigged 3D assets. The SLE uses templated 3D forms of children and adults as the basis for the avatars. Templates are generic gendered templates which are imported via the MCI to represent common body shapes, body mass, musculatures, fats, limb lengths, flexibility, hair growth patterns, skin tones and shades, manual dexterity, facial features, and proportions. Templates are then adapted using data analyzed by the PRE. All the physical features of the body are used to adjust the templates with specific parameters to match the body geometry of the end user at specific times in their biographical history. Skin tone, blemishes, and features are extracted from image data through feature recognition. Hair length, color, texture, placement, and styles are also evaluated and mapped to the template to be parametrically generated and adjusted.

Individual and age-specific locomotion specific. Templated animations of rigged limbs are also adjusted by sensor and image analysis data to establish stride length, speeds of limb movements, common actions and movements, and the like. Rigging is adjusted to reflect range of motion or motion limitations. How a child runs and plays is very different from how an adult or an elderly person may move, and so this data as well is updated to reflect the spryness, agility, muscle response speed, center of balance, and other characteristics that form the basis of movement throughout life.

Unique physical characteristics. Major distinguishing physical characteristics such as birth or trauma related characteristics, marks, injuries, amputations, and other defining characteristics are also made to the limbs, skeletal structure, proportions, and features of the avatar. As traumas may increase over time and be compounded, these features are continually updated and adapted based on the latest image and motion capture information within the system. The end user may also wish to specify specific features, abilities, and limitations through the MCI. Certain characteristics, such as arthritis or double-jointed flexibility may not be otherwise detectable by observable data and if the end user sees these are relevant may need to add these abilities or constraints manually.

Accessory hair and clothes. Human forms are constantly in motion, changing under the influences of environment, gravity, age, food, and experience. However, the variability of hair, clothes, makeup, and other styling and accessories may change much more rapidly.

With respect to styling of hair, hair growth, style, form, thickness, hairline, texture, and style is generated and animated as a gradual change which is interrupted by periods which relate to times when the end user cut or changed their hair. Because hair and aesthetics are so changeable, the SLE adopts defined styles and applies parametric degrees of variability within a style to simulate messy hair, gelled or styled hair, combed, braided, twisted, permed, natural or any combination thereof. Based on the outputs from the PRE and the SDG, the SLE will attempt to match the appropriate styling of the hair but to some degree will at best only be able to approximate this hair. The end user may need to define specific eras and styles for their avatar if a more accurate depiction is required.

Via the MCI, the SLE utilizes assets which represent the real assets (belongings, fashions) and accessories of life and applying them to the avatar. Assets may be clothes and accessories, including piercings. Their combination of cloth wear may be detected by the PRE but it also may be user defined. The end user may also specify a different set of clothes to represent specific eras or activities within their biographical history. Without constant video or a frequent querying of the end user via the MCI, the SLE cannot consistently parse out the clothing selections and choices but instead forms a best estimate based on time of day, day of the week, known wardrobe, randomness, activity classification, situational context, interaction, and environmental factors (temperature, precipitation, etc.).

Animation of the facial features and hands. The 3D avatar rigging includes fine control over all the musculature groups within the face to permit animation of the facial features, which is synchronized with the synthetic voice engine (SVE) to produce animations which are aligned to the words that are being spoken by the avatar. Using standard phoneme rigging information, the data generated by the personality simulation engine (PSE) is used to animate the rigging of the facial features to form mouth movements that are synchronized with the generated vocal utterances of the avatar. Expanding beyond just the mouth, the eyes, neck and head, and the rest of body are also animated to simulate fully expressive facial features.

Many people are also highly expressive with their hands and limbs when talking. Physical emphasis of speech patterns may be detected by motion data to some degree, derived from video data which can measure the motion and the position of hands and fingers, or may be user defined through generic or custom models. Standard libraries of motions may also be referenced to control the rigging of the avatar. The combination of motion with speech from the PRE provides the basis for the degree and nature of hand gestures and movements.

Detailed facial characteristics. In addition to the rigging, the detailed facial characteristics of the avatar are generated by the synthetic data generator (SDG). The SDG references all available image data to reproduce the facial mapping of the end user with realistic blemishes, wrinkles, and micro-expressions which will significantly enhance the realism of the avatar. Facial image data from the SDG is imported as image data by the SLE. The facial geometries are mapped using a facial recognition model and applied against the 3D geometry of the avatar. As the avatar speaks and moves, the mapping updates based on these characteristics. The facial geometries extracted by the PRE and generated by the SDG are applied to update the 3D avatar.

Overlay of synthetic visual data with 3D forms. The SLE implements an overlay method whereby the detailed bodily features, specifically the face, is overlaid as separate layers of image data to combine a resultant single video.

Mapping image data to adjust the avatar's geometries. The avatar's geometries are adjusted through measurements taken from image and video data. One of the primary means of establishing 3D geometries from 2D data is through a process commonly used within the 3D and animation industries called photogrammetry. Photogrammetry applies an algorithmic measurement of 2D images which are captured at various angles to extract the measurements, proportions, and volumes of 3D real world objects. The SLE uses photogrammetry to perform this function on the human body. By referencing a wide variety of image data sources, a 3D model is derived of the end user's body and feature proportions. These proportions are used to adjust the parameters of the base avatar's bone and musculature information to be proportionate to the end user. This process must be applied at numerous times throughout the life of the end user but results in an animated physical growth and change pattern throughout their life.

900—Synthetic Voice Engine (SVE)

The Synthetic Voice Engine (SVG) synchronizes with the Synthetic Likeness Engine (SLE) in section [800] to produce an integrated audio overlay which aligns to the animation and movement of the avatar character. As the primary engine of audio, the SVE can also generate non-verbal sounds from both the end user and other recorded events within their history.

The SVE uses the vocal characteristics of the end user such as the timbre, cadence, tone, frequency, and other features of their voice that are identified in the PRE. It utilizes the voice generation models developed by the SDG and uses these models to generate audio from the text that is created from the personality simulation engine (PSE) in section [700] to produce a realistic audio that represents the end user at various ages and periods of their biographical history.

There are numerous aspects of voice which are adjusted by the SVE to tailor the speaking of the end user's avatar to the nature of the engagement. If the voice is a targeted interaction method within the human interaction interface (HII) identified in section [1000], the means of interaction with the HII are factors used to adjust the speech patterns of the avatar. Simulated person-to-person interactions for example adopt a conversational language pattern, whereas text-based interactions may adopt a more formalized language structure.

If the avatar is recreating a conversation or a monologue that the end user delivered within the history, the SVE mimics the exact delivery of the historical event as much as possible. However, if the avatar is narrating an event, describing what happened instead re-enacting it by leveraging the narrative metadata from the PRE, then a separate model may be used for clarity.

Contextual modelling of the vocal characteristics requires that the specific context considers several of the following factors, including but not limited to: Context of the biographical history; Context of the means of communication used by the end user (conversational vs. formal vs. performative, etc.); Context of the interaction within the HIT by a future user, specifically the relationship between the future user and the avatar; Context of the simulated age of the avatar within the end user's life history; and Context of the method of interaction, whether verbal, textual, or system to system. Each of these contexts may adjust the vocal outputs of the SVE accordingly.

Augmenting and adjusting standard vocabulary and speech patterns. The SDG reproduces trained voice print models, and the PSE produces the spoken language content (words, utterances, sounds). Together, the SVN combined these two outputs to generate acoustic information. The SVN adapts the acoustic data output of these models to adjust pitch, cadence, intonation, and other acoustic characteristics to align to the contextual parameters of the interaction and the relative age of the end user's avatar. This is done by applying audio adjustment filters which modulate the acoustic properties of the voice. This modulation is performed based on the output of the personality simulation engine (PSE) and aligned to the timing of the synthetic likeness engine's animation of the avatar's form.

Using classified sentiment data for recreating cadence and tone. As noted, the PRE performs a sentiment analysis of the vocal characteristics of the voice data within the ISD. This sentiment data is linked as metadata to the original data samples. How and when the end user exhibits sentiment, or emotion, and to what degree becomes crucial to the realism of the simulation. Sentiment adjustments to the synthetic voice are generated by the PSE based on the predictive conversation models developed around the end user's interactions.

Environmental adjustments to voice. For reenactments of the voice, the characteristics of the virtual environment that the avatar is occupying have an impact on the vocal properties that the avatar is sharing. Environmental filters can be applied to the voice to simulate the context of the various rooms and environments that the end user occupied. For example, if the avatar is occupying a virtual enclosed space which would practically be subject to echo or reverberation, such filters can be applied to the voice to achieve these simulations.

Layering of other sounds for context. In addition to human sounds, the SVE also utilizes the SDG to produce environmental sounds to layer over the vocal simulation to add context. The nature of the augmentation will vary depending on whether the sounds are contextual and secondary or related to the primary topic of the interaction.

1000—Human Interaction Interface (HII)

The human interaction interface (HII) is the primary method for future users for connecting to, seeing, interacting with, searching, and viewing the wide variety of data that has been collected by this invention. The HII is also the interface which enables the visualization and interaction with the synthetic personality of the end user. Users of the HII have been referred to as 'future users' throughout this document to identify them as being separate entities from the end user that this system is supporting. Future users may be granted access by the end user or their delegate at any time during the lifespan of the usage of this invention, not merely after the end user has, through death or choice to discontinue its use, ceased adding new data into this system.

Authentication and authorization. Most future users are primarily granted access to the HII from within the MCI by the end user or their delegates. Access can be full or constrained to any subset of features and data identified above. Future users are authenticated primarily using either private key encryption methods, username and password, and/or a biometric authentication (such as face, fingerprint, iris, DNA sample).

Authorization is granted to permit access which may be constrained by numerous factors, including eras of time within the end user's biographical history, data types, metadata types, the features of this invention, and the ability to add new data or configure new data sources for the data collection engine. Authorization is temporarily and revokable by the system for any reason, which immediate limits or ends future user access to one or more features of the system. Access may also be limited to certain allowances within a specified period.

Access to the system is logged to record the duration, nature, and content of all interactions. This logging may be used to optimize the system, retrain learning models, develop future user personas and interests, evaluate the performance of the overall system, provide security audits, detect misuse or abuse of the system, and implement system protection protocols through issuing temporary or permanent revocations of access.

The HII collects contextual metadata on the future user including their name, relationship to the end user, areas of interest, interaction history, custom data sources, contributed system data, and access permissions. The user account management also allows for the configuration of APIs to perform system to system querying and interaction without utilizing a graphical aspect of the HII.

Query interfaces. The HIT possesses several query interfaces to support numerous interaction methods between the future user and the invention. These query interfaces include but are not limited to: Voice and text; Parameter based query search; Future user entity or self-search; Monitoring mode.

Voice and text. The future user may speak or type information into the system which is used by the HII to extract intent, to structure queries, perform searches, and trigger interactions between the future user and the synthetic personality.

Parameter based query search. The future user may enter specific parameters relating to biographical eras in the end user's history, personality traits, periods of transition, biases and stated opinions, or any permitted access within the metadata that has been generated.

Future user entity or self-search. The future user may also perform searches for data that relates to other classified entities within the system, including themselves. By providing data samples, data types, and approximate eras, the future user can see if the PRE methods are capable of confidently recognizing them within the data up to a specific confidence threshold. Depending on the nature of the relationship between the future user and end user, it is possible that they would have had some degree of recorded interaction within the system. If permitted, the system will return a mapping of the interaction times, natures, and data of these interactions.

Monitoring mode. The future user may establish specific data monitoring criteria whereby the HII may contact them should a contemporary event be detected by the DCE which relates to a specific biographical or personality feature within the system. For example, the DCE may provide information about current events which have a strong correlation with the end user's lived experience. In these cases, the HII would contact the future user and notify them of this occurrence.

The HII provides an interface for the future user to upload content directly into the HII. The HII leverages the PRE's trained models to perform classification and recognition of the data. Based on the metadata performs a comparative search within the ISD for associated data. This function performs a search for associated eras and results within the end user's biographical history which align to this data, returning results which have a high degree of similarity to these associated datasets of the end user.

Content viewer. The HII provides a content viewer for viewing returned results graphically within the interface. Because MSDA, DAR-derived, or end user-added content may take on many forms, the content viewer is able to display graphical and time-series data as well as audio, media, and other sources. Where no viewer is available for the identified data type, the data may be displayed in a raw format for the future user to analyze directly or apply their own methods of interpretation or decoding.

Data visualization. The HII provides a data visualization with numerous visualization methods. This is method is a primary feature of the HII because it provides a wide variety of visualization methods for both end user data within the ISD as well as the metadata and metadata trends that have been generated by the PRE.

Common methods of data visualization include but are not limited to: Specific data source visualization (specific devices, data types, periods); Data flow trends (volumetrics, data types) from multiple input sources such as MSDAs as well as DAR-enabled devices; Direct data visualization, such as audio waveform data, text, or images; End-user defined personal milestones and events; Trends analysis, including changes in the accuracy of models, shifting of biases, and biographical events Additionally, the HII provides metadata visualization which includes but is not limited to: Number and distribution of associated MSD or DAR-enabled devices; Time-based trends analysis of metadata; Evaluations of model confidence and performance over time; Visualization of model diversity (types, periods of utilization) of both active and archived models; Interactions between the end user or delegate and the MCI; Query search alignment results; Presence of key words of data features within a specified period; Data disposition histories; ISD data sources, redundancy, volumes, and types; Data sources and integrations of this invention with third party systems; Digital ledger distributions of data within the ISD, specifically visualizing what has been shared via digital ledgers; and Overall system performance.

One primary area for visualization is the indexing of model accuracy over time and the divergence peaks where trained models experienced rapid degradation in their performance, indicating life changes. This metadata is visualized as time-series data where divergence peaks' (the inverse of confidence 'valleys') may be visualized and evaluated as temporary changes or long-term 'plateaus'. These divergence timelines can be used to set search and interaction parameters to optimize interaction with the HII.

Display of and interaction with the synthetic likeness. The HII provides an interface for visualizing the 2-dimensional or 3-dimensional synthetic likenesses of the end user, situations or events within the biographic histories, or other people, places and things which are catalogued and reproducible by the synthetic data generator (SDG) in section [600], personality simulation engine in section [700], or the synthetic likeness of voice generators [800] and [900].

The HII provides an interface to display and interact with any of the synthetic data that may be generated by the system, including image, animation, voice, and textual data. Synthetic data is generated in the way it was originally captured, meaning that image data produces image data, audio data produces audio data, and so forth. For example, this may include stills or animations of the end user which are generated by the system. In the case of animations, the HII may display generated data of synthetically generated actions or recreations of specific data or interactions.

The PSE may pass parameters to the SDG to generate data which is related to biographically historical events. However, based on the interaction between the HII and the future user, the HII may also pass parameters to the SDG to produce synthetic data to support the interaction. For example, as a conversation between the HII and future user unfolds, the HII captures the interactions and classifies them and passes them with the interaction history information to the personality simulation engine (PSE). The PSE applies models to produce the most likely user responses based on end user history as well as the conversational history. The PSE generates a potential response, and then passes this to the synthetic data generator (SDG) which produces a graphical and motion data of the end user. This data is passed to the synthetic likeness and voice generators. The likeness generator produces 2D or 3D representations of the end user based on standard and recorded facial expressions and body language as well as the graphical image mapping data of the SDG. The voice generator encodes the textual response into a verbal response and produces audio representations of the end user's voice. Likeness animation and voice are returned to the future user and visualized within the HIT interface.

3D display of the synthetic likeness. The likeness and the interaction articulated above may be displayed as 2D or 3D representations on the future user's device which they are using to interact with the HII. Depending on the capabilities of their device, this likeness may be displayed on a two-dimensional screen, like a monitor or smartphone, or within a three-dimensional environment to be viewed via augmented or virtual reality glasses or equivalent devices.

The synthetic likeness of the end user is a 3D animated form which may be viewed and interacted with using the HII. The form is based upon the specific characteristics of the end user. Its actions are based on the movements of the end user collected via the MSDA and DAR-enabled devices as well as pose information and habits obtained from image and video analysis.

Spatial visualization of data using 2d and 3d parametric algorithms to translate data volume and type into physical forms. One implementation may be to view data and metadata spatially, including as 3-dimensional topographies. The HII enables alternate or experimental visualizations of the invention's data and metadata holdings using a variety of 2D and 3D spatial visualization algorithms which are designed to translate data into virtually interactive surfaces, volumes, meshes, point clouds, networks, figures or beings, animations, and so forth. By applying either end user or future defined parametric algorithms, data types may be tailored to be represented as an endlessly diverse set of visual features including landscapes, planets, plants, and animals, to name just a few possibilities. The end user may define these characteristics and add pre-defined data visualization methods via the MCI or the future user may perform a similar function via the HII.

Exporting of datasets. The HII enables the exporting of raw data, models, or metadata from the system based on the roles and rights of the future user and the overall system permissions set by the end user or delegate in the MCI. Raw data may be digitally signed with rights management information, specifying its permitted uses, and required disposition as well as any legal agreements governing its use and distribution. Raw data may also have disclaimers associated to it on its accuracy and completeness.

1100—Data Collection Engine (DCE)

This invention utilizes a data collection engine (DCE) to gather contemporary data to support the personality simulation engine, human interaction interface, and associated modules. The DCE plays an important function by continually providing new data for the purpose of search and comparison against the data within the biographical history of the end user. The DCE is a conduit for this invention to proactively source new data to trigger interaction events and provide these interactions to the future user.

Multiple source data aggregator and extractor. The DCE, as identified below, is enabled to aggregate data via multiple sources and protocols and is equipped with a data aggregator function which centralizes and standardizes all incoming data, extracting out key metadata from new sources and forming comparisons against the end user's biographical and metadata information. The extractor function provides a consistent means for gathering pertinent data and time information, metadata, performing pattern recognition analysis, and developing a classification alignment scoring between the data it aggregates and the data within the end user's ISD.

Utilization of the PRE models. New data collected by the DCE is evaluated using a wide range of pattern recognition engine (PRE) models to extract out metadata. This metadata forms the basis of search criteria to find datasets which most strongly correlate to the new data discovered by the DCE. This invention uses the metadata extracted from the DCE and the PRE and identifies relevant periods where the user's activities, biases, and interactions aligned to this new information. When those periods are identified, the periodic data and linked metadata are transferred to the personality simulation engine (PSE) which produces a characterization of the end user's likely views and thoughts on the identified topics and themes discovered by the DCE.

Network connection to the internet. The DCE connects to external data sources over a communications channel to other networked devices. The most common implementation of this would be the internet, however it is expected that there will be a diversity of other networks which might arise within the lifespan of the end user.

Data crawler. The DCE implements data crawling methods by which it utilizes hyperlinks inherent within common HTML-style webpages to navigate and discover new linked data. Data crawlers perform an iterative task of following all relevant links from one page to other pages. Following principles of 'closeness' where all information is only removed through several degrees of connection, crawlers typically are able to catalogue and extract information from an ever-larger system of links and content pages.

For crawlers to work efficiently, they should not attempt to follow all links and download all content due to the exponential complexity of networks. If each page contains 5 links, which each contain 5 links to 5 other pages, then the number of pages will rise exponentially and so will the computational power and storage required to retain and process this information. Instead, the DCE implements crawlers which are specifically tailored to evaluate the alignment of the content that they use with the interests and activities of the end user. By leveraging the neural network models of the user and the previously generated metadata, the DCE can determine which links and subjects are of the most value and potential alignment to the end user. A ranking can be derived on each page which is loaded, and subsequent branches of information which diverge from the end user metadata previously generated by the PRE can be curtailed.

As an alternate approach, the DCE may also be configured to find moderately or significantly divergent information as a point of contrast and comparison. Contrasting information is measured against bias metadata or when the data has a low classification with the models within the PRE. This information may be useful for both the end user and any future users to understanding which topics were outside or in opposition to the interests and biases of the end user. Seeing the countercultural influences which the end user is ignoring or resistant to provides great insight into the personality and views of the end user. Within their lifespan, the end user may wish to observe how their biases are limiting their exposure to alternate viewpoints and may choose to use this feedback to make changes to their actions. Alternatively, they may also reinforce their behaviors. Countervailing data samples as triggers for interaction may also be utilized.

Media extraction of images, videos, audio streams and other non-textual information. The DCE can extract content from media, including images, videos, streams, and other sources. Data extraction allows for subsets of data to be analyzed and stored within the ISD and to be classified through various means.

API connection to search engine. The DCE can be configured through the MCI to connect to third party search engine services to directly perform keyword, Boolean, image, graph, and other search processes using ISD data and metadata subsets. Searching using these methods provides a means of retrieving results via third party aggregators who may provide date and time information to evaluate which articles are most recent as well as scores as to which align most highly to the keywords and concepts contained within the end user's metadata. These results provide opportunities for the PRE to measure the alignment of the end user's metadata against current events (number of results and degree of matching) for a trends analysis. Results also provide opportunities to gather content and to direct the crawler features in beginning an iterative processing of all related subject matter content.

User-defined data sources. Using the MCI, the end user may define data sources for the DCE to specifically reference. These may be areas of specific interest for the end user or they may general but preferred resource locations for search and discovery. Similarly, the HII allows the future user to define such data sources. These user-defined sources are catalogued and stored in the ISD.

Historical links and archives. The DCE may also leverage data from DAR-enabled devices to evaluate the end user's historical navigations and links and to periodically probe these sources for new content. If the end user frequently referenced certain news and information sites for example, the DCE can continue to draw reference from these sites into the future.

RSS feeds. The DCE may be configured to reference RSS (an acronym for "really simple syndication") feeds which are frequently updating summaries of new content from one or more sources, aggregated for easy consumption. This 'push' method of sharing new information provides an optimal means for the DCE to continue to monitor historical links that the end user frequented.

Digital ledgers. The DCE may be configured to draw from digital ledger systems and to subscribe to unencrypted posts, media, and messages. Digital ledgers may contain information similar to RSS feeds where a distributed network is pushing new content. They may also be introducing new content through the signing of digital assets such as non-fungable tokens (NFTs) which provide insight into current interests and topics in society.

Peer-based communications, including LoRa style networks. The DCE may be configured to connect to alternate networks such as peer to peer networks. Peer-based networks may work like torrents, where multiple users form a network for distributing data, mesh networks, where multiple nodes are established to push data from one recipient to all connected recipients, and wireless long range (LoRa) networks which operate in a means like both peer and mesh networks.

The method taught by the present invention significantly enhances the scope of data collection from seconds to hours within the average lifespan to months, years, and decades of information.

The method taught by the present invention centralizes the digital information generated on digital devices such as sensors, smartphones and consolidates this into a primary information storage device.

The method taught by the present invention utilizes pattern recognition models to minimize the transmission and recording of data which does not contain significant diversity as to describe a biographical event.

The method taught by the present invention applies cryptographic methods to digital write data and data integrity information to an unalterable digital ledger.

The method taught by the present invention achieves far greater categorization and retrieval of data through the application of pattern recognition and metadata analysis and by selectively applying narrative synthesis to describe or reproduce events accurately in the future, rather than simply replaying original sensor information.

The method taught by the present invention signs experience information cryptographically to demonstrate the authenticity of the experience for future review.

The method taught by the present invention overcomes major infrastructural issues with the recording and storage of mass data including data discovery.

The method taught by the present invention applies a distributed ledger technology for the durable decentralized storage mechanism with other users across a peer-based network.

The method taught by the present invention minimizes the storage of data by disposing and substituting original data with synthetic data which can be created on demand.

The method taught by the present invention creates temporal indexes by monitoring the occurrence of temporary or permanent failures of predictive classification models to identify eras of biographical change.

The method taught by the present invention utilizes time-based disposition models optimize data storage requirements.

The method taught by the present invention provides an avatar-driven interface for interaction with the data by other humans.

The method taught by the present invention actively monitors trends in data across a network to dynamically find relevant data from the original human's inventory of experiences and thoughts and displays this information through the user interface.

Benefits for the End User

This invention provides a myriad of benefits for the end user which are unmet within the current state of technology today. These benefits include:

This invention addresses and resolves an acute point of stress for most living humans, namely their physical mortality and the preservation of their non-physical characteristics, including personalities, experiences, thoughts, and biases. The subject human's stress associated to death and the cessation of their physical being will be reduced with the knowledge that a representation of their life and identity will persist beyond death in some capacity.

This invention provides a mathematically verifiable 'afterlife' of experiences which are housed within an energy-based system as described by most religions.

This invention provides an effective vehicle for transferring knowledge of personal and social interest between generations supporting enculturation, identity, and education with a level of insight and detail unavailable through any other traditional media.

This invention provides a means of interacting with an interface which represents recognizable patterns of human action, movement, speech not present in other modes of representation.

This invention will have a positive effect on human behaviors. Adopters of this technology will be aware that their lives are being self-recorded, and the act of living is an act of autobiography will cause encourage positive life choices and actions.

This invention will address concerns about how one's life is being represented beyond their death. The application of cryptographic methods and the adoption of a distributed ledger will make it mathematically impossible using known methods to alter the record of lived experiences and actions.

This invention will provide the descendants of a human a means of interacting with the lived history, personality, and experiences after their death.

This invention will provide a means of establishing inter-generational understanding of the priorities and challenges faced within the lifespan of a human.

This invention will create a body of knowledge to support future historical and anthropological researchers in understanding the motivations of this era of social and ecological turbulence which will doubtlessly be one of intense future scrutiny.

This method will preserve intangible cultural artifacts, such as language, oral histories, factual recordings of events, cultural mores and actions, rituals, sayings, and experiences, reducing the fear that the loss of each generation will result in the irretrievable loss of culture or human knowledge and addressing the mandate of large organizations such as the Intangible Cultural Heritage branch of the United Nations Economical, Scientific, and Cultural Organization (UNESCO).

This invention, within the lifetime of the user, will support the recall of events that the individual was present for or to provide insight into events where the individual has no memory such as when they are sleeping, were absent, or for which they no longer can recall due to natural or artificial memory loss.

This invention will allow the user to possess a record for their actions and the actions of others, establishing a solid foundation for legal or civil defense against charges or accusations.

This invention will enable the user to possess a wealth of personal information which can be analyzed to make critical observations of their lifestyle patterns, habits, and biological rhythms.

This invention will enhance the speed and accuracy of individual and group recall through the ability to leverage the pattern recognition engine to quickly locate and replay critical information.

This invention will enable the ability to share and key aspects of the user's life to a social community of peers, family, community, and society.

This invention will enable greater self-reflection of the user on how to optimize the time within their life by visually seeing trends and pattens represented for any era that their data covers.

This invention will enable the user to share, in part or in whole, original data, metadata, or pattern recognition and generation models to any inheritor(s) of their designation. For example, when a child of the primary user of this invention grows up and moves out on their own, they can take with them a copy of the data which documents their upbringing and a record of their familial experiences. They may then use this dataset as the foundation for continuing their own branched life narrative, separate from the life of the primary user. This branching of data will provide further insurance against the potential catastrophic loss of a single dataset.

This invention will provide the basis for advanced future computing methods which will support the creation more advanced human forms through robotics or biological synthesis (i.e. recreating humans through technologies which are still beyond the technological reach of society).

This invention will provide the basis for advancing neurolinguistic theories which identify the possibility that the acquisition of language plays a role in the structuring of the brain, so that the knowledge of the words and languages we speak may be used to infer the biological structure of the brain. The storage of representational brain information could become a critical component to future technologies which are able to recreate brain structures and functions using synthetic or artificial means, effectively forming the foundation of a reincarnation of artificial or biological brain structures present in the original human organism.

This invention will reduce the environmental impacts of other means of self-preservation and result in method of self-expression and self-preservation which achieves greater carbon neutrality and lessens ecological impacts.

This invention will reduce the societal, environmental, and financial cost and burden of mass storage through the optimization of stored data down to summary patterns and models.

This invention will provide a significant optimization in data storage through the use of pattern recognition engines and synthetic data generators which create and utilize artificial neural networks.

The system is set to run on a computing device or mobile electronic device. A computing device or mobile electronic device on which the present invention can run would be comprised of a CPU, Hard Disk Drive, Keyboard, Monitor, CPU Main Memory and a portion of main memory where the system resides and executes. The modules described may be collocated on one computing device or distributed across a number of separate computing devices. Computer and mobile electronic devices like these are well known in the art and are not pertinent to the invention. The system can also be written in a number of different languages and run on a number of different operating systems and platforms and be delivered remotely or as an isolated, stand-alone application located on or off site.

Although the present invention has been described in considerable detail with reference to certain preferred versions thereof, other versions are possible. Therefore, the point and scope of the appended claims should not be limited to the description of the preferred versions contained herein.

As to a further discussion of the manner of usage and operation of the present invention, the same should be apparent from the above description. Accordingly, no further discussion relating to the manner of usage and operation will be provided.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

Thus, it is appreciated that the optimum dimensional relationships for the parts of the invention, to include variation in size, materials, shape, form, function, and manner of operation, assembly and use, are deemed readily apparent and obvious to one of ordinary skill in the art, and all equivalent relationships to those illustrated in the drawings and described in the above description are intended to be encompassed by the present invention.

Furthermore, other areas of art may benefit from this method and adjustments to the design are anticipated. Thus, the scope of the invention should be determined by the appended claims and their legal equivalents, rather than by the examples given.

The embodiments of the invention in which an exclusive property or privilege is claimed are defined as follows:

1. A method for capturing, preserving, and representing human experiences and personality through a digital interface, comprising:

digital activity recording (DAR) software installed on a personal computing device to capture and transmit digital device usage patterns;

a multimodal sensor device array (MSDA) which captures human activities and interactions within an environment;

an information storage device (ISD) which captures and cryptographically signs sensor information and cooperates with an interface to distribute the sensor information to a least one computer on a network that shares data and resources via wired or wireless technologies;

a methods control interface (MCI) that configures a plurality of modules;

a pattern recognition engine (PRE) which analyzes data and categorizes information with metadata based on detected interactions and events; and a synthetic data generator (SDG) which utilizes a classification and categorization metadata created by the PRE to produce new data which is synthetic in nature but based on representative features present in end user data, wherein the SDG is configured to produce synthetic data and data generation models, which are leveraged by the DAR, the MSDA, the ISD, the MCI, and the PRE, and wherein the SDG uses a Generative Adversarial Network (GAN) process to develop data creation and evaluation models; the GANs utilize two distinct neural networks which leverage each other iteratively for mutual refinement;

the first neural network is known as a Discriminator, and the second neural network is known as a Generator;

each neural network iteratively leverage each other for mutual training and refinement;

the role of the Discriminator is to predict whether data sample derived form a sensor or data within the ISD is real or synthetic;

alternating datasets are fed into the Discriminator;

the first dataset is a collection of labeled data which is the real data;

the second dataset is data from the Generator, which at first randomly generated data which matches the same or approximate characteristics of real data;

wherein using the first and second dataset, the Discriminator is trained to recognize whether the data is real or generated;

the discriminator outputs a 1 when the discriminator identifies real data, a 0 when the discriminator identifies generated data, and a floating-point number to reflect the Discriminator classification confidence; and a low confidence of classification is 0.1 whereas a high confidence is between 0.9 to 1, wherein the plurality of modules comprises the DAR, the MSDA, the ISD, the PRE, the SDG, the GAN, the Discriminator, and the Generator.

2. The method of claim 1, wherein the role of the Generator is to produce data with the characteristics which the Discriminator will classify as real data and score as high of a confidence as possible;

random data samples, sometimes known as seeds, are inputted into the Generator, which uses a neural network to produce an output sample;

the output sample is fed into the input of Discriminator, as identified; and the results of the Discriminator, between 0 and 1, are fed back into the Generator through a process known as backpropagation to update the Generator neural network weights, thus changing a future output.

3. The method of claim 2, wherein the Discriminator and the Generator are trained iteratively;

with each training iteration, the Discriminator gets better at differentiating between real data and generated data;

conversely, with each iteration the Generator gets better are at producing outputs which are better at fooling the Discriminator; and through an extensive set of iterations, the Generator is configured to produce synthetic data which is highly realistic, exceeding a threshold of confidence by the Discriminator.

4. The method of claim 2, wherein the GAN is configured to reproduce synthetic data which simulates the sensor, end user generated, or any dataset contained within the ISD;

synthetic data achieves an acceptable threshold of realism to accurately simulate the data features of the original data to meet both Discriminator analysis and the end user subjective quality;

synthetic data generation is generated in accordance with parameters which manipulate the nature and the content of the GAN output; and synthetic data specifically enables the representation of the visual, verbal, auditory appearance of the end user and the end user environment.

5. The method of claim 4, wherein generating models for the personality simulation engine (PSE) and the synthetic likeness and voice engines (SLE and SVE);

such generative models generated within the SDG are exportable for use within the PSE, SLE, and SVE; and these exportable models are used by the PSE, the SLE and SVE engines to produce new content to simulate biographical or interaction events.

6. The method of claim 1, further comprising a personality simulation engine (PSE) which utilizes the classified metadata generated within the PRE to synthesize data which represents the reactions and modes of response to stimulus which is representationally like those of the end user;

a simulated personality produces sequences of data which represent actions, speech methods, motions, and events similar to the actions, speech methods, motions, and events of the end user;

the PSE creates these recognizable outputs based on input stimulus from a variety of different sources but is primarily driven by the human interaction interface (HII);

the PSE generates interaction information using multiple methods including: Text-based speech interaction, data and associated metadata extracts which align to the topics classified within the interaction, and results from the classification of data provided by a future user.

7. The method of claim 6, wherein the PSE identifies the era(s) in a life of the end user to simulate based on life periods identified by the input and specifications of the future user;

wherein the three general settings for life scope specification are: time period-based specification, open specification, and aggregate life specification;

the PSE collects input stimulus and has several primary modes of interaction including conversational interactions between a future user and the PSE via the HII, replay or of data from specific periods and events; recreations of events which occurred, miming or re-enacting events; providing external data; and direct system to system queries;

the PSE permits system to system queries, providing an intermediate layer for another system to query data rapidly and request metadata types, periods of time, and data with greater specificity;

the PSE is configured to return fully synthetic data, a hybrid mix of real and synthetic data, or samples of original data captured by the end user and stored within the ISD; and the PSE returns a metadata response which represents how the end user would likely interpret and respond to a query.

8. The method of claim 7, wherein the PSE responds to queries derived from interactions with the future user within a time-constrained context of an engagement lasting a few seconds to several hours or longer;

within this constrained interaction window, the PSE generates a set of responses to external stimulus which are configured to be as highly representative of the reactions of the end user within a user-selected window of the end user biographical history; and the PSE accepts these interactions via either the MCI interface, controlled by the end user or the end user delegate, or through the HII.

9. The method of claim 8, wherein the PSE evaluates the metadata patterns, classifications, and narratives generated by the PRE and creates models capable of generating predictive behavior data;

using the classified biographical actions of the end user, the PSE evaluates the data and metadata which describes the environments and events which correlate as triggers to the end user response; wherein the triggers are the time of day, the nature of interaction, and stimulus;

the PSE analyzes multiple data streams to find which events may have triggered reactions from the end user; and the PSE categorizes these events into triggering sets based on a broad spectrum of metadata, including textual analysis, human to human interaction patterns, environmental factors, cyclical patterns, to determine how the end user reacted to interaction, confrontation, positive and negative stimulus, environment, and sets of metadata derived by the PRE.

10. The method of claim 9, wherein based on a subset recorded data that follows the triggers, the PSE uses predictive modelling to produce an array of possible responses that the end user would most likely demonstrate given all correlated triggers;

the PSE samples biographical data on what the end user said and did in response to a similar set of triggers as well as generates a list of alternate responses based on observed responses to other scenarios;

while the triggers of the original event and the HII interaction are unlikely to be identical, the PSE implements a cascading evaluation of all known triggers and gradually reduces the specificity of the triggers until a user-defined threshold is reached of possible predictions of the end user reactions; and an action and response is then generated.

11. The method of claim 6, wherein the PSE record of the HII interaction session adds additional inputs to help guide the consistency of the interaction;

as a future user interacts with the HII and the HII interactions are passed to the PSE, the responses outputs of the PSE are channeled back into the input for subsequent engagements to provide a feedback cycle;

the PSE utilizes these response records in formulating subsequent responses as to not backtrack onto previously discussed topics, as well as to build on the sentiment of the conversation; and the PSE uses the session memory to avoid entering cyclical looping engagements which could result in unrealistic results including repeated conversation topics or continual looping engagement patterns.

12. The method of claim 6, wherein the natural language outputs from the PRE are configured to identify the language and vocabulary as the language is spoken by the end user, not as grammatical rules dictate.

13. The method of claim 6, wherein the PSE utilizes the MCI to engage the end user on a series of sessions to capture this information through a recorded interview process;

during the process, the end user body language is captured by the MCI and recorded as a training set for modelling and reference;

body posture and gross body movements are captured via motion capture;

finer movements comprising at least finger movements, facial expressions and minor motions of the head and neck, are all captured and analyzed via video;

wherein the body posture, the gross body movements and the finer movements are classified for intensity, motion and posture using external training data; and to provide a representative set of samples, the recorded interview process must be repeated several times over the life of the end user to gather data on how they respond throughout the life of the end user.

14. The method of claim 6, wherein the PRE and the DAR provide an opportunity to capture the end user topics of interest;

interest mapping is aligned to the period of life of the end user and the PRE and the DAR is configured to chart the interest mapping as progressions in interest and bias over time;

interests are derived based on the consistency and frequency of recognizable features in the end user datasets;

features with high degrees of reoccurrence over an extended time period or periodic reoccurrences after sporadic periods of low occurrence represent heightened interest and bias toward specific activities and interactions;

the interactions between the future user and the PSE references this subjective interest to demonstrate topics of specific interest in the end user recorded history;

based on the patterns of interactions by the future user, data which is indexed with heightened potential interest is configured to be prioritized for return; and the PSE is configured to either reference the content or display the content as part of the interaction response through the HII and pantomime or paraphrase content from such sources as the content relates to the era of life of the end user that is the subject of the interaction.

15. The method of claim 6, wherein the PSE is configured to sample a sliding window of time from biographical experiences of the end user, associated metadata, and models to represent likely responses to interactions suitable representing the personality of the end user.

16. The method of claim 6, wherein data selection is weighed based on the indexing of uncommon events as key points of life;

periods of heightened novelty, comprising the presence of novel features within datasets, or change, when predictive or classification models experienced a degradation in accuracy or confidence, are the two primary means of indexing such-unique events;

the PRE creates metadata indices which identify moments or periods of time where models failed to accurately predict or classify the patterns of the end user;

by over-indexing on these periods of change, the PSE generates interactions and shares knowledge in these periods as primary areas of interest and potential interaction with a user;

the PSE is configured to draw from these areas in a weighted manner in preparing responses to user interaction.

17. The method of claim 1, further comprising a synthetic likeness engine (SLE) which produces a likeness of the end user as representations of animated two-dimensional images or three-dimensional forms;

for each era of the end user biographical history, this likeness changes to represent the appearance of the end user during that period of life of the end user;

the likeness is a virtual avatar which is intended to walk, speak, gesture, pose, move, and act as closely as possible to the end user with the data collected during the lifetime of the end user.

18. The method of claim 17, wherein the virtual avatar uses a blended method to make the virtual avatar realistic through the combination of gross animation of the 3D form combined with fine animation of the textures which are mapped on the virtual avatar to give specific features;

gross movements are informed by sensor data, image, and video materials which capture how the end user moved in life;

fine features are generated from likeness images produced by the synthetic data generator (SDG); and these images are then texture mapped using common UV mapping methods to align to the geometry of the body of the 3D model where the combination of 3D form with applied texture mapping produces a realistic likeness of the human.

19. The method of claim 18, wherein additional image or biometric reference data is added via the MCI to complete any required image datasets for a realistic and comprehensive image of the body, skin, and physical characteristics of the end user.

20. The method of claim 18, wherein the SLE uses templated 3D forms of children and adults as the basis for the virtual avatars; wherein templates are generic gendered templates which are pre-built to represent common body shapes, body mass, musculatures, fats, limb lengths, flexibility, hair growth patterns, skin tones and shades, manual dexterity, facial features, and proportions;

templates are then adapted using data features recognized by the PRE; and all the physical features of the body are used to adjust the templates with specific parameters to match the body geometry of the end user at specific times in the end user biographical history.

21. The method of claim 20, wherein the SLE is capable of importing assets which represent the real assets and accessories of life and applying them to the model;

and wherein a combination of wear is configured to be detected by the PRE or user defined;

and wherein the end user optionally specifies a different set of clothes to represent specific eras or activities within the end user biographical history.

22. The method of claim 20, wherein the combination of motion with speech from the PRE provides the basis for the degree and nature of hand gestures and movements.

23. The method of claim 20, wherein the SDG references all available image data to reproduce the facial mapping of the end user with realistic blemishes, wrinkles, and micro-expressions which will significantly enhance the realism of the virtual avatar;

facial image data from the SDG is imported as image data by the SLE;

the facial geometries are mapped using a facial recognition model and applied against the 3D geometry of the virtual avatar;

as the virtual avatar speaks and moves, the mapping updates based on these characteristics; and the facial geometries extracted by the PRE and generated by the SDG are applied to update the 3D virtual avatar.

24. The method of claim 20, wherein the geometries of the virtual avatar are adjusted through measurements taken from image and video data;

the SLE uses photogrammetry to perform this function on the human body.

25. The method of claim 17, further comprising a Synthetic Voice Engine (SVG) that synchronizes with the Synthetic Likeness Engine (SLE) to produce an integrated audio overlay which aligns to the animation and movement of the virtual avatar character;

the SVE uses the vocal characteristics of the end user that are identified in the PRE;

the SVE utilizes the voice generation models developed by the SDG and narrates the text that is created from the personality simulation engine (PSE) to produce a realistic audio that represents the end user at various ages and periods of the end user biographical history.

26. The method of claim 25, wherein if the virtual avatar is recreating a conversation or a monologue that the end user delivered within the history, the SVE approximates delivery of the historical event with as much accuracy as possible; and if the virtual avatar is narrating an event, describing what happened instead of re-enacting the event, then a separate model is configured to be used for clarity.

27. The method of claim 26, wherein the SDG reproduces trained voice print models, and the personality simulation engine (PSE) produces the spoken language content and metadata;

together, the SVN combines the trained voice print models and the spoken language content and metadata outputs to generate acoustic information;

the SVN adapts the acoustic data output of the trained voice print models and the spoken language content and metadata models to adjust pitch, cadence, intonation, and other acoustic characteristics to align to the contextual parameters of the interaction and the relative age of the virtual avatar of the end user by applying audio adjustment filters which modulate the acoustic properties of the voice; and the modulation of the acoustic properties of the voice is performed based on the output of the PSE and aligned to the timing of the SLE animation of the form of the virtual avatar.

28. The method of claim 27, wherein the PRE performs a sentiment analysis of the vocal characteristics of the voice data within the ISD;

this sentiment data is linked as metadata to the original data samples; and sentiment adjustments to the synthetic voice are generated by the PSE based on the predictive conversation models developed around the interactions of the end user.

29. The method of claim 28, wherein for re-enactments of the voice, the characteristics of the virtual environment that the virtual avatar is occupying have an impact on the vocal properties that the virtual avatar is sharing; and environmental filters are configured to apply to the voice to simulate the context of the various rooms and environments that the end user occupied to a more realistic interaction experience for the future user.

30. The method of claim 29, wherein the SVE also utilizes the SDG to produce environmental sounds to layer over the vocal simulation to add context; and the nature of the augmentation will vary depending on whether the sounds are contextual and secondary or related to the primary topic of the interaction.

* * * * *